United States Patent
Berger et al.

(10) Patent No.: US 9,920,373 B2
(45) Date of Patent: Mar. 20, 2018

(54) BIOMARKERS OF RESPONSE TO PROTEASOME INHIBITORS

(71) Applicant: MILLENNIUM PHARMACEUTICALS, INC., Cambridge, MA (US)

(72) Inventors: Allison Berger, Arlington, MA (US); Nibedita Chattopadhyay, Wellesley, MA (US); Erik M. Koenig, North Reading, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 252 days.

(21) Appl. No.: 14/356,974

(22) PCT Filed: Nov. 9, 2012

(86) PCT No.: PCT/US2012/064496
§ 371 (c)(1),
(2) Date: May 8, 2014

(87) PCT Pub. No.: WO2013/071142
PCT Pub. Date: May 16, 2013

(65) Prior Publication Data
US 2015/0152502 A1 Jun. 4, 2015

Related U.S. Application Data

(60) Provisional application No. 61/558,474, filed on Nov. 11, 2011, provisional application No. 61/721,818, filed on Nov. 2, 2012.

(51) Int. Cl.
| | |
|---|---|
| C12Q 1/68 | (2018.01) |
| A61K 31/69 | (2006.01) |
| A61K 38/06 | (2006.01) |
| G01N 33/50 | (2006.01) |
| G06F 19/00 | (2018.01) |

(52) U.S. Cl.
CPC ............ *C12Q 1/6886* (2013.01); *A61K 31/69* (2013.01); *A61K 38/06* (2013.01); *G01N 33/5011* (2013.01); *G06F 19/328* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2008/0293055 A1 | 11/2008 | Freeman et al. |
| 2010/0075356 A1 | 3/2010 | Hoffman et al. |
| 2011/0081362 A1 | 4/2011 | Elledge et al. |
| 2011/0081651 A1 | 4/2011 | Hillan |
| 2011/0118298 A1 | 5/2011 | Fritz et al. |
| 2011/0189204 A1 | 8/2011 | De Coster et al. |
| 2011/0250133 A1 | 10/2011 | Lattuada et al. |
| 2011/0253155 A1 | 10/2011 | Taniguchi |
| 2011/0256155 A1 | 10/2011 | Huang et al. |
| 2012/0252745 A1 | 10/2012 | Blagg et al. |
| 2012/0252749 A1 | 10/2012 | Shanmugam et al. |

FOREIGN PATENT DOCUMENTS

| | | |
|---|---|---|
| WO | 2009154737 A1 | 12/2009 |
| WO | 2011056688 A2 | 5/2011 |

OTHER PUBLICATIONS

Kranenburg Onno; "The KRAS oncogene: past, present, and future". Biochimica et Biophysica Acta. (2005) 1756 (2): 81-2.*
Aukema T., et al. Is 18F-FDG PET/CT Useful for the Early Prediction of Histopathologic Response to Neoadjuvant Erlotinib in Patients with Non-Small Cell Lung Cancer? J Nucl Med 2010; 51:1344-1348.
Baudy, A., et al. FDG-PET is a good biomarker of both early response and acquired resistance in BRAFV600 mutant melanomas treated with vemurafenib and the MEK inhibitor GDC-0973. EJNMMI Research 2012, 2:22.
Chen, Z., et al. A murine lung cancer co-clinical trial identifies genetic modifiers of therapeutic response. Mar. 29, 2012, vol. 483, Nature.
de Geus-Oei, L., et al. Predictive and Prognostic Value of FDG-PET in Nonsmall-Cell Lung Cancer. Cancer Oct. 15, 2007, vol. 110, No. 8.
Hoekstra, C., et al. Prognostic Relevance of Response Evaluation Using [18F]-2-Fluoro-2-Deoxy-D-Glucose Positron Emission Tomography in Patients With Locally Advanced Non-Small-Cell Lung Cancer. J Clin Oncol 23:8362-8370, 2005.
Kawada, K., et al. Relationship between 18F-Fluorodeoxyglucose Accumulation and KRAS/BRAF Mutations in Colorectal Cancer. Clin Cancer Res; 18(6) Mar. 15, 2012.
Clinical and biological significance of RAS mutations in multiple myeloma. Leukemia (2008) 22, 2280-.2284; doi:10.1038/leu.2008.142; published online Jun. 5, 2008.
Roberts, P., et al. KRAS Mutation: Should We Test for It, and Does It Matter? J Clin Oncol 31:1112-1121, 2013.
Sunaga, N., et al. Usefulness of FDG-PET for early prediction of the response to gefitinib in non-small cell lung cancer. Lung Cancer (2008) 59, 203-210.
Van den Abbeele, A., et al. ACRIN 6665/RTOG 0132 Phase II Trial of Neoadjuvant Imatinib Mesylate for Operable Malignant Gastrointestinal Stromal Tumor: Monitoring with 18F-FDG PET and Correlation with Genotype and GLUT4 Expression. J Nucl Med 2012; 53:567-574.
Al-Ghamdi S, Albasri A, Cachat J, Ibrahem S, Muhammad BA, et al. (2011) Cten Is Targeted by Kras Signalling to Regulate Cell Motility in the Colon and Pancreas. PLoS ONE 6(6): e20919. doi:10.1371/journal.pone.0020919.

(Continued)

*Primary Examiner* — Jeffrey H Murray
(74) *Attorney, Agent, or Firm* — Honigman Miller Schwartz and Cohn LLP; Lucy X. Yang; Jonathan P. O'Brien

(57) ABSTRACT

Disclosed are markers associated with sensitivity to treatment with proteasome inhibitors. Sensitivity is observed when RAS gene is wild type in tumor cells. Compositions and methods are further provided to assess markers of marker genes to predict outcome of treatment using proteasome inhibitors to patients having a solid tumor, such as a lung tumor or a colon tumor.

18 Claims, 5 Drawing Sheets

(56) References Cited

OTHER PUBLICATIONS

Figure 1:
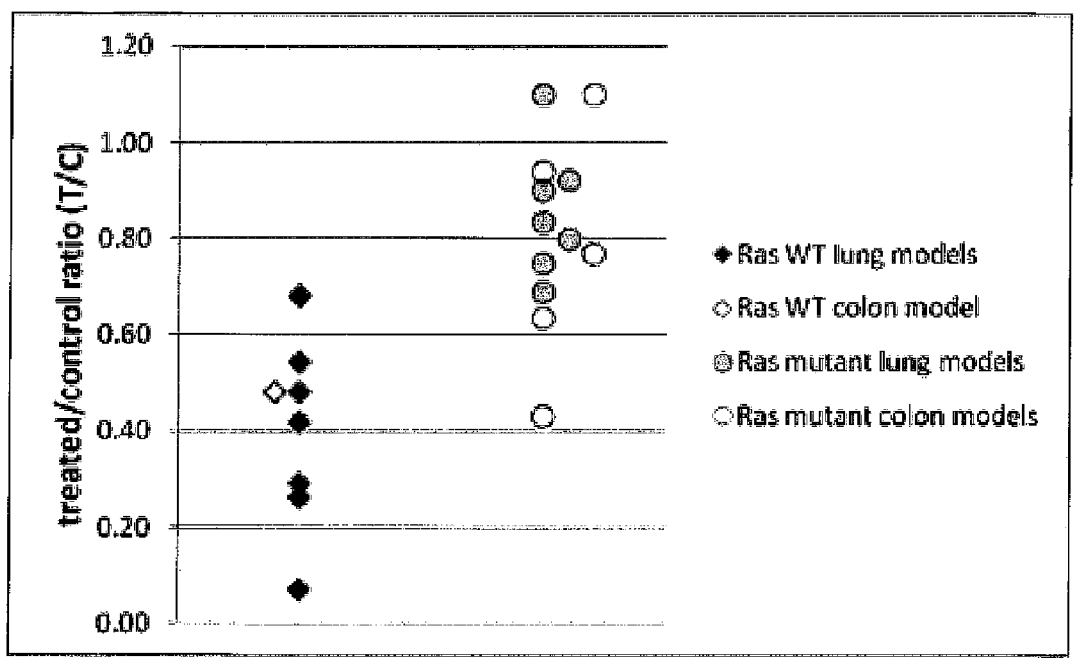

Chattopadhyay N, Berger AJ, Koenig E, Bannerman B, Garnsey J, Bernard H, et al. (2015) KRAS Genotype Correlates with Proteasome Inhibitor Ixazomib Activity in Preclinical In Vivo Models of Colon and Non-Small Cell Lung Cancer: Potential Role of Tumor Metabolism. PLoS ONE 10(12): e0144825. doi:10.1371/journal.pone.0144825.

Chattopadhyay, N., et al. Association of K-Ras genotype with xenograft tumor response to the investigational proteasome inhibitor MLN9708. Poster presented at EORTC (2012) AACR-NCI-EORTC Symposium on Molecular Targets and Cancer Therapeutics—24th (abst due: Jun. 27, 2012 starts: Nov. 6, 2012).

Ross, J., et al. Biomarker-Based Prediction of Response to Therapy for Colorectal Cancer. Am J Clin Pathol 2012; 134:478-490.

Andreyev, H., et al. Kirsten ras Mutations in Patients with Colorectal Cancer: the Multicenter "RASCAL" Study. Journal of the National Cancer Institute, vol. 90, No. 9, May 6, 1998.

Extended European Search Report for corresponding application No. EP 12847968.0 dated Sep. 28, 2015.

International Search Report and Written Opinion of corresponding application No. PCT/US12/64496 mailed Mar. 25, 2013.

International Preliminary Report on Patentability for corresponding application No. PCT/US12/64496 mailed May 22, 2014.

Smith, G., "Activating K-Ras mutations outwith 'hotspot' codons in sporadic colorectal tumours—implications for personalised cancer medicine," British Journal of Cancer, 2010, 102(4), pp. 693-703.

\* cited by examiner

FIG. 4.

FIG. 4A

Cell lines

KRas WT cells: H1975  HCC827  SW48
KRas Mut cells: A549  HCT116  SW48 G13D

FIG. 4B

Tumor xenografts

| PHTX132Lu (WT) | PHTX192Lu (Mutant) | NCI-H1650 (WT) | A549 (Mut) | SW48 (WT) | SW48-KRas-G13D (Mut) |
|---|---|---|---|---|---|
| T/C 0.29 | 0.8 | 0.55 | 0.9 | 0.425 | 1.055 |

SEQUENCE LISTING

```
<160> NUMBER OF SEQ ID NOS: 9

<210> SEQ ID NO 1
<211> LENGTH: 5312
<212> TYPE: DNA
<213> ORGANISM: Homo sapiens

<400> SEQUENCE: 1
ggccgcggcg  gcggaggcag  cagcggcggc  ggcagtggcg  gcggcgaagg  tggcggcggc      60
tcggccagta  ctcccggccc  ccgccatttc  ggactgggag  cgagcgcggc  gcaggcactg     120
aaggcggcgg  cggggccaga  ggctcagcgg  ctcccaggtg  cgggagagag  gcctgctgaa     180
aatgactgaa  tataaacttg  tggtagttgg  agctggtggc  gtaggcaaga  gtgccttgac     240
gatacagcta  attcagaatc  attttgtgga  cgaatatgat  ccaacaatag  aggattccta     300
caggaagcaa  gtagtaattg  atggagaaac  ctgtctcttg  gatattctcg  acacagcagg     360
tcaagaggag  tacagtgcaa  tgagggacca  gtacatgagg  actggggagg  gctttctttg     420
tgtatttgcc  ataaataata  ctaaatcatt  tgaagatatt  caccattata  gagaacaaat     480
taaaagagtt  aaggactctg  aagatgtacc  tatggtccta  gtaggaaata  aatgtgattt     540
gccttctaga  acagtagaca  caaaacaggc  tcaggactta  gcaagaagtt  atggaattcc     600
ttttattgaa  acatcagcaa  agacaagaca  gggtgttgat  gatgccttct  atacattagt     660
tcgagaaatt  cgaaaacata  agaaaagat  gagcaaagat  ggtaaaaaga  agaaaaagaa     720
gtcaaagaca  aagtgtgtaa  ttatgtaaat  acaatttgta  cttttttctt  aaggcatact     780
agtacaagtg  gtaatttttg  tacattacac  taaattatta  gcatttgttt  tagcattacc     840 taatttttttt  cctgctccat  gcagactgtt  agcttttacc  ttaaatgctt  attttaaaat     900
gacagtggaa  gtttttttttt  cctctaagtg  ccagtattcc  cagagttttg  gttttttgaac     960 tagcaatgcc  tgtgaaaaag  aaactgaata  cctaagattt  ctgtcttggg  gttttttggtg    1020 catgcagttg  attacttctt  attttttctta  ccaattgtga  atgttggtgt  gaaacaaatt    1080
```

```
aatgaagctt ttgaatcatc cctattctgt gttttatcta gtcacataaa tggattaatt    1140
actaatttca gttgagacct tctaattggt ttttactgaa acattgaggg aacacaaatt    1200
tatgggcttc ctgatgatga ttcttctagg catcatgtcc tatagtttgt catccctgat    1260
gaatgtaaag ttacactgtt cacaaaggtt ttgtctcctt tccactgcta ttagtcatgg    1320
tcactctccc caaaatatta tatttttttct ataaaaagaa aaaatggaa aaaaattaca    1380 aggcaatgga aactattata aggccatttc cttttcacat tagataaatt actataaaga    1440
ctcctaatag cttttcctgt taaggcagac ccagtatgaa atggggatta ttatagcaac    1500
cattttgggg ctatatttac atgctactaa attttttataa taattgaaaa gattttaaca    1560
agtataaaaa attctcatag gaattaaatg tagtctccct gtgtcagact gctctttcat    1620
agtataactt taaatctttt cttcaacttg agtctttgaa gatagttta attctgcttg    1680 tgacattaaa agattatttg ggccagttat agcttattag gtgttgaaga gaccaaggtt    1740
gcaaggccag gccctgtgtg aacctttgag ctttcataga gagtttcaca gcatggactg    1800
tgtccccacg gtcatccagt gttgtcatgc attggttagt caaaatgggg agggactagg    1860
gcagtttgga tagctcaaca agatacaatc tcactctgtg gtggtcctgc tgacaaatca    1920
agagcattgc ttttgtttct taagaaaaca aactcttttt taaaaattac ttttaaatat    1980
taactcaaaa gttgagattt tggggtggtg gtgtgccaag acattaattt ttttttaaa    2040 caatgaagtg aaaaagtttt acaatctcta ggtttggcta gttctcttaa cactggttaa    2100
attaacattg cataaacact tttcaagtct gatccatatt taataatgct ttaaaataaa    2160
aataaaaaca atccttttga taaatttaaa atgttactta ttttaaaata aatgaagtga    2220
gatggcatgg tgaggtgaaa gtatcactgg actaggaaga aggtgactta ggttctagat    2280
aggtgtcttt taggactctg attttgagga catcacttac tatccatttc ttcatgttaa    2340
aagaagtcat ctcaaactct tagtttttttt tttttacaac tatgtaattt atattccatt    2400
tacataagga tacacttatt tgtcaagctc agcacaatct gtaaattttt aacctatgtt    2460
acaccatctt cagtgccagt cttgggcaaa attgtgcaag aggtgaagtt tatatttgaa    2520
tatccattct cgttttagga ctcttcttcc atattagtgt catcttgcct ccctaccttc    2580
cacatgcccc atgacttgat gcagttttaa tacttgtaat tcccctaacc ataagattta    2640
ctgctgctgt ggatatctcc atgaagtttt cccactgagt cacatcagaa atgccctaca    2700
tcttatttcc tcagggctca agagaatctg acagatacca taaagggatt tgacctaatc    2760
actaattttc aggtggtggc tgatgctttg aacatctctt tgctgcccaa tccattagcg    2820
acagtaggat ttttcaaacc tggtatgaat agacagaacc ctatccagtg gaaggagaat    2880
ttaataaaga tagtgctgaa agaattcctt aggtaatcta taactaggac tactcctggt    2940
aacagtaata cattccattg ttttagtaac cagaaatctt catgcaatga aaaatacttt    3000
aattcatgaa gcttactttt tttttttggt gtcagagtct cgctcttgtc acccaggctg    3060
gaatgcagtg gcgccatctc agctcactgc aacctccatc tcccaggttc aagcgattct    3120
cgtgcctcgg cctcctgagt agctgggatt acaggcgtgt gccactacac tcaactaatt    3180
tttgtatttt taggagagac ggggtttcac cctgttggcc aggctggtct cgaactcctg    3240
acctcaagtg attcacccac cttggcctca taaacctgtt ttgcagaact catttattca    3300
gcaaatattt attgagtgcc taccagatgc cagtcaccgc acaaggcact gggtatatgg    3360
tatccccaaa caagagacat aatcccggtc cttaggtagt gctagtgtgg tctgtaatat    3420
cttactaagg ccttttggtat acgacccaga gataacacga tgcgtatttt agttttgcaa    3480
```

```
agaagggtt tggtctctgt gccagctcta taattgtttt gctacgattc cactgaaact    3540
cttcgatcaa gctactttat gtaaatcact tcattgtttt aaaggaataa acttgattat    3600
attgtttttt tatttggcat aactgtgatt cttttaggac aattactgta cacattaagg    3660
tgtatgtcag atattcatat tgacccaaat gtgtaatatt ccagttttct ctgcataagt    3720
aattaaaata tacttaaaaa ttaatagttt tatctgggta caaataaaca ggtgcctgaa    3780
ctagttcaca gacaaggaaa cttctatgta aaaatcacta tgatttctga attgctatgt    3840
gaaactacag atctttggaa cactgtttag gtagggtgtt aagacttaca cagtacctcg    3900
tttctcacaca gagaaagaaa tggccatact tcaggaactg cagtgcttat gaggggatat    3960
ttaggcctct tgaattttg atgtagatgg gcattttttt aaggtagtgg ttaattacct    4020
ttatgtgaac tttgaatggt ttaacaaaag atttgttttt gtagagattt taaggggga    4080
gaattctaga ataaatgtt acctaattat tacagcctta aagacaaaaa tccttgttga    4140
agtttttta aaaaaagcta aattacatag acttaggcat taacatgttt gtggaagaat    4200
atagcagacg tatattgtat catttgagtg aatgttccca agtaggcatt ctaggctcta    4260
tttaactgag tcacactgca taggaattta gaacctaact tttataggtt atcaaaactg    4320
ttgtcaccat tgcacaattt tgtcctaata tatacataga aactttgtgg ggcatgttaa    4380
gttacagttt gcacaagttc atctcatttg tattccattg attttttttt tcttctaaac    4440
attttttctt caaacagtat ataactttt ttaggggatt ttttttaga cagcaaaaac    4500
tatctgaaga tttccatttg tcaaaaagta atgatttctt gataattgtg tagtaatgtt    4560
ttttagaacc cagcagttac cttaaagctg aatttatatt tagtaacttc tgtgttaata    4620
ctggatagca tgaattctgc attgagaaac tgaatagctg tcataaaatg aaactttctt    4680
tctaaagaaa gatactcaca tgagttcttg aagaatagtc ataactagat taagatctgt    4740
gttttagttt aatagtttga agtgcctgtt tgggataatg ataggtaatt tagatgaatt    4800
tagggaaaa aaaagttatc tgcagatatg ttgagggccc atctctcccc ccacaccccc    4860
acagagctaa ctgggttaca gtgtttttatc cgaaagtttc caattccact gtcttgtgtt    4920
ttcatgttga aaatactttt gcatttttcc tttgagtgcc aatttcttac tagtactatt    4980
tcttaatgta acatgtttac ctggaatgta ttttaactat ttttgtatag tgtaaactga    5040
aacatgcaca ttttgtacat tgtgctttct tttgtgggac atatgcagtg tgatccagtt    5100
gttttccatc atttggttgc gctgacctag gaatgttggt catatcaaac attaaaaatg    5160
accactcttt taattgaaat taacttttaa atgtttatag gagtatgtgc tgtgaagtga    5220
tctaaaattt gtaatatttt tgtcatgaac tgtactactc ctaattattg taatgtaata    5280
aaatagtta cagtgacaaa aaaaaaaaaa aa                                  5312
```

<210> SEQ ID NO 2  
<211> LENGTH: 567  
<212> TYPE: DNA  
<213> ORGANISM: Homo sapiens

<400> SEQUENCE: 2

```
atgactgaat ataaacttgt ggtagttgga gctggtggcg taggcaagag tgccttgacg      60
atacagctaa ttcagaatca ttttgtggac gaatatgatc caacaataga ggattcctac     120
aggaagcaag tagtaattga tgagaaacc tgtctcttgg atattctcga cacagcaggt     180
caagaggagt acagtgcaat gagggaccag tacatgagga ctggggaggg ctttctttgt     240
```

-continued

| | |
|---|---|
| gtatttgcca taaataatac taaatcattt gaagatattc accattatag agaacaaatt | 300 |
| aaaagagtta aggactctga agatgtacct atggtcctag taggaaataa atgtgatttg | 360 |
| ccttctagaa cagtagacac aaaacaggct caggacttag caagaagtta tggaattcct | 420 |
| tttattgaaa catcagcaaa gacaagacag ggtgttgatg atgccttcta tacattagtt | 480 |
| cgagaaattc gaaaacataa agaaaagatg agcaaagatg gtaaaagaa gaaaagaag | 540 |
| tcaaagacaa agtgtgtaat tatgtaa | 567 |

<210> SEQ ID NO 3
<211> LENGTH: 188
<212> TYPE: PRT
<213> ORGANISM: Homo sapiens

<400> SEQUENCE: 3

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 4
<211> LENGTH: 4454
<212> TYPE: DNA
<213> ORGANISM: Homo Sapiens

<400> SEQUENCE: 4

| | |
|---|---|
| gaaacgtccc gtgtgggagg ggcgggtctg ggtgcggcct gccgcatgac tcgtggttcg | 60 |
| gaggcccacg tggccggggc ggggactcag gcgcctgggg cgccgactga ttacgtagcg | 120 |
| ggcgggccg gaagtgccgc tccttggtgg gggctgttca tggcggttcc ggggtctcca | 180 |
| acatttttcc cggctgtggt cctaaatctg tccaaagcag aggcagtgga gcttgaggtt | 240 |
| cttgctggtg tgaaatgact gagtacaaac tggtggtggt tggagcaggt ggtgttggga | 300 |
| aaagcgcact gacaatccag ctaatccaga accactttgt agatgaatat gatcccacca | 360 |
| tagaggattc ttacagaaaa caagtggtta tagatggtga aacctgtttg ttggacatac | 420 |
| tggatacagc tggacaagaa gagtacagtg ccatgagaga ccaatacatg aggacaggcg | 480 |

```
aaggcttcct ctgtgtattt gccatcaata atagcaagtc atttgcggat attaacctct    540
acagggagca gattaagcga gtaaaagact cggatgatgt acctatggtg ctagtgggaa    600
acaagtgtga tttgccaaca aggacagttg atacaaaaca agcccacgaa ctggccaaga    660
gttacgggat tccattcatt gaaacctcag ccaagaccag acagggtgtt gaagatgctt    720
tttacacact ggtaagagaa atacgccagt accgaatgaa aaaactcaac agcagtgatg    780
atgggactca gggttgtatg ggattgccat gtgtggtgat gtaacaagat acttttaaag    840
ttttgtcaga aaagagccac tttcaagctg cactgacacc ctggtcctga cttccctgga    900
ggagaagtat tcctgttgct gtcttcagtc tcacagagaa gctcctgcta cttccccagc    960
tctcagtagt ttagtacaat aatctctatt tgagaagttc tcagaataac tacctcctca   1020
cttggctgtc tgaccagaga atgcacctct tgttactccc tgttattttt ctgccctggg   1080
ttcttccaca gcacaaacac acctctgcca ccccaggttt ttcatctgaa aagcagttca   1140
tgtctgaaac agaaaccaa accgcaaacg tgaaattcta ttgaaaacag tgtcttgagc   1200
tctaaagtag caactgctgg tgatttttt tttcttttta ctgttgaact tagaactatg   1260 ctaattttg gagaaatgtc ataaattact gttttgccaa gaatatagtt attattgctg   1320
tttggtttgt ttataatgtt atcggctcta ttctctaaac tggcatctgc tctagattca   1380
taaatacaaa aatgaatact gaattttgag tctatcctag tcttcacaac tttgacgtaa   1440
ttaaatccaa ctttcacagt gaagtgcctt tttcctagaa gtggtttgta gacttccttt   1500
ataatatttc agtggaatag atgtctcaaa aatccttatg catgaaatga atgtctgaga   1560
tacgtctgtg acttatctac cattgaagga aagctatatc tatttgagag cagatgccat   1620
tttgtacatg tatgaaattg gttttccaga ggcctgtttt ggggcttttcc caggagaaag   1680 atgaaactga aagcacatga ataatttcac ttaataattt ttacctaatc tccactttt   1740 tcataggtta ctacctatac aatgtatgta atttgttttcc cctagcttac tgataaacct   1800
aatattcaat gaacttccat ttgtattcaa atttgtgtca taccagaaag ctctacattt   1860
gcagatgttc aaatattgta aaactttggt gcattgttat ttaatagctg tgatcagtga   1920
ttttcaaacc tcaaatatag tatattaaca aattacattt tcactgtata tcatggtatc   1980
ttaatgatgt atataattgc cttcaatccc cttctcaccc caccctctac agcttccccc   2040
acagcaatag gggcttgatt atttcagttg agtaaagcat ggtgctaatg gaccagggtc   2100
acagtttcaa aacttgaaca atccagttag catcacagag aaagaaattc ttctgcattt   2160
gctcattgca ccagtaactc cagctagtaa ttttgctagg tagctgcagt tagccctgca   2220
aggaaagaag aggtcagtta gcacaaaccc tttaccatga ctggaaaact cagtatcacg   2280
tatttaaaca ttttttttc ttttagccat gtagaaactc taaattaagc caatattctc   2340
atttgagaat gaggatgtct cagctgagaa acgttttaaa ttctctttat tcataatgtt   2400
ctttgaaggg tttaaaacaa gatgttgata aatctaagct gatgagtttg ctcaaaacag   2460
gaagttgaaa ttgttgagac aggaatggaa aatataatta attgataacct atgaggattt   2520 ggaggcttgg cattttaatt tgcagataat acccctggtaa ttctcatgaa aaatagactt   2580
ggataacttt tgataaaaga ctaattccaa aatggccact ttgttcctgt ctttaatatc   2640
taaatactta ctgaggtcct ccatcttcta tattatgaat tttcatttat taagcaaatg   2700
tcatattacc ttgaaattca gaagagaaga aacatatact gtgtccagag tataatgaac   2760
ctgcagagtt gtgcttctta ctgctaattc tgggagcttt cacagtactg tcatcatttg   2820
```

| | |
|---|---|
| taaatggaaa ttctgctttt ctgtttctgc tccttctgga gcagtgctac tctgtaatt | 2880 |
| tcctgaggct tatcacctca gtcatttctt ttttaaatgt ctgtgactgg cagtgattct | 2940 |
| ttttcttaaa aatctattaa atttgatgtc aaattaggga gaaagatagt tactcatctt | 3000 |
| gggctcttgt gccaatagcc cttgtatgta tgtacttaga gttttccaag tatgttctaa | 3060 |
| gcacagaagt ttctaaatgg ggccaaaatt cagacttgag tatgttcttt gaataccta | 3120 |
| agaagttaca attagccggg catggtggcc cgtgcctgta gtcccagcta cttgagaggc | 3180 |
| tgaggcagga gaatcacttc aacccaggag gtggaggtta cagtgagcag agatcgtgcc | 3240 |
| actgcactcc agcctgggtg acaagagaga cttgtctcca aaaaaaagt tacacctagg | 3300 |
| tgtgaatttt ggcacaaagg agtgacaaac ttatagttaa aagctgaata acttcagtgt | 3360 |
| ggtataaaac gtggttttta ggctatgttt gtgattgctg aaaagaattc tagtttacct | 3420 |
| caaaatcctt ctctttcccc aaattaagtg cctggccagc tgtcataaat tacatattcc | 3480 |
| ttttggtttt tttaaaggtt acatgttcaa gagtgaaaat aagatgttct gtctgaaggc | 3540 |
| taccatgccg gatctgtaaa tgaacctgtt aaatgctgta tttgctccaa cggcttacta | 3600 |
| tagaatgtta cttaatacaa tatcatactt attacaattt ttactatagg agtgtaatag | 3660 |
| gtaaaattaa tctctatttt agtgggccca tgtttagtct ttcaccatcc tttaaactgc | 3720 |
| tgtgaatttt tttgtcatga cttgaaagca aggatagaga aacactttag agatatgtgg | 3780 |
| ggttttttta ccattccaga gcttgtgagc ataatctcat ttgctttata tttatagtca | 3840 |
| tgaactccta agttggcagc tacaaccaag aaccaaaaaa tggtgcgttc tgcttcttgt | 3900 |
| aattcatctc tgctaataaa ttataagaag caaggaaaat tagggaaaat attttatttg | 3960 |
| gatggtttct ataaacaagg gactataatt cttgtacatt attttttcatc tttgctgttt | 4020 |
| ctttgagcag tctaatgtgc cacacaatta tctaaggtat ttgttttcta taagaattgt | 4080 |
| tttaaaagta ttcttgttac cagagtagtt gtattatatt tcaaaacgta agatgatttt | 4140 |
| taaaagcctg agtactgacc taagatgaaa ttgtatgaac tctgctctgg agggagggga | 4200 |
| ggatgtccgt ggaagttgta agacttttat ttttttgtgc catcaaatat aggtaaaaat | 4260 |
| aattgtgcaa ttctgctgtt taaacaggaa ctattggcct ccttggccct aaatggaagg | 4320 |
| gccgatattt taagttgatt attttattgt aaattaatcc aacctagttc ttttttaattt | 4380 |
| ggttgaatgt tttttcttgt taaatgatgt ttaaaaaata aaaactggaa gttcttggct | 4440 |
| tagtcataat tctt | 4454 |

<210> SEQ ID NO 5
<211> LENGTH: 570
<212> TYPE: DNA
<213> ORGANISM: Homo sapiens

<400> SEQUENCE: 5

| | |
|---|---|
| atgactgagt acaaactggt ggtggttgga gcaggtggtg ttgggaaaag cgcactgaca | 60 |
| atccagctaa tccagaacca ctttgtagat gaatatgatc ccaccataga ggattcttac | 120 |
| agaaaacaag tggttataga tggtgaaacc tgtttgttgg acatactgga tacagctgga | 180 |
| caagaagagt acagtgccat gagagaccaa tacatgagga caggcgaagg cttcctctgt | 240 |
| gtatttgcca tcaataatag caagtcattt gcggatatta acctctacag ggagcagatt | 300 |
| aagcgagtaa aagactcgga tgatgtacct atggtgctag tgggaaacaa gtgtgatttg | 360 |
| ccaacaagga cagttgatac aaaacaagcc cacgaactgg ccaagagtta cgggattcca | 420 |
| ttcattgaaa cctcagccaa gaccagacag ggtgttgaag atgcttttta cacactggta | 480 |

```
                       agagaaatac gccagtaccg aatgaaaaaa ctcaacagca gtgatgatgg gactcagggt        540
tgtatgggat tgccatgtgt ggtgatgtaa                                         570

<210> SEQ ID NO 6
<211> LENGTH: 189
<212> TYPE: PRT
<213> ORGANISM: Homo sapiens

<400> SEQUENCE: 6

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185

<210> SEQ ID NO 7
<211> LENGTH: 3159
<212> TYPE: DNA
<213> ORGANISM: Homo sapiens

<400> SEQUENCE: 7
cgctccacca gatccgcggg agccccactg ctctccgggt ccttggcttg tggctgtggg       60
tcccatcggg cccgccctcg cacgtcactc cgggacccccc gcggcctccg caggttctgc      120
gctccaggcc ggagtcagag actccaggat cggttctttc atcttcgccg cccctgcgcg      180
tccagctctt ctaagacgag atgccgtcgg gcttccaaca gataggctcc gaagatgggg      240 aacccctca gcagcgagtg actgggaccc tggtccttgc tgtgttctct gcggtgcttg       300
gctccctgca gtttgggtac aacattgggg tcatcaatgc ccctcagaag gtgattgaac      360
agagctacaa tgagacgtgg ctggggaggc aggggcctga gggacccagc tccatccctc      420
caggcaccct caccaccctc tgggccctct ccgtggccat cttttcgtg ggcggcatga       480 tttcctcctt cctcattggt atcatctctc agtggcttgg aaggaaaagg gccatgctgg      540
tcaacaatgt cctggcggtg ctgggggggca gcctcatggg cctggccaat gctgctgcct      600
cctatgaaat gctcatcctt ggacgattcc tcattggcgc ctactcaggg ctgacatcag      660
```

-continued

| | |
|---|---|
| ggctggtgcc catgtacgtg ggggagattg ctcccactca cctgcggggc gccctgggga | 720 |
| cgctcaacca actggccatt gttatcggca ttctgatcgc ccaggtgctg ggcttggagt | 780 |
| ccctcctggg cactgccagc ctgtggccac tgctcctggg cctcacagtg ctacctgccc | 840 |
| tcctgcagct ggtcctgctg cccttctgtc ccgagagccc ccgctacctc tacatcatcc | 900 |
| agaatctcga ggggcctgcc agaaagagtc tgaagcgcct gacaggctgg gccgatgttt | 960 |
| ctggagtgct ggctgagctg aaggatgaga agcggaagct ggagcgtgag cggccactgt | 1020 |
| ccctgctcca gctcctgggc agccgtaccc accggcagcc cctgatcatt gcggtcgtgc | 1080 |
| tgcagctgag ccagcagctc tctggcatca atgctgtttt ctattattcg accagcatct | 1140 |
| tcgagacagc agggggtaggc cagcctgcct atgccaccat aggagctggt gtggtcaaca | 1200 |
| cagtcttcac cttggtctcg gtgttgttgg tggagcgggc ggggcgccgg acgctccatc | 1260 |
| tcctgggcct ggcgggcatg tgtggctgtg ccatcctgat gactgtggct ctgctcctgc | 1320 |
| tggagcgagt tccagccatg agctacgtct ccattgtggc catctttggc ttcgtggcat | 1380 |
| tttttgagat tggccctggc cccattcctt ggttcatcgt ggccgagctc ttcagccagg | 1440 |
| gaccccgccc ggcagccatg gctgtggctg gtttctccaa ctggacgagc aacttcatca | 1500 |
| ttggcatggg tttccagtat gttgcggagg ctatggggcc ctacgtcttc cttctatttg | 1560 |
| cggtcctcct gctgggcttc ttcatcttca ccttcttaag agtacctgaa actcgaggcc | 1620 |
| ggacgtttga ccagatctca gctgccttcc accggacacc ctctctttta gagcaggagg | 1680 |
| tgaaacccag cacagaactt gagtatttag gccagatga gaacgactga ggggccaggc | 1740 |
| aggggtggga gagccagctc tctctacccg gcccagagac cccttccttt cctctgcagc | 1800 |
| actttaaccc tctcttccct attatttccg ggtggaaaag aatccctgca gcctggtaga | 1860 |
| attgggaagc tggggaagg gtggtctgag cacccctca ttcccctcgt gtgactctct | 1920 |
| tggattattt atgtgttgtg gtttggccgt ggccatcagg gtgggccact ctcccctccc | 1980 |
| tcttccttcc cccatcccct ttcctcccca ccttccccag actcagctcc agaatacctt | 2040 |
| cttcgctgct agagaagggg gattggaggg aagacaggtc tagactttct cagtgggaca | 2100 |
| aaccagagca gagagcagga caggagacaa gaaatccagt ttcccaccac cttggactcc | 2160 |
| tcccacaatc tgggactttc actgaattct tgccacgcag actctgggca aaggggtttt | 2220 |
| tttttttttt tttttttttt tttttgagac agtctcgctc tgtcgcccag gctcgagtgc | 2280 |
| agtggcgtga tcttgcttca ctgcaagctg tctcccaggt tcacgccatt ctcctgcctc | 2340 |
| agcctccgga gtagctggga ctacaggcgc atgccaccac acctggctaa tttattttgt | 2400 |
| atttttagta tatacgcggt ttcaccatgt tagccagaat ggtctcgatc tcctgacctc | 2460 |
| gtgatctgcc tgcctcagcc tcccaaagtg ctgggattac aggcgtgagc caccgcgcct | 2520 |
| ggcgaaggga gttctctctt gaccctgca gggaaaagga ctcacctccc tcactgcagg | 2580 |
| ctcagccttc cagggcaaga gggaacagga agtatgtgc ccatgtgtgg caagatggaa | 2640 |
| ggacggcagg ctcccgcctc taggcttggg gctctacccc gatggttccc caaggctgcc | 2700 |
| aagaaggagc cctaactttc ttcctctccc ttcctggaag ggtgctgcat ccacaggctt | 2760 |
| ttgaccaact aaggcaaaga ggggatttga aaggctgcct ggaaacactg ggctgggagg | 2820 |
| agcctttgga tattttata tacgtttgaa aaggggattg agagaagaaa ccaaaggtcg | 2880 |
| gttgtactaa atgtatatat atagatactt ctataaagtc actgctgaag acaagcatcc | 2940 |
| tattgtggag gtacttgagg atgggctgag acagggacca taactcttca cccctcttcc | 3000 |
| tccctctgtc ctgcctcagc tcaaggcctc agaatcttct ggatgccatt gctcatgccc | 3060 |

```
ctactcacat ttctactcgt tgctttatta atagtaaatg ctcaataaat tgtagctgcc    3120
agtgccgggc attgctcttg gcatttgcaa aaaaaaaa                            3159

<210> SEQ ID NO 8
<211> LENGTH: 1530
<212> TYPE: DNA
<213> ORGANISM: Homo sapiens

<400> SEQUENCE: 8
atgccgtcgg gcttccaaca gataggctcc gaagatgggg aacccctca gcagcgagtg       60 actgggaccc tggtccttgc tgtgttctct gcggtgcttg gctccctgca gtttgggtac     120
aacattgggg tcatcaatgc ccctcagaag gtgattgaac agagctacaa tgagacgtgg     180
ctggggaggc aggggcctga gggacccagc tccatccctc aggcaccct caccaccctc      240 tgggccctct ccgtggccat cttttccgtg ggcggcatga tttcctcctt cctcattggt    300
atcatctctc agtggcttgg aaggaaaagg gccatgctgg tcaacaatgt cctgcggtg    360 ctgggggca gcctcatggg cctggccaat gctgctgcct cctatgaaat gctcatcctt     420
ggacgattcc tcattggcgc ctactcaggg ctgacatcag gctggtgcc catgtacgtg      480 ggggagattg ctcccactca cctgcggggc gccctgggga cgctcaacca actggccatt    540
gttatcggca ttctgatcgc ccaggtgctg gcttggagt ccctcctggg cactgccagc     600
ctgtggccac tgctcctggg cctcacagtg ctacctgccc tcctgcagct ggtcctgctg    660
cccttctgtc ccgagagccc ccgctacctc tacatcatcc agaatctcga ggggcctgcc    720
agaaagagtc tgaagcgcct gacaggctgg gccgatgttt ctggagtgct ggctgagctg    780
aaggatgaga gcggaagct ggagcgtgag cggccactgt ccctgctcca gctcctgggc    840
agccgtaccc accggcagcc cctgatcatt gcggtcgtgc tgcagctgag ccagcagctc    900
tctggcatca atgctgtttt ctattattcg accagcatct tcgagacagc aggggtaggc    960
cagcctgcct atgccaccat aggagctggt gtggtcaaca cagtcttcac cttggtctcg   1020
gtgttgttgg tggagcgggc ggggcgccgg acgctccatc tcctgggcct ggcgggcatg   1080
tgtggctgtg ccatcctgat gactgtggct ctgctcctgc tggagcgagt tccagccatg   1140
agctacgtct ccattgtggc catctttggc ttcgtggcat ttttgagat tggccctggc    1200 cccattcctt ggttcatcgt ggccgagctc ttcagccagg acccccgccc ggcagccatg   1260
gctgtggctg gtttctccaa ctggacgagc aacttcatca ttggcatggg tttccagtat   1320
gttgcggagg ctatggggcc ctacgtcttc cttctatttg cggtcctcct gctgggcttc   1380
ttcatcttca ccttcttaag agtacctgaa actcgaggcc ggacgtttga ccagatctca   1440
gctgccttcc accggacacc ctctcttta gagcaggagg tgaaacccag cacagaactt    1500
gagtatttag ggccagatga gaacgactga                                    1530

<210> SEQ ID NO 9
<211> LENGTH: 509
<212> TYPE: PRT
<213> ORGANISM: Homo sapiens

<400> SEQUENCE: 9

Met Pro Ser Gly Phe Gln Gln Ile Gly Ser Glu Asp Gly Glu Pro Pro
1               5                   10                  15

Gln Gln Arg Val Thr Gly Thr Leu Val Leu Ala Val Phe Ser Ala Val
            20                  25                  30
```

-continued

Leu Gly Ser Leu Gln Phe Gly Tyr Asn Ile Gly Val Ile Asn Ala Pro
         35                  40                  45

Gln Lys Val Ile Glu Gln Ser Tyr Asn Glu Thr Trp Leu Gly Arg Gln
 50                  55                  60

Gly Pro Glu Gly Pro Ser Ser Ile Pro Pro Gly Thr Leu Thr Thr Leu
 65                  70                  75                  80

Trp Ala Leu Ser Val Ala Ile Phe Ser Val Gly Gly Met Ile Ser Ser
             85                  90                  95

Phe Leu Ile Gly Ile Ile Ser Gln Trp Leu Gly Arg Lys Arg Ala Met
            100                 105                 110

Leu Val Asn Asn Val Leu Ala Val Leu Gly Gly Ser Leu Met Gly Leu
        115                 120                 125

Ala Asn Ala Ala Ala Ser Tyr Glu Met Leu Ile Leu Gly Arg Phe Leu
    130                 135                 140

Ile Gly Ala Tyr Ser Gly Leu Thr Ser Gly Leu Val Pro Met Tyr Val
145                 150                 155                 160

Gly Glu Ile Ala Pro Thr His Leu Arg Gly Ala Leu Gly Thr Leu Asn
                165                 170                 175

Gln Leu Ala Ile Val Ile Gly Ile Leu Ile Ala Gln Val Leu Gly Leu
            180                 185                 190

Glu Ser Leu Leu Gly Thr Ala Ser Leu Trp Pro Leu Leu Leu Gly Leu
        195                 200                 205

Thr Val Leu Pro Ala Leu Leu Gln Leu Val Leu Leu Pro Phe Cys Pro
    210                 215                 220

Glu Ser Pro Arg Tyr Leu Tyr Ile Ile Gln Asn Leu Glu Gly Pro Ala
225                 230                 235                 240

Arg Lys Ser Leu Lys Arg Leu Thr Gly Trp Ala Asp Val Ser Gly Val
                245                 250                 255

Leu Ala Glu Leu Lys Asp Glu Lys Arg Lys Leu Glu Arg Glu Arg Pro
            260                 265                 270

Leu Ser Leu Leu Gln Leu Leu Gly Ser Arg Thr His Arg Gln Pro Leu
        275                 280                 285

Ile Ile Ala Val Val Leu Gln Leu Ser Gln Gln Leu Ser Gly Ile Asn
    290                 295                 300

Ala Val Phe Tyr Tyr Ser Thr Ser Ile Phe Glu Thr Ala Gly Val Gly
305                 310                 315                 320

Gln Pro Ala Tyr Ala Thr Ile Gly Ala Gly Val Val Asn Thr Val Phe
                325                 330                 335

Thr Leu Val Ser Val Leu Leu Val Glu Arg Ala Gly Arg Arg Thr Leu
            340                 345                 350

His Leu Leu Gly Leu Ala Gly Met Cys Gly Cys Ala Ile Leu Met Thr
        355                 360                 365

Val Ala Leu Leu Leu Leu Glu Arg Val Pro Ala Met Ser Tyr Val Ser
    370                 375                 380

Ile Val Ala Ile Phe Gly Phe Val Ala Phe Glu Ile Gly Pro Gly
385                 390                 395                 400

Pro Ile Pro Trp Phe Ile Val Ala Glu Leu Phe Ser Gln Gly Pro Arg
                405                 410                 415

Pro Ala Ala Met Ala Val Ala Gly Phe Ser Asn Trp Thr Ser Asn Phe
            420                 425                 430

Ile Ile Gly Met Gly Phe Gln Tyr Val Ala Glu Ala Met Gly Pro Tyr
        435                 440                 445

Val Phe Leu Leu Phe Ala Val Leu Leu Leu Gly Phe Phe Ile Phe Thr

```
                450                 455                 460
Phe Leu Arg Val Pro Glu Thr Arg Gly Arg Thr Phe Asp Gln Ile Ser
465                     470                 475                 480

Ala Ala Phe His Arg Thr Pro Ser Leu Leu Glu Gln Glu Val Lys Pro
                485                 490                 495

Ser Thr Glu Leu Glu Tyr Leu Gly Pro Asp Glu Asn Asp
            500                 505
```

BIOMARKERS OF RESPONSE TO PROTEASOME INHIBITORS

RELATED APPLICATIONS

This application claims priority to U.S. Provisional Application No. 61/558,474 filed on Nov. 11, 2011 and to U.S. Provisional Application No. 61/721,818 filed on Nov. 2, 2012. The entire contents of the foregoing applications are incorporated herein by reference.

SEQUENCE LISTING

This application contains a Sequence Listing which is submitted herewith in electronically readable format. The electronic Sequence Listing file was created on Jan. 28, 2015, is named "sequencelisting.txt" and has a size of 26.4 kb (27,089 bytes). The entire contents of the Sequence Listing in the electronic sequencelisting.txt file are incorporated herein by this reference.

BACKGROUND

Cells become cancerous when their genotype or phenotype alters in a way that there is uncontrolled growth that is not subject to the confines of the normal tissue environment. One or more genes is mutated, amplified, deleted, overexpressed or underexpressed. Chromosome portions can be lost or moved from one location to another. Some cancers have characteristic patterns by which genotypes or phenotypes are altered.

Many genes have mutations which are associated with cancer. Some genes have multiple sites where mutations can occur. Many cancers have mutations in and/or mis-expression of more than one gene. Gene mutations can facilitate tumor progression, tumor growth rate or whether a tumor will metastasize. Some mutations can affect whether a tumor cell will respond to therapy.

A variety of agents treat cancers. Cancers of the blood and bone marrow often are treated with steroids/glucocorticoids, imids, proteasome inhibitors and alkylating agents. Cancers of other tissues often are treated with alkylating agents, topoisomerase inhibitors, kinase inhibitors, microtubule inhibitors, angiogenesis inhibitors or other agents. Some patients respond to one therapy better than another, presenting the potential for a patient to follow multiple therapeutic routes to effective therapy. Valuable time early in a patient's treatment program can be lost pursuing a therapy which eventually is proven ineffective for that patient. Many patients cannot afford the time for trial-and-error choices of therapeutic regimens. Expedient and accurate treatment decisions lead to effective management of the disease.

SUMMARY

The present disclosure relates to prognosis and planning for treatment of solid tumors by measurement of at least one characteristic of a marker provided herein. Markers were identified in solid tumor samples from xenografts of human cancer cells by associating their characteristics, e.g., size, sequence, composition, activity or amount, with outcome of subsequent treatment of the host animal with proteasome inhibition therapy. The markers are predictive of whether there will be a favorable outcome (e.g., good response, long time-to-progression and/or long term survival) after treatment of patients with a proteasome inhibitor, such as a peptidyl boronic acid or peptidyl epoxy ketone. Testing samples comprising tumor cells to determine the presence, amounts or changes of genetic markers identifies particular patients who are expected to have a favorable outcome with treatment, e.g., with a proteasome inhibitor, e.g., a peptidyl boronic acid, and whose disease may be managed by standard or less aggressive treatment, as well as those patients who are expected have an unfavorable outcome with the treatment and may require an alternative treatment to, a combination of treatments and/or more aggressive treatment with a proteasome inhibitor to ensure a favorable outcome and/or successful management of the disease.

In one aspect, the invention provides kits useful in determination of characteristics, e.g., amounts, presence or changes, of the markers. In another aspect, the invention provides methods for determining prognosis and treatment or disease management strategies. In these aspects, the characteristic, e.g., size, sequence, composition, activity or amount of marker in a sample comprising tumor cells is measured. In one embodiment, the tumor is a solid tumor, e.g., non-hematological tumor, e.g., non-small cell lung cancer, colon cancer, pancreatic cancer, breast cancer, ovarian cancer, melanoma, head and neck carcinoma, prostate cancer or renal cell carcinoma.

In various embodiments, the characteristic, e.g., size, sequence, composition, activity or amount of marker DNA, the size, sequence, composition or amount of marker RNA and/or the size, sequence, composition, activity or amount of marker protein corresponding to a marker gene with one or more mutation, e.g., somatic mutation, described herein is measured. Useful information leading to the prognosis or treatment or disease management strategies is obtained when assays reveal information about a marker gene, e.g., whether the gene is mutated, or not, the identity of the mutation, and/or whether the RNA or protein amount of a mutated gene or genes indicates overexpression or underexpression. In one embodiment, the strategy is determined for proteasome inhibitor, e.g., peptidyl boronic acid, e.g., bortezomib (VELCADE®) or ixazomib citrate (MLN9708), therapy.

A marker gene useful to test for determination of non-hematological tumor, i.e., solid tumor, prognosis or treatment or disease management strategy, e.g., using a proteasome inhibitor, is v-Ki-ras2 Kirsten rat sarcoma viral oncogene homolog (KRAS). The marker gene includes mutations or alterations whose presence in marker DNA or whose effects, e.g., on marker RNA and/or protein characteristics, e.g., amounts, size, sequence, activity or composition, can provide information for determination of prognosis or treatment or disease management. In some embodiments, a gene or a mutant or modified form thereof useful as a marker gene, is associated with one or more markers, e.g., a DNA, an RNA and/or protein characteristic, e.g., size, sequence, composition, activity or amount, e.g., in a sample comprising tumor cells, which is different than a normal DNA, RNA and/or protein. Described herein are examples of modifications of this gene, referred to as a "marker gene" whose mutation can provide such information.

In some embodiments, a marker gene useful to test for determination of non-hematological tumor, i.e., solid tumor, prognosis or treatment or disease management strategy, e.g., using a proteasome inhibitor, is glucose transporter 4 (GLUT4).

The mutation of a marker gene of the present invention can provide information about outcome after treatment, e.g., with a proteasome inhibitor, e.g., a peptidyl boronic acid or peptidyl epoxy ketone. By examining a characteristic, e.g., size, sequence, composition, activity or amount of one or more of identified markers in a tumor, it is possible to determine which therapeutic agent, combination of agents, dosing and/or administration regimen is expected to provide a favorable outcome upon treatment. By examining the characteristic, e.g., size, sequence, composition, activity or amount of one or more of the identified markers or marker sets in a cancer, it is also possible to determine which therapeutic agent, combination of agents, dosing and/or administration regimen is less likely to provide a favorable outcome upon treatment. By examining the characteristic, e.g., size, sequence, composition, activity or amount of one or more of the identified markers, it is therefore possible to eliminate ineffective or inappropriate therapeutic agents or regimens. Importantly, these determinations can be made on a patient-by-patient basis. Thus, one can determine whether or not a particular therapeutic regimen is likely to benefit a particular patient or type of patient, and/or whether a particular regimen should be started or avoided, continued, discontinued or altered.

The present invention is directed to methods of identifying and/or selecting a cancer patient who is expected to demonstrate a favorable outcome upon administration of a therapeutic regimen, e.g., a therapeutic regimen comprising a proteasome inhibitor, such as a peptidyl boronic acid or peptidyl epoxy ketone treatment. Additionally provided are methods of identifying a patient who is expected to have an unfavorable outcome upon administration of such a therapeutic regimen. These methods typically include measuring, determining, receiving, storing or transmitting information about the characteristic, e.g., size, sequence, composition, activity or amount of one or more markers or mutation of marker gene in a patient's tumor (e.g., in a patient's cancer cells, e.g., non-hematological cancer cells, e.g., solid tumor cells), optionally comparing that to the characteristic, e.g., size, sequence, composition, activity or amount of a reference marker, and in a further embodiment, identifying or advising whether the result from the sample corresponds to a favorable outcome of a treatment regimen, e.g., a proteasome inhibitor, such as a peptidyl boronic acid or peptidyl epoxy ketone treatment regimen.

Additionally provided methods include therapeutic methods which further include the step of beginning, continuing, or commencing a therapy accordingly where the presence of a mutation in a marker gene or the characteristic, e.g., size, sequence, composition, activity or amount, of a patient's marker or markers indicates that the patient is expected to demonstrate a favorable outcome with the therapy, e.g., the proteasome inhibitor, such as a peptidyl boronic acid or peptidyl epoxy ketone, therapeutic regimen. In addition, the methods include therapeutic methods which further include the step of stopping, discontinuing, altering or halting a therapy accordingly where the presence of a mutation in a marker gene or the characteristic, e.g., size, sequence, composition, activity or amount of a patient's marker indicates that the patient is expected to demonstrate an unfavorable outcome with the treatment, e.g., with the proteasome inhibitor, such as a peptidyl boronic acid or peptidyl epoxy ketone, regimen, e.g., as compared to a patient identified as having a favorable outcome receiving the same therapeutic regimen. In another aspect, methods are provided for analysis of a patient not yet being treated with a therapy, e.g., an proteasome inhibitor, e.g., a peptidyl boronic acid or peptidyl epoxy ketone, and identification and prediction of treatment outcome based upon the presence of a mutation in a marker gene or characteristic, e.g., size, sequence, composition, activity or amount, of one or more of a patient's marker described herein. Such methods can include not being treated with the therapy, e.g., proteasome inhibitor, e.g., a peptidyl boronic acid or peptidyl epoxy ketone therapy, being treated with therapy, e.g., proteasome inhibitor, being treated with a peptidyl boronic acid or peptidyl epoxy ketone therapy in combination with one more additional therapies, being treated with an alternative therapy to a proteasome inhibitor, such as a peptidyl boronic acid or peptidyl epoxy ketone therapy, or being treated with a more aggressive dosing and/or administration regimen of a therapy, e.g., proteasome inhibitor, e.g., a peptidyl boronic acid or peptidyl epoxy ketone inhibitor, e.g., as compared to the dosing and/or administration regimen of a patient identified as having a favorable outcome to standard proteasome inhibitor, e.g., a peptidyl boronic acid or peptidyl epoxy ketone therapy. Thus, the provided methods of the invention can eliminate ineffective or inappropriate use of therapy, e.g., proteasome inhibitor, e.g., peptidyl boronic acid or peptidyl epoxy ketone therapy regimens.

Additional methods include methods to determine the activity of an agent, the efficacy of an agent, or identify new therapeutic agents or combinations. Such methods include methods to identify an agent as useful, e.g., as a proteasome inhibitor, e.g., a peptidyl boronic acid or peptidyl epoxy ketone, for treating a cancer, e.g., a non-hematological cancer, i.e., a solid tumor cancer (e.g., non-small cell lung cancer, colon cancer, pancreatic cancer, breast cancer, ovarian cancer, melanoma, head and neck carcinoma, prostate cancer or renal cell carcinoma), based on its ability to affect the presence of a mutation in a marker gene or characteristic, e.g., size, sequence, composition, activity or amount of a marker or markers of the invention. In some embodiments, an inhibitor which decreases or increases the presence of a mutation in a marker gene or characteristic, e.g., size, sequence, composition, activity or amount of a marker or markers provided (i.e., in a cell population, the inhibitor selects against cells comprising the mutation characteristic or selects for cells comprising the mutation or characteristic, respectively) in a manner that indicates favorable outcome of a patient having cancer would be a candidate agent for the cancer. In another embodiment, an agent which is able to decrease the viability of a tumor cell comprising a marker indicative of an unfavorable outcome would be a candidate agent for the cancer.

The present invention is also directed to methods of treating a cancer patient, with a therapeutic regimen, e.g., a proteasome inhibitor, e.g., a peptidyl boronic acid or peptidyl epoxy ketone therapy regimen (e.g., alone, or in combination with an additional agent such as a chemotherapeutic agent, e.g., a glucocorticoid agent, a microtubule inhibitor, an alkylating agent, a kinase inhibitor or a topoisomerase inhibitor), which includes the step of selecting for treatment a patient whose marker characteristic, e.g., size, sequence, composition, activity or amount indicates that the patient is expected to have a favorable outcome with the therapeutic regimen, and treating the patient with the therapy, e.g., proteasome inhibitor, e.g., a peptidyl boronic acid therapy. In some embodiments, the method can include the step of selecting a patient whose marker characteristic, e.g., size, sequence, composition, activity or amount or amounts indicates that the patient is expected to have a favorable outcome and administering a therapy other than a proteasome inhibitor therapy that demonstrates similar expected progression-free survival times as the proteasome inhibitor, e.g., a peptidyl boronic acid therapy.

Additional methods of treating a cancer patient include selecting patients that are unlikely to experience a favorable outcome upon treatment with a cancer therapy (e.g., proteasome inhibitor, e.g., a peptidyl boronic acid or peptidyl epoxy ketone therapy). Such methods can further include one or more of: administering a higher dose or increased dosing schedule of a therapy, e.g., proteasome inhibitor, e.g., a peptidyl boronic acid or peptidyl epoxy ketone as compared to the dose or dosing schedule of a patient identified as having a favorable outcome with standard therapy; administering a cancer therapy other than a proteasome inhibitor, e.g., a peptidyl boronic acid or peptidyl epoxy ketone therapy; administering a proteasome inhibitor, e.g., a peptidyl boronic acid or peptidyl epoxy ketone agent in combination with an additional agent such as a chemotherapeutic agent, e.g., a glucocorticoid agent, a microtubule inhibitor, an alkylating agent, a kinase inhibitor or a topoisomerase inhibitor. Further provided are methods for selection of a patient having aggressive disease which is expected to demonstrate more rapid time to progression or short term survival.

Additional methods include a method to evaluate whether to treat or pay for the treatment of cancer, e.g., non-hematological cancer, i.e., solid tumor cancer (e.g., non-small cell lung cancer, colon cancer, pancreatic cancer, breast cancer, ovarian cancer, melanoma, head and neck carcinoma, prostate cancer or renal cell carcinoma) by reviewing the amount of a patient's marker or markers for indication of outcome to a cancer therapy, e.g., a proteasome inhibitor, e.g., a peptidyl boronic acid or peptidyl epoxy ketone therapy regimen, and making a decision or advising on whether payment should be made.

The entire contents of all publications, patent applications, patents and other references mentioned herein are incorporated by reference.

Other features and advantages of the invention will be apparent from the following detailed description, drawings and from the claims.

DRAWINGS

FIG. 1. Correlation of mutation status of KRAS to sensitivity of tumor xenografts to MLN2238.

FIG. 2. Antitumor activity of MLN2238 in representative xenografts in comparison with vehicle control. A. PHTX132Lu primary NSCLC xenograft (wild type KRAS), B. HCT-116 xenograft (mutant KRAS).

FIG. 3. Antitumor activity of MLN2238 in xenografts of isogenic SW48 cell lines. A. SW48 xenograft (wild type KRAS), B. SW48-KrasG13D xenograft (recombinantly mutated KRAS-G13D), C. SW48-KrasG12V xenograft (recombinantly mutated KRAS-G12V).

FIG. 4. Western blot of GLUT4 protein from KRAS wild type and mutant cells. FIG. 4A, GLUT4 levels in cells grown in vitro; FIG. 4B, GLUT4 levels in tumor xenografts.

DETAILED DESCRIPTION

One of the continued problems with therapy in cancer patients is individual differences in response to therapies. While advances in development of successful cancer therapies progress, only a subset of patients respond to any particular therapy. With the narrow therapeutic index and the toxic potential of many available cancer therapies, such differential responses potentially contribute to patients undergoing unnecessary, ineffective and even potentially harmful therapy regimens. If a designed therapy could be optimized to treat individual patients, such situations could be reduced or even eliminated. Furthermore, targeted designed therapy may provide more focused, successful patient therapy overall. Accordingly, there is a need to identify particular cancer patients who are expected to have a favorable outcome when administered particular cancer therapies as well as particular cancer patients who may have a favorable outcome using more aggressive and/or alternative cancer therapies, e.g., alternative to previous cancer therapies administered to the patient. It would therefore be beneficial to provide for the diagnosis, staging, prognosis, and monitoring of cancer patients, including, e.g., non-hematological cancer patients, e.g., patients with solid tumors (e.g., non-small cell lung cancer, colon cancer, pancreatic cancer, breast cancer, ovarian cancer, melanoma, head and neck carcinoma, prostate cancer or renal cell carcinoma) who would benefit from particular cancer inhibition therapies as well as those who would benefit from a more aggressive and/or alternative cancer inhibition therapy, e.g., alternative to a cancer therapy or therapies the patient has received, thus resulting in appropriate preventative measures.

The present invention is based, in part, on the recognition that mutation of a marker gene can be associated with sensitivity of a cell comprising the mutated gene to a proteasome inhibitor, e.g., a peptidyl boronic acid. In some embodiments, the marker gene is involved in the Rat Sarcoma (RAS) signaling pathway, e.g., a gene whose mutation enables activation of the pathway. RAS is an oncogenic GTPase whose active GTP-bound state activates pathways (e.g., the mitogen-activated protein (MAP) kinase cascade) involved in tumorigenesis. Proteins, including tumor suppressors, facilitate hydrolysis of RAS-bound GTP to GDP to inactivate RAS and thus limit the signaling from a RAS oncogene. A mutation in a gene involved in this checkpoint, either in an oncogene upstream of RAS (e.g., p210BCR-ABL or erbB), in a RAS oncogene (e.g., HRAS, KRAS or NRAS), in a RAS-associated tumor suppressor (neurofibromatosis 1 (NF1)), and/or in a GTPase-activating protein (e.g., RASGAP), can enable activation of RAS signaling pathways. A protein encoded by a marker gene for sensitivity to a proteasome inhibitor can be a RAS protein. KRAS is an example of a marker gene. In the GTP-bound state of RAS proteins, e.g., NRAS, HRAS and KRAS, the RAS signaling occurs, and in the GDP-bound state, the signaling is abrogated. A mutated RAS protein can prolong its time in the GTP-bound state and the resulting signaling pathway activation can lead to proliferation of cells harboring the mutated gene. A marker gene can exhibit one or more mutations, e.g., somatic mutations, whose presence can affect expression or activity of the encoded gene product. In some embodiments, there can be more than one mutation in a marker gene in a tumor cell or tumor. In additional embodiments, there can be marker gene mutations in cells which have mutations in one or more additional genes, including mutations that can lead to tumorigenesis, but the additional mutated gene(s) may not be a marker gene as considered herein. In some embodiments, the mutation is an activating mutation. In other embodiments, the mutation affects the expression of the marker gene. In other embodiments, a mutation can result in an altered interaction of the encoded gene product with a cellular binding partner.

In one aspect, the invention provides a method for determining whether to treat with a proteasome inhibitor a patient having a solid tumor selected from the group consisting of a lung tumor and a colon tumor, the method comprising the steps of: a) measuring at least one characteristic of at least one marker associated with at least one marker gene in a patient sample comprising tumor cells, wherein one marker gene is v-Ki-ras2 Kirsten rat sarcoma viral oncogene homolog (KRAS); b) identifying whether the at least one characteristic measured in step a) is informative for outcome of treatment with the proteasome inhibitor; and c) determining to treat the patient with the proteasome inhibitor if the informative characteristic indicates that the tumor cells comprise wild type KRAS. In some embodiments, the method comprises determining to treat the patient with a proteasome inhibitor if the informative characteristic indicates that the tumor cells comprise wild type KRAS or KRAS with a mutation at codon 146. In some embodiments, the method to determine whether to treat with a proteasome inhibitor is performed in vitro.

In another aspect, the invention provides a method for determining whether to continue proteasome inhibitor treatment of a solid tumor in a patient comprising: a) treating a patient having a solid tumor with a proteasome inhibitor; b) obtaining a sample comprising tumor cells from the patient; c) measuring at least one characteristic of at least one marker associated with at least one marker gene in the sample, wherein at least one marker gene is KRAS; d) comparing the results of the measurements in c) to a reference; and e) determining to continue treatment with the proteasome inhibitor if the comparison indicates that the solid tumor cells in the sample comprise wild type KRAS; wherein the patient has a solid tumor selected from the group consisting of a lung tumor and a colon tumor. In some embodiments, the method comprises determining to continue to treat the patient with a proteasome inhibitor if the if the comparison indicates that the solid tumor cells comprise wild type KRAS or KRAS with a mutation at codon 146. In some embodiments, the method to determine whether to continue to treat with a proteasome inhibitor is performed in vitro.

In another aspect, the invention provides a kit comprising a stabilizer to add to a sample comprising tumor cells and a reagent to measure at least one characteristic of at least one marker in a sample, wherein the result of the measurement indicates whether there is a mutation in at least one marker gene, wherein at least one marker gene is KRAS.

In another aspect, the invention provides a kit comprising at least two reagents to measure at least one characteristic of at least two markers in a sample, wherein the result of the measurement indicates whether there is a mutation in at least one marker gene, wherein at least one marker gene is KRAS and wherein the sample comprises solid tumor cells wherein the solid tumor cells are selected from the group consisting of lung tumor cells and a colon tumor cells.

In another aspect, the invention provides a method for predicting sensitivity of a solid tumor cell to a proteasome inhibitor, comprising: a) assessing whether the cell expresses mutated KRAS; and b) predicting sensitivity of the cell to a proteasome inhibitor, wherein expression of mutated KRAS is predictive of poor sensitivity to the proteasome inhibitor, wherein the solid tumor cell is selected from the group consisting of a lung tumor cell and a colon tumor cell. In one embodiment, the mutated KRAS does not have a mutated codon 146.

In another aspect, the invention provides a method for treating a patient having a solid tumor comprising wild type KRAS status, comprising the step of administering to the patient a therapeutically effective amount of a proteasome inhibitor, wherein the solid tumor is selected from the group consisting of a lung tumor and a colon tumor. In one embodiment, the solid tumor comprises wild type KRAS or KRAS with mutated codon 146.

In another aspect, the invention provides the use of a proteasome inhibitor in the manufacture of a medicament to treat a solid tumor selected from the group consisting of a lung tumor and a colon tumor, wherein the solid tumor has a wild type KRAS. In one embodiment, the solid tumor has wild type KRAS or KRAS with mutated codon 146.

In another aspect, the invention provides the use of a proteasome inhibitor for treating a lung tumor or a colon tumor in a patient whose lung tumor or colon tumor has wild type KRAS. In one embodiment, the tumor has wild type KRAS or KRAS with mutated codon 146.

In another aspect, the invention provides a method for identifying a proteasome inhibitor as suitable for use in treating a patient with a non-hematological cancer, comprising: a) contacting a tumor cell in a xenograft comprising at least one mutation in at least one marker gene with a test proteasome inhibitor, wherein at least one marker gene is KRAS; b) assessing the effect of the test proteasome inhibitor on the viability of the cell; and c) determining that the test proteasome inhibitor is suitable for use in treating a patient with a non-hematological cancer if it decreases the viability of the cell. In one embodiment, the mutation is not at codon 146 of KRAS.

In another aspect, the invention provides a method for paying for the treatment of cancer with a proteasome inhibitor comprising: a) recording whether KRAS is mutated, in a sample comprising solid tumor cells from a patient, wherein the patient has lung cancer or colon cancer, and b) authorizing payment of the proteasome inhibitor treatment if KRAS is wild type. In one embodiment, the method comprises authorizing payment if KRAS is wild type or mutated at codon 146.

A method of identifying a non-hematological cancer patient who will be nonresponsive to treatment with a proteasome inhibitor, comprising determining the presence or absence of at least one KRAS mutation in a sample comprising tumor cells from the patient, wherein the patient has a non-hematological cancer selected from the group consisting of lung cancer and colon cancer, whereby the presence of at least one KRAS mutation indicates that the patient will not respond to the proteasome inhibitor. In one embodiment, the mutation is not in codon 146.

In another aspect, the invention provides a method of identifying a non-hematological cancer patient who will have a favorable outcome to treatment with a proteasome inhibitor, comprising determining the presence or absence of at least one KRAS mutation in a sample comprising tumor cells from the patient, wherein the patient has a non-hematological cancer selected from the group consisting of lung cancer and colon cancer, whereby the presence of wild type KRAS or a mutation in codon 146 indicates that the patient will respond to the proteasome inhibitor.

In some embodiments, the mutation is identified by measuring in the tumor cells, or in an extract prepared therefrom, a characteristic of a marker associated with the KRAS marker gene. In some embodiments, the method comprises determining the tumor cell KRAS sequence.

An additional embodiment of the present invention is based on the identification, in a tumor cell or tumor, whose sensitivity or resistance to a proteasome inhibitor is correlated to a mutational status of a RAS marker gene, of an additional marker gene, a glucose transporter, e.g., GLUT4. In one embodiment, a characteristic, e.g., composition, activity or amount, e.g., expression, in a tumor cell or tumor, of a glucose transporter, e.g., GLUT4, can be correlated to a mutational status or characteristic, e.g., size, sequence, composition, activity or amount, of the KRAS marker gene. In some embodiments, a glucose transporter marker characteristic correlated with sensitivity to a proteasome inhibitor is amount. In some embodiments, a glucose transporter marker, e.g., mRNA or protein, has an informative characteristic amount of low or normal expression in a tumor cell whose RAS marker gene has a mutational status which is indicative of a favorable outcome upon treatment of the tumor with a proteasome inhibitor. In some embodiments, a glucose transporter marker, e.g., mRNA or protein, has an informative characteristic of low or normal expression in a tumor cell which has an informative characteristic of expression of wild type KRAS. In one embodiment, a method of the invention includes the steps of identifying the KRAS mutational status and measuring the expression of GLUT4. In some embodiments, a patient whose tumor, e.g., a solid tumor, comprises wild type KRAS and low or normal GLUT4 expression is predicted to have a favorable outcome of treatment with a proteasome inhibitor, e.g., a peptidyl boronic acid or a peptidyl epoxy ketone. In another embodiment, a patient whose tumor, e.g., a solid tumor, comprises mutant KRAS and high, higher than normal, or higher than a reference level of GLUT4 expression is predicted to have an unfavorable outcome of treatment with a proteasome inhibitor, e.g., a peptidyl boronic acid or a peptidyl epoxy ketone.

The identification and/or measurement of a mutation in a marker gene or characteristic of a marker can be used to determine whether a favorable outcome can be expected by treatment of a tumor, e.g., with a proteasome inhibitor, e.g., a peptidyl boronic acid or peptidyl epoxy ketone therapy or whether an alternative therapy to and/or a more aggressive therapy with, e.g., a proteasome inhibitor, e.g., a peptidyl boronic acid or peptidyl epoxy ketone inhibitor may enhance the response. For example, the compositions and methods provided herein can be used to determine whether a patient is expected to have a favorable outcome to a proteasome inhibitor, e.g., a peptidyl boronic acid or peptidyl epoxy ketone therapeutic agent dosing or administration regimen. Based on these identifications, the present invention provides, without limitation: 1) methods and compositions for determining whether a proteasome inhibitor, e.g., a peptidyl boronic acid or peptidyl epoxy ketone therapy regimen will or will not be effective to achieve a favorable outcome and/or manage the cancer; 2) methods and compositions for monitoring the effectiveness of a proteasome inhibitor, e.g., a peptidyl boronic acid or peptidyl epoxy ketone therapy (alone or in a combination of agents) and dosing and administrations used for the treatment of tumors; 3) methods and compositions for treatments of tumors comprising, e.g., proteasome inhibitor, e.g., a peptidyl boronic acid or peptidyl epoxy ketone inhibition therapy regimen; 4) methods and compositions for identifying specific therapeutic agents and combinations of therapeutic agents as well as dosing and administration regimens that are effective for the treatment of tumors in specific patients; and 5) methods and compositions for identifying disease management strategies.

Proteasome inhibition represents an important strategy in cancer treatment. The proteasome is a multi-enzyme complex present in all cells which play a role in degradation of proteins involved in regulation of the cell cycle. For example, King et al. (*Science* 274:1652-1659 (1996)) demonstrated that the ubiquitin-proteasome pathway plays an essential role in regulating cell cycle, neoplastic growth and metastasis. A number of key regulatory proteins, including p53, cyclins, and the cyclin-dependent kinases p21 and p27$^{KIP1}$, are temporally degraded during the cell cycle by the ubiquitin-proteasome pathway. The ordered degradation of these proteins is required for the cell to progress through the cell cycle and to undergo mitosis. Furthermore, the ubiquitin-proteasome pathway is required for transcriptional regulation. Palombella et al. (International Patent Application Publication No. WO 95/25533) teach that the activation of the transcription factor NF-κB is regulated by proteasome-mediated degradation of the inhibitor protein IκB. In turn, NF-κB plays a central role in the regulation of genes involved in the immune and inflammatory responses. For example, Read et al. (*Immunity* 2:493-506 (1995)) demonstrated that the ubiquitin-proteasome pathway is required for expression of cell adhesion molecules, such as E-selectin, ICAM-1, and VCAM-1. Additional findings further support the role for proteasome inhibition in cancer therapy, as Zetter (*Seminars in Cancer Biology* 4:219-229 (1993)) found that cell adhesion molecules are involved in tumor metastasis and angiogenesis in vivo, by directing the adhesion and extravasation of tumor cells to and from the vasculature to distant tissue sites within the body. Moreover, Beg and Baltimore (*Science* 274:782 (1996)) found that NF-κB is an anti-apoptotic factor, and inhibition of NF-κB activation makes cells more sensitive to environmental stress and cytotoxic agents. Bortezomib (Velcade®) is a first-in-class peptidyl boronic acid proteasome inhibitor.

As used herein, the term "proteasome" refers to a subcellular complex which participates in protein homeostasis by degrading proteins no longer needed by a cell or defective proteins and which are targeted for degradation by being tagged with ubiquitin or a ubiquitin-like protein. The proteasome comprises a core complex with proteases which mediate the protein degradation.

As used herein, the term "proteasome inhibitor" refers to any substance which directly inhibits enzymatic activity of the 20S or 26S proteasome in vitro or in vivo. Proteasome inhibitors, their pharmacological properties and use in treating disease, including oncological diseases and inflammatory diseases are reviewed in Ruggeri et al. (2009) *Adv. Pharmacol.* 57:91-135. In some embodiments, the proteasome inhibitor is a peptidyl boronic acid. Examples of peptidyl boronic acid proteasome inhibitors suitable for use in the methods of the invention are disclosed in Adams et al., U.S. Pat. No. 5,780,454 (1998), U.S. Pat. No. 6,066,730 (2000), U.S. Pat. No. 6,083,903 (2000); U.S. Pat. No. 6,297,217 (2001), U.S. Pat. No. 6,465,433 (2002), U.S. Pat. No. 6,548,668 (2003), U.S. Pat. No. 6,617,317 (2003), and U.S. Pat. No. 6,747,150 (2004), each of which is hereby incorporated by reference in its entirety, including all compounds and formulae disclosed therein. In some embodiments, the peptidyl boronic acid proteasome inhibitor is selected from the group consisting of: N (4 morpholine)carbonyl-β-(1-naphthyl)-L-alanine-L-leucine boronic acid; N (8 quinoline)sulfonyl-β-(1-naphthyl)-L-alanine-L-alanine-L-leucine boronic acid; N (pyrazine)carbonyl-L-phenylalanine-L-leucine boronic acid, and N (4 morpholine)¬ carbonyl-[O-(2-pyridylmethyl)]-L-tyrosine-L-leucine boronic acid. In one embodiment, the proteasome inhibitor is N (pyrazine)carbonyl-L-phenylalanine-L-leucine boronic acid (bortezomib; VELCADE®; formerly known as MLN341 or PS-341). In another embodiment, the proteasome inhibitor is disclosed in U.S. Pat. No. 7,442,830, for example, [(1R)-1({[(2,4-dichlorobenzoyl)amino] acetyl{-amino)-3-methylbutyl]boronic acid (MLN2238) or a boronate ester thereof, e.g., a citrate ester thereof, e.g., as disclosed in PCT Publication No. WO2009154737 (ixazomib citrate, MLN9708). Ixazomib citrate, e.g., MLN9708, which can be administered orally, has anti-tumor activity in a range of hematological and solid tumor xenograft models (Kupperman et al. (2010) *Cancer Res.* 70:1970-1980). MLN9708 is a citrate ester, which rapidly hydrolyzes to the active form, MLN2238 upon exposure to aqueous solution or plasma. In another embodiment, the peptide boronic acid is disclosed in U.S. Pat. No. 7,915,236, for example [(1R)-1-[[(2S,3R)-3-hydroxy-2-[(6-phenyl-pyridine-2-carbonyl)amino]-1-oxo-butyl]amino]-3-methylbutyl]boronic acid (delanzomib). The entire contents of each of the foregoing patent publications are incorporated herein by reference.

Further examples of peptidyl boronic acid proteasome inhibitors are disclosed in Fleming and Li, International Patent Publications WO 2010/036357 and WO 2011/123502, both of which are herein incorporated by reference in their entirety, including all compounds and formulae disclosed therein.

In some embodiments, proteasome inhibitor is characterized by a compound of formula (I):

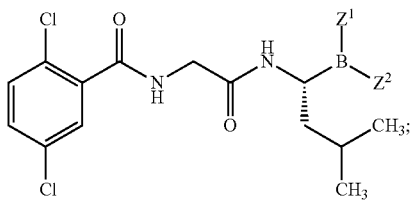

(I)

or a pharmaceutically acceptable salt or a pharmaceutical composition or a boronic acid anhydride thereof, wherein:

$Z^1$ and $Z^2$ are each independently hydroxy, alkoxy, aryloxy, or aralkoxy; or $Z^1$ and $Z^2$ together form a moiety derived from a boronic acid complexing agent.

As used herein, the term "boronic acid" refers to a chemical compound containing a —$B(OH)_2$ moiety. In some embodiments, boronic acid compounds can form oligomeric anhydrides by dehydration of the boronic acid moiety. For example, Snyder et al., *J. Am. Chem. Soc.* 80:3611 (1958), reports oligomeric arylboronic acids.

As used herein, the term "boronic acid anhydride" refers to a chemical compound formed by combination of two or more molecules of a boronic acid compound, with loss of one or more water molecules. When mixed with water, the boronic acid anhydride compound is hydrated to release the free boronic acid compound. In various embodiments, the boronic acid anhydride can comprise two, three, four, or more boronic acid units, and can have a cyclic or linear configuration. Non-limiting examples of oligomeric boronic acid anhydrides of peptide boronic acids compound of the invention are illustrated below:

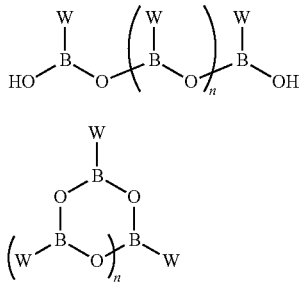

In formulae (1) and (2) directly above, the variable n is an integer from 0 to about 10, preferably 0, 1, 2, 3, or 4. In some embodiments, the boronic acid anhydride compound comprises a cyclic trimer ("boroxine") of formula (2), wherein n is 1. The variable W has the formula (3):

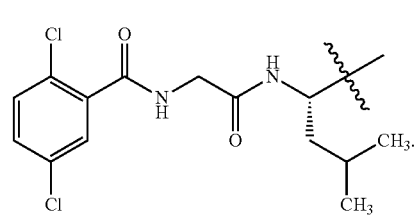

In some embodiments, at least 80% of the boronic acid present in the boronic acid anhydride compound exists in a single oligomeric anhydride form. In some embodiments, at least 85%, 90%, 95%, or 99% of the boronic acid present in the boronic acid anhydride compound exists in a single oligomeric anhydride form. In certain preferred embodiments, the boronic acid anhydride compound consists of, or consists essentially of, a boroxine having formula (3).

The boronic acid anhydride compound preferably can be prepared from the corresponding boronic acid by exposure to dehydrating conditions, including, but not limited to, recrystallization, lyophilization, exposure to heat, and/or exposure to a drying agent. Nonlimiting examples of suitable recrystallization solvents include ethyl acetate, dichloromethane, hexanes, ether, acetonitrile, ethanol, and mixtures thereof.

In some embodiments, $Z^1$ and $Z^2$ together form a moiety derived from a boronic acid complexing agent as disclosed in Olhava and Danca, U.S. Pat. Nos. 7,442,830, 7,867,662, and 8,003,819 all of which are herein incorporated by reference in their entirety. For purposes of the invention, the term "boronic acid complexing agent" refers to any compound having at least two functional groups, each of which can form a covalent bond with boron. Nonlimiting examples of suitable functional groups include amino, hydroxyl, and carboxyl. In some embodiments, at least one of the functional groups is a hydroxyl group. The term "moiety derived from a boronic acid complexing agent" refers to a moiety formed by removing the hydrogen atoms from two functional groups of a boronic acid complexing agent.

As used herein, the terms "boronate ester" and "boronic ester" are used interchangeably and refer to a chemical compound containing a —$B(Z^1)(Z^2)$ moiety, wherein at least one of $Z^1$ or $Z^2$ is alkoxy, aralkoxy, or aryloxy; or $Z^1$ and $Z^2$ together form a moiety derived from a boronic acid complexing agent having at least one hydroxyl group.

In some embodiments, $Z^1$ and $Z^2$ are each hydroxy and the compound of formula (I) is characterized by formula (II):

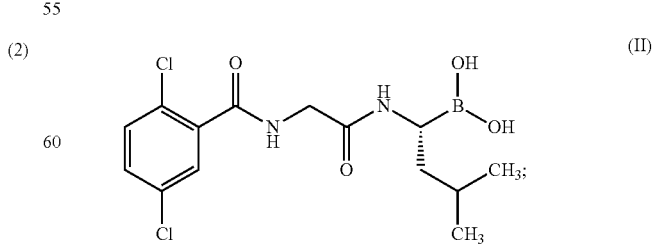

or a pharmaceutically acceptable salt or a pharmaceutical composition or a boronic acid anhydride thereof.

The compound of formula (II), [(1R)-1-({[(2,4-dichlorobenzoyl)amino]acetyl{-amino)-3-methylbutyl]boronic acid (MLN2238) is disclosed in Olhava and Danca, U.S. Pat. No. 7,442,830, herein incorporated by reference in its entirety.

In some other embodiments, $Z^1$ and $Z^2$ together form a moiety derived from a compound having at least two hydroxyl groups separated by at least two connecting atoms in a chain or ring, said chain or ring comprising carbon atoms and, optionally, a heteroatom or heteroatoms which can be N, S, or O, wherein the atom attached to boron in each case is an oxygen atom.

As employed herein, the term "compound having at least two hydroxyl groups" refers to any compound having two or more hydroxyl groups. For purposes of the invention, the two hydroxyl groups preferably are separated by at least two connecting atoms, preferably from about 2 to about 5 connecting atoms, more preferably 2 or 3 connecting atoms. For convenience, the term "dihydroxy compound" may be used to refer to a compound having at least two hydroxyl groups, as defined above. Thus, as employed herein, the term "dihydroxy compound" is not intended to be limited to compounds having only two hydroxyl groups. The moiety derived from a compound having at least two hydroxyl groups may be attached to boron by the oxygen atoms of any two of its hydroxyl groups. Preferably, the boron atom, the oxygen atoms attached to boron, and the atoms connecting the two oxygen atoms together form a 5- or 6-membered ring.

For purposes of the present invention, the boronic acid complexing agent preferably is pharmaceutically acceptable, i.e., suitable for administration to humans. In some preferred embodiments, the boronic acid complexing agent is a sugar, as described, e.g., in Plamondon et al., WO 02/059131 and Gupta et al., WO 02/059130. The term "sugar" includes any polyhydroxy carbohydrate moiety, including monosaccharides, disaccharides, polysaccharides, sugar alcohols and amino sugars. In some embodiments, the sugar is a monosaccharide, disaccharide, sugar alcohol, or amino sugar. Non-limiting examples of suitable sugars include glucose, sucrose, fructose, trehalose, mannitol, sorbitol, glucosamine, and N-methylglucosamine. In certain embodiments, the sugar is mannitol or sorbitol. Thus, in the embodiments wherein the sugar is mannitol or sorbitol, $Z^1$ and $Z^2$ together form a moiety of formula $C_6H_{12}O_6$, wherein the oxygen atoms of the two deprotonated hydroxyl groups form covalent attachments with boron to form a boronate ester compound. In certain embodiments, $Z^1$ and $Z^2$ together form a moiety derived from D-mannitol as disclosed in U.S. Pat. No. 7,442,830, herein incorporated by reference in its entirety.

In some embodiments, the boronic acid complexing agent is an alpha-hydroxycarboxylic acid or a beta-hydroxycarboxylic acid, as described, e.g., in Elliott et al., WO 09/154737, herein incorporated by reference in its entirety. In some embodiments, the boronic acid complexing agent is selected from the group consisting of glycolic acid, malic acid, hexahydromandelic acid, citric acid, 2-hydroxyisobutyric acid, 3-hydroxybutyric acid, mandelic acid, lactic acid, 2-hydroxy-3,3-dimethylbutyric acid, 2-hydroxy-3-methylbutyric acid, 2-hydroxyisocaproic acid, beta-hydroxyisovaleric acid, salicylic acid, tartaric acid, benzilic acid, glucoheptonic acid, maltonic acid, lactobionic acid, galactaric acid, embonic acid, 1-hydroxy-2-naphthoic acid, and 3-hydroxy-2-naphthoic acid. In certain embodiments, the boronic acid complexing agent is citric acid.

In certain embodiments, wherein the alpha-hydroxy carboxylic acid or beta-hydroxy carboxylic acid is citric acid, the compound of formula (I) is characterized by formula (III-A) or (III-B):

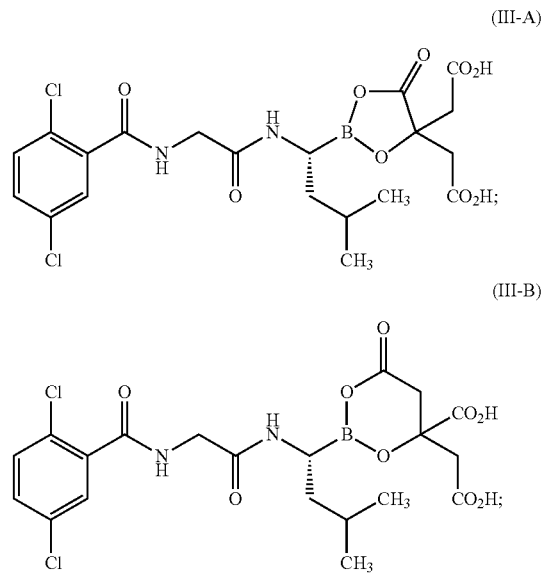

(III-A)

(III-B)

or a mixture thereof or a pharmaceutical composition thereof.

In certain embodiments, wherein the alpha-hydroxy carboxylic acid or beta-hydroxy carboxylic acid is citric acid, the compound of formula (I) is characterized by formula (III-A):

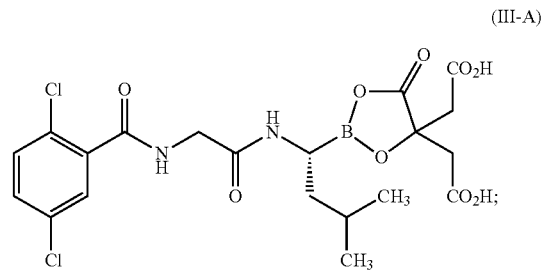 [SMILES: CC(C)C[C@H](NC(=O)CNC(=O)c1cc(Cl)ccc1Cl)B1OC(=O)C(CC(=O)O)(CC(=O)O)O1]

(III-A)

or a pharmaceutical composition thereof.

The compound of formula (III-A), 2,2'-{2-[(1R)-1-({[(2,5dichlorobenzoyl)amino]acetyl}amino)-3-methylbutyl]-5-oxo-1,3,2-dioxaborolane-4,4-diyl}diacetic acid (MLN9708, ixazomib citrate) is disclosed in Elliott et al., WO 09/154737, herein incorporated by reference in its entirety.

Additionally, proteasome inhibitors include peptide aldehyde proteasome inhibitors (Stein et al., U.S. Pat. No. 5,693,617 (1997); Siman et al., international patent publication WO 91/13904; Iqbal et al., J. Med. Chem. 38:2276-2277 (1995); and Iinuma et at, international patent publication WO 05/105826, each of which is hereby incorporated by reference in its entirety), peptidyl epoxy ketone proteasome inhibitors (Crews et at, U.S. Pat. No. 6,831,099; Smyth et al., international patent publication WO 05/111008; Bennett et al., international patent publication WO 06/045066 or U.S. Patent Application publication No. US20050245435, e.g., (S)-4-Methyl-N—((S)-1-(((S)-4-methyl-1-((R)-2- methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (carfilzomib); Spaltenstein et al. *Tetrahedron Lett.* 37:1343 (1996); Meng, *Proc. Natl. Acad. Sci.* 96: 10403 (1999); and Meng, *Cancer Res.* 59: 2798 (1999)), alpha-ketoamide proteasome inhibitors (Chatterjee and Mallamo, U.S. Pat. No. 6,310,057 (2001) and U.S. Pat. No. 6,096,778 (2000); and Wang et al., U.S. Pat. No. 6,075,150 (2000) and U.S. Pat. No. 6,781,000 (2004)), peptidyl vinyl ester proteasome inhibitors (Marastoni et al., *J. Med. Chem.* 48:5038 (2005), and peptidyl vinyl sulfone and 2-keto-1,3,4-oxadiazole proteasome inhibitors, such as those disclosed in Rydzewski et al., *J. Med. Chem.* 49:2953 (2006); and Bogyo et al., *Proc. Natl. Acad. Sci.* 94:6629 (1997)), azapeptoids and (Bouget et al., *Bioorg. Med. Chem.* 11:4881 (2003); Baudy-Floc'h et al., international patent publication WO 05/030707; and Bonnemains et al., international patent publication WO 03/018557), efrapeptin oligopeptides (Papathanassiu, international patent publication WO 05/115431), lactacystin and salinosporamide and analogs thereof (Fenteany et al., U.S. Pat. No. 5,756,764 (1998), U.S. Pat. No. 6,147,223 (2000), U.S. Pat. No. 6,335,358 (2002), and U.S. Pat. No. 6,645,999 (2003); Fenteany et al., *Proc. Natl. Acad. Sci. USA* (1994) 91:3358; Fenical et al., international patent publication WO 05/003137; Palladino et al., international patent publication WO 05/002572; Stadler et al., international patent publication WO 04/071382; Xiao and Patel, U.S. patent publication 2005/023162; and Corey, international patent publication WO 05/099687).

Genes such as NRAS and KRAS are mutated in many cancer types. There has been interest in public cataloging of mutations associated with cancers. Examples of public databases which include information about mutations associated with cancers are the Database of Genotypes and Phenotypes (dbGaP) maintained by the National Center for Biotechnology Information (Bethesda, Md.) and Catalogue of Somatic Mutations in Cancer (COSMIC) database maintained by the Wellcome Trust Sanger Institute (Cambridge, UK).

In an evaluation of 514 known mutations in 41 distinct oncogenes and tumor suppressor genes in tumor samples from xenograft tumors and cell lines, there were some samples which were resistant to inhibition by a proteasome inhibitor. Resistance to inhibition by a proteasome inhibitor was correlated to the mutation status of KRAS gene. Surprisingly, all of the samples from resistant xenografts had a mutation in KRAS and nearly all of the sensitive or responsive samples had wild type KRAS. Accordingly, a patient with a solid tumor whose tumor cells comprise wild type KRAS can be a candidate for treatment with a proteasome inhibitor. In some embodiments, the solid tumor is non-small cell lung cancer, colon cancer, pancreatic cancer, breast cancer, ovarian cancer, melanoma, head and neck carcinoma, prostate cancer or renal cell carcinoma. In other embodiments, the solid tumor is non-small cell lung cancer, colon cancer, pancreatic cancer, breast cancer, ovarian cancer or melanoma. In some embodiments, the solid tumor is non-small cell lung cancer, colon cancer, prostate cancer or pancreatic cancer. In some embodiments, the solid tumor is prostate cancer, pancreatic cancer, non-small cell lung cancer or colon cancer. In some embodiments, the solid tumor is prostate cancer, non-small cell lung cancer or colon cancer. In some embodiments, the solid tumor is selected from the group consisting of lung cancer and colon cancer. In some embodiments, the lung cancer is non-small cell lung cancer or a metastatic form of colon cancer. In other embodiments, the solid tumor is non-small cell lung cancer or colon cancer. In some embodiments, the solid tumor is lung cancer. In some embodiments, the solid tumor is non-small cell lung cancer. In some embodiments, the solid tumor is colon cancer.

Compositions and methods are provided to determine the mutational status, e.g., to identify mutations in marker genes in solid tumor, e.g., non-hematological tumor, e.g., non-small cell lung cancer, colon cancer, pancreatic cancer, breast cancer, ovarian cancer, melanoma, head and neck carcinoma, prostate cancer or renal cell carcinoma, to predict outcome, e.g., response to treatment, time-to-progression or survival, upon treatment with a proteasome inhibitor, e.g., a peptidyl boronic acid or peptidyl epoxy ketone. In some embodiments, compositions and methods are provided to determine the mutational status of a solid tumor selected from the group consisting of non-small cell lung cancer, colon cancer and prostate cancer to predict outcome of treatment with a proteasome inhibitor, e.g., a peptidyl boronic acid.

Unless otherwise defined, all technical and scientific terms used herein have the meanings which are commonly understood by one of ordinary skill in the art to which this invention belongs. Generally, nomenclature utilized in connection with, and techniques of cell and tissue culture, molecular biology and protein and oligo- or polynucleotide chemistry and hybridization described herein are those known in the art. GenBank or GenPept accession numbers and useful nucleic acid and peptide sequences can be found at the website maintained by the National Center for Biotechnology Information, Bethesda, Md. The content of all database accession records (e.g., from Affymetrix HG133 annotation files, Entrez, GenBank, RefSeq, COSMIC) cited throughout this application (including the Tables) are hereby incorporated by reference. Standard techniques are used for recombinant DNA, oligonucleotide synthesis, protein purification, tissue culture and transformation and transfection (e.g., electroporation, lipofection, etc). Enzymatic reactions, such as GTPase assay for RAS activity or assays, e.g., reporter assays, for RAS-activated signaling activity, are performed according to manufacturer's specifications or as commonly accomplished in the art or as described herein. Some methods for determining RAS localization and signaling are reviewed in Prior and Hancock (2011) *Semin. Clin. Dev. Biol.* September 8 epub; or found in Cuiffo and Ren (2010) *Blood* 114:3598-3605 or reviewed in Lim et al. (1996) *Eur. J. Biochem.* 242:171-185. The foregoing techniques and procedures generally are performed according to methods known in the art, e.g., as described in various general and more specific references that are cited and discussed throughout the present specification. See e.g., Sambrook et al. (2000) *Molecular Cloning: A Laboratory Manual* (3$^{rd}$ ed., Cold Spring Harbor Laboratory Press, Cold Spring Harbor, N.Y.) or Harlow, E. and Lane, D. (1988) *Antibodies: A Laboratory Manual* (Cold Spring Harbor Laboratory Press, Cold Spring Harbor, N.Y.). The nomenclatures utilized in connection with, and the laboratory procedures and techniques of, analytical chemistry, synthetic organic chemistry, and medicinal and pharmaceutical chemistry described herein are known in the art. Standard techniques are used for chemical syntheses, chemical analyses, pharmaceutical preparation, formulation and delivery, and treatment of patients. Furthermore, unless otherwise required by context, singular terms shall include pluralities and plural terms shall include the singular. In the case of conflict, the present specification, including definitions, will control.

The articles "a," "an" and "at least one" are used herein to refer to one or to more than one of the grammatical object of the article. By way of example, "an element" means one or more than one element, at least one element. In the case of conflict, the present specification, including definitions, will control.

As used herein, a "marker gene" or a "genotype marker gene" refers to a gene which can have a mutation, e.g., a genotype, such that its DNA, RNA and/or protein has a characteristic, e.g., size, sequence, composition, activity or amount(s) which provide information about prognosis or outcome (i.e., are "informative") upon treatment. Marker genes, e.g., genotype marker genes, described herein as linked to outcome after proteasome inhibitor, e.g., peptidyl boronic acid (e.g., bortezomib or ixazomib citrate) treatment are examples of genes within the chromosome locus markers described herein and are provided in Table 1. Sequences of mRNA, open reading frames and proteins corresponding to marker genes also are listed in Table 1. A marker gene, e.g., a genotype marker gene, listed in Table 1 can have isoforms which are either ubiquitous or have restricted expression. The DNA SEQ ID NOs in Table 1 refer only to the mRNA encoding the major or longest isoform and the protein SEQ ID NOs represent at least a precursor of such isoform and not necessarily the mature protein. These sequences are not intended to limit the marker gene identity to that isoform or precursor. The additional isoforms and mature proteins are readily retrievable and understandable to one of skill in the art by reviewing the information provided under the Entrez Gene (database maintained by the National Center for Biotechnology Information, Bethesda, Md.) identified by the ID number listed in Table 1.

KRAS functions as an oncogene with GTPase activity and can be found on chromosome 12. KRAS interacts with the cell membrane and various effector proteins, such as Akt and Cdc42, which carry out its signaling function through the cytoskeleton and effects on cell motility (Fotiadou et al. (2007) *Mol. Cel. Biol.* 27:6742-6755).

As used herein, "NRAS" refers to neuroblastoma RAS viral (v-ras) oncogene homolog, the gene associated with GenBank Accession No. NM_002524, SEQ ID NO:4 (open reading frame is SEQ ID NO:5, nucleotides 255 to 824 of SEQ ID NO:4), encoding GenPept Accession No. NP_002515, SEQ ID NO:6). Other names for NRAS include Autoimmune Lymphoproliferative Syndrome type IV (ALPS4), NRAS1, and Noonan Syndrome 6 (NS6). NRAS functions as an oncogene with GTPase activity and can be found on chromosome 1p. NRAS interacts with the cell membrane and various effector proteins, such as Raf and RhoA, which carry out its signaling function through the cytoskeleton and effects on cell adhesion (Fotiadou et al. (2007) *Mol. Cel. Biol.* 27:6742-6755).

As used herein, "GLUT4" refers to glucose transporter-4, the gene associated with GenBank Accession No. NM_001042, SEQ ID NO:7 (open reading frame is SEQ ID NO:8, nucleotides 201 to 1730 of SEQ ID NO:7), encoding GenPept Accession No. NP_001033, SEQ ID NO:8). Another name for GLUT4 is solute carrier family 2 (facilitated glucose transporter) member 4 (SLC2A4). GLUT4 functions as a glucose transporter and can be found on chromosome 17p. GLUT4 cellular location can depend on the presence of insulin, which stimulates cells such as

TABLE 1

Marker Gene Description

| Marker Gene ID | Marker Gene Name | Entrez Gene ID | Chromosome location | Start base pair | End base pair | SEQ ID NOs: |
|---|---|---|---|---|---|---|
| KRAS | v-Ki-ras2 Kirsten rat sarcoma viral oncogene homolog | 3845 | 12 p | 25358180 | 25403854 | 1, 2, 3 |
| NRAS | neuroblastoma RAS viral (v-ras) oncogene homolog | 4893 | 1 p | 115247085 | 115259515 | 4, 5, 6 |

As used herein, a "phenotype marker gene" refers to a marker gene in which there is no somatic DNA mutation, i.e., it has no genotype alteration, but its other markers, e.g., transcript, e.g., RNA, and/or protein can have a characteristic, e.g., size, sequence, composition, activity or amount which provides information about prognosis or outcome (i.e., is "informative") upon treatment. This designation is not to be confused with the characteristics, such as composition, amount and activity, measured for a marker associated with a genotype marker gene but which are known in the art as phenotypic characteristics. A phenotype marker gene described herein as linked to outcome after proteasome inhibitor, e.g., peptidyl boronic acid (e.g., bortezomib or ixazomib citrate) treatment includes GLUT4, SEQ ID NOs: 7, 8, 9.

As used herein, "KRAS" refers to v-Ki-ras2 Kirsten rat sarcoma viral oncogene homolog, the gene associated with GenBank Accession No. NM_004985, SEQ ID NO:1 (open reading frame is SEQ ID NO:2, nucleotides 182 to 748 of SEQ ID NO:1), encoding GenPept Accession No. NP_004976, SEQ ID NO:3, the predominant transcript variant of KRAS gene on chromosome 12. Other names for KRAS include KRAS2, and Noonan Syndrome 3 (NS3).

muscle and adipose tissue to move GLUT4 from intracellular stores to the cell surface to commence its function as a glucose transporter. Glucose transporters, including GLUT1, GLUT4 and GLUT9 can have higher than normal activity in tumor cells to allow higher levels of glucose metabolism than in normal cells (reviewed Adekola et al. (2012) 24:650-654). GLUT1, GLUT3 and GLUT4 can be expressed in lung carcinoma (Ito et al. (1999) *Histol. Histopathol.* 14:895-904). KRAS mutant colorectal cancer cells showed higher glucose uptake and glycolysis and better growth and survival under nutrient stress than wild type cells (Yun et al. 2009 *Science* 325:1555). Those studies identified a correlation between the upregulation of GLUT1, glucose transporter 1, with mutant KRAS in colorectal cancer cells, in contrast with an earlier study (Noguchi et al. (2000) *Cancer Lett.* 154:137-142).

A "marker" as used herein, includes a material associated with a marker gene which has been identified as having a mutation in tumor cells of a patient and furthermore that mutation is characteristic of a patient whose outcome is favorable or unfavorable with treatment e.g., by a proteasome inhibitor, e.g., a peptidyl boronic acid or peptidyl epoxy ketone. Examples of a marker include a material, e.g., a chromosome locus, DNA for a gene, RNA for a gene or protein for a gene. For example, a marker includes a marker gene material, e.g., a chromosome locus, DNA, RNA or protein whose mutation or characteristic, e.g., size, sequence, composition, activity or amount is indicative of a patient with a poor response to treatment; alternatively a marker includes a marker gene material, e.g., a chromosome locus, DNA, RNA or protein whose mutation or characteristic, e.g., size, sequence, composition, activity or amount is indicative of a patient with a good response. In another example, a marker includes a marker gene material, e.g., a chromosome locus, DNA, RNA or protein whose mutation or characteristic, e.g., size, sequence, composition, activity or amount is indicative of a patient whose disease has a short time-to-progression (TTP) upon treatment; alternatively a marker includes a marker gene material, e.g., a chromosome locus, DNA, RNA or protein whose mutation or characteristic, e.g., size, sequence, composition, activity or amount is indicative of a patient whose disease has a long TTP. In yet a further example, a marker includes a marker gene material, e.g., a chromosome locus, DNA, RNA or protein whose mutation or characteristic, e.g., size, sequence, composition or amount is indicative of a patient whose disease has a short term survival upon treatment; alternatively a marker includes a marker gene material, e.g., a chromosome locus, DNA, RNA or protein whose mutation or characteristic, e.g., size, sequence, composition or amount is indicative of a patient whose disease has a long term survival. A marker can include a material associated with a marker gene which has not been identified as having a mutation in tumor cells of a patient, but whose characteristic, e.g., size, sequence, composition, activity or amount is indicative of response to proteasome inhibition treatment of a solid tumor in a patient. Thus, as used herein, a marker is intended to include each and every one of these possibilities, and further can include each single marker individually or independently as a marker; or alternatively can include one or more, or all of the characteristics collectively when reference is made to "markers" or "marker sets."

In some embodiments, the marker is selected from the group consisting of nucleic acid and protein. In some embodiments, the marker is nucleic acid. In some embodiments, the nucleic acid marker is chromosomal or genomic DNA. In some embodiments, the nucleic acid is mRNA. In some embodiments, the nucleic acid is cDNA prepared from mRNA. In some embodiments, the marker is protein.

In some embodiments, the characteristic is selected from the group consisting of size, sequence, composition, activity and amount. In some embodiments, the characteristic is sequence. In some embodiments, the characteristic is amount. In some embodiments, the characteristic is composition. In some embodiments, the characteristic is size. In some embodiments, the characteristic is activity.

In some embodiments, the marker is chromosome DNA, or genomic DNA and the characteristic is sequence. In some embodiments, the marker is mRNA and the characteristic is sequence. In some embodiments, the marker is cDNA and the characteristic is sequence. In some embodiments, the marker is mRNA and the characteristic is amount. In some embodiments, the marker is mRNA and the characteristic is size.

In some embodiments, the marker is protein and the characteristic is amount. In some embodiments, the marker is protein and the characteristic is activity. In some embodiments, the marker is protein and the characteristic is sequence.

A chromosome locus marker useful to measure for determination of prognosis or treatment or disease management strategy is selected from the group consisting of chromosome 1p13.2 (NRAS), e.g., from base pair 115247085 to 115259515 and chromosome 12p12.1 (KRAS), e.g., from base pair 25358180 to 25403854. Chromosome locus and base pair numbers are based on the reference human genome Build 37.3 (current as of Oct. 5, 2011) in the NCBI Gene database. A marker DNA, marker RNA or marker protein can correspond to base pairs on a chromosome locus marker. For example, a marker DNA can include genomic DNA from a chromosome locus marker, marker RNA can include a polynucleotide transcribed from a locus marker, and a marker protein can include a polypeptide resulting from expression at a chromosome locus marker in a sample, e.g., comprising tumor cells.

A "marker nucleic acid" is a nucleic acid (e.g., genomic DNA, mRNA, cDNA) encoded by, associated with or corresponding to a marker gene of the invention. Such marker nucleic acids include DNA, e.g., sense and anti-sense strands of genomic DNA (e.g., including any introns occurring therein), comprising the entire or a partial sequence, e.g., one or more of the exons of the genomic DNA, up to and including the open reading frame of any of the marker genes or the complement of such a sequence. The marker nucleic acids also include RNA comprising the entire or a partial sequence of any marker or the complement of such a sequence, wherein all thymidine residues are replaced with uridine residues, RNA generated by transcription of genomic DNA (i.e. prior to splicing), RNA generated by splicing of RNA transcribed from genomic DNA, and proteins generated by translation of spliced RNA (i.e. including proteins both before and after cleavage of normally cleaved regions such as transmembrane signal sequences). As used herein, a "marker nucleic acid" may also include a cDNA made by reverse transcription of an RNA generated by transcription of genomic DNA (including spliced RNA). A marker nucleic acid also includes sequences which differ, due to degeneracy of the genetic code, from the nucleotide sequence of nucleic acids encoding a protein which corresponds to a marker of the invention, and thus encode the same protein or highly similar protein, e.g., wild type protein or protein with polymorphism but wild type function. As used herein, the phrase "allelic variant" refers to a nucleotide sequence which occurs at a given locus or to a polypeptide encoded by the nucleotide sequence. Such naturally occurring allelic variations can typically result in 1-5% variance in the nucleotide sequence of a given gene. Alternative alleles can be identified by sequencing the gene of interest in a number of different individuals, e.g., in cells, e.g., germline cells, of individuals without cancer. This can be readily carried out by using hybridization probes to identify the same genetic locus in a variety of individuals. Detection of any and all such nucleotide variations and resulting amino acid polymorphisms or variations that are the result of naturally occurring allelic variation and that do not alter the functional activity of a wild type marker gene is intended to be within the scope of the wild type version of a marker described herein. A "marker protein" is a protein encoded by or corresponding to a marker, e.g., a nucleic acid, of the invention. The terms "protein" and "polypeptide' are used interchangeably. A protein of a marker specifically can be referred to by its name or amino acid sequence, but it is understood by those skilled in the art, that mutations, such as non-sense, missense, insertions or deletions can affect protein structure, appearance, cellular location and/or behavior in a variety of ways. Unless indicated otherwise, such differences are not distinguished herein, and a mutant marker described herein is intended to include any or all such varieties.

A typical tumor with a mutated RAS gene has a mutation in one RAS gene or another, not more than one. In the case of KRAS, an example of wild type nucleic acid such as mRNA is SEQ ID NO:1. Another example of wild type KRAS nucleic acid is SEQ ID NO:2. An example of wild type KRAS protein is SEQ ID NO:3. In some embodiments, a mutation can be found in at least one mutation site of a KRAS marker. In the present studies, mutations were found in codons 12, 13, 61 and 146 of KRAS (SEQ ID NO:2). In general embodiments, a wild type RAS gene, e.g., KRAS, is predictive of favorable outcome, e.g., responsiveness, long time to progression and/or long term survival, for solid, e.g., non-hematological tumors, e.g., non-small cell lung cancer or colon cancer, while a mutated KRAS gene is predictive of unfavorable outcome. In some embodiments, a mutation site comprising a mutation of codon 146 of KRAS (SEQ ID NO:2) is not predictive of unfavorable outcome of treatment with a proteasome inhibitor. As used herein, a "mutation of codon 146" or "mutated codon 146" refers to a rare mutation in the open reading frame of KRAS, SEQ ID NO:2. A marker whose characteristic is informative of a mutated codon 146 can be a KRAS protein with an amino acid sequence which differs from SEQ ID NO:3 at amino acid residue 146. In some embodiments, a protein marker whose characteristic is informative of a favorable outcome in the methods has a threonine instead of an alanine at residue 146 of KRAS. A nucleic acid marker comprising a fragment of at least 10 consecutive nucleotides of SEQ ID NO:1, or a complement thereof, wherein the fragment comprises bases 617 to 619, can have a characteristic informative of a mutation of codon 146 if at least one base selected from the group consisting of bases 617, 618 and 619 is mutated.

Examples of mutant KRAS, whose occurrence in a solid tumor cancer patient is indicative of nonresponse or unfavorable outcome include marker nucleic acid with at least one change in at least one mutation site, such as at least one base of codon 12 (bases 34-36), codon 13 (bases 37-39) or codon 61 (bases 181-183) of SEQ ID NO:2, or the analogous codons in SEQ ID NO:1 (bases 215-217, bases 218-220 or bases 362-364, respectively of SEQ ID NO:1), and results in a change of at least one amino acid residue 12, 13 or 61 of SEQ ID NO:3. In some embodiments, an allelic variant of KRAS has a change in a codon that is not codon 12, codon 13 or codon 61 of SEQ ID NO:2, or the analogous codons in SEQ ID NO:1, wherein the resulting encoded allelic variant protein has wild type RAS, e.g., GTPase, activity, and thus is not associated with unfavorable outcome. Alternatively, an allelic variant of KRAS has a change in a base of codon 12, codon 13, or codon 61 wherein the change, e.g., is due to the degeneracy of the genetic code and does not result in a change in the translated residue. In such embodiments, an allelic variant nucleic acid encodes a wild type amino acid residue, such as glycine at position 12 of SEQ ID NO:3, glycine at position 13 of SEQ ID NO:3 and glutamine at position 61 of SEQ ID NO:3 and the encoded polypeptide has wild type RAS activity, e.g., GTPase activity, and thus is not associated with unfavorable outcome.

A nucleic acid marker comprising a fragment of at least 10 consecutive nucleotides of SEQ ID NO:1, or a complement thereof, wherein the fragment comprises bases 215 to 217 can have a characteristic informative of a mutation of codon 12 if at least one base selected from the group consisting of bases 215, 216 and 217 is mutated in a manner that can result in a change of the amino acid residue 12 of SEQ ID NO:3.

In some embodiments, the nucleic acid marker comprises bases 34 to 36 of SEQ ID NO:2. In some embodiments, a mutation in KRAS nucleic acid can result in a KRAS protein which has an amino acid residue selected from the group consisting of alanine, cysteine, aspartate, phenylalanine, arginine, serine and valine instead of glycine at residue 12 of SEQ ID NO:3. A nucleic acid marker comprising a fragment of at least 10 consecutive nucleotides of SEQ ID NO:1, or a complement thereof, wherein the fragment comprises bases 218 to 220, can have a characteristic informative of a mutation of codon 13 if at least one base selected from the group consisting of bases 218, 219 and 220 is mutated in a manner that can result in a change of the amino acid residue 13 of SEQ ID NO:3. In some embodiments, the nucleic acid marker comprises bases 37 to 39 of SEQ ID NO:2. In some embodiments, a mutation in KRAS nucleic acid can result in a KRAS protein which has an amino acid residue selected from the group consisting of aspartate, valine, cysteine, serine, alanine and arginine instead of glycine at residue 13 of SEQ ID NO:3. A nucleic acid marker comprising a fragment of at least 10 consecutive nucleotides of SEQ ID NO:1, or a complement thereof, wherein the fragment comprises bases selected from the group consisting of bases 362 to 364, can have a characteristic informative of a mutation of codon 61 if at least one base selected from the group consisting of bases 362, 363 and 364 is mutated in a manner that can result in a change of the amino acid residue 61 of SEQ ID NO:3. In some embodiments, the nucleic acid marker comprises bases 181 to 183 of SEQ ID NO:2. In some embodiments, a mutation in KRAS nucleic acid can result in a KRAS protein which has an amino acid residue selected from the group consisting of glutamate, histidine, lysine, leucine, proline and arginine instead of glutamine at residue 61 of SEQ ID NO:3.

As used herein, an "informative" characteristic, e.g., size, sequence, composition, activity or amount of a marker refers to a characteristic, e.g., size, sequence, composition, activity or amount whose value or difference is correlated to prognosis or outcome. The informative characteristic, e.g., size, sequence, composition, activity or amount of a marker can be obtained by analyzing either nucleic acid, e.g., DNA or RNA, or protein corresponding to the marker gene, e.g., a genotype marker gene or phenotype marker gene. The characteristic, e.g., size (e.g., length or molecular weight), sequence (e.g., nucleic acid sequence or protein sequence), composition (e.g., base or amino acid composition or peptide digest or gene fragment pattern), activity (enzymatic activity or signaling activity) or amount (e.g., copy number and/or expression level) of a marker, e.g., a chromosome locus marker or a marker in a sample from a patient is "informative" if it is different than the wild type or allelic variant of the substance being analyzed. In some embodiments, a characteristic of a marker is informative if it indicates that the marker gene is wild type. In some embodiments where the amount of a marker is being measured, an amount is "informative" if it is greater than or less than a reference amount by a degree greater than the standard error of the assay employed to assess expression. The informative expression level of a marker can be determined upon statistical correlation of the measured expression level and the outcome, e.g., good response, poor response, long time-to-progression, short time-to-progression, short term survival or long term survival. The result of the statistical analysis can establish a threshold for selecting markers to use in the methods described herein. Alternatively, a marker, e.g., a chromosome locus marker, or a marker gene that has differential characteristic, e.g., size, sequence, composition, activity or amounts will have typical ranges of amounts that are predictive of outcome. An informative characteristic, e.g., size, sequence, composition, activity or amount is a characteristic, e.g., size, sequence, composition, activity or amount that falls within the range of characteristic, e.g., size, sequence, composition, activity or amounts determined for the outcome. Still further, a set of markers may together be "informative" if the combination of their characteristics, e.g., sizes, sequences, compositions, activities or amounts either meets or is above or below a pre-determined score for a marker, e.g., a chromosome locus marker, or a marker gene set as determined by methods provided herein. Gene translocation, transcript splice variation, deletion and truncation are examples of events which can change marker size, sequence or composition, in addition to point mutations which can change marker sequence or composition. Measurement of only one characteristic, e.g., marker, of a marker gene (i.e., DNA, RNA or protein) can provide a prognosis, i.e., indicate outcome. Measurement of only one characteristic, e.g., marker, of a marker gene (i.e., DNA, RNA or protein) can provide a prognosis, i.e., predict or indicate outcome. Measurement of more than one characteristic, e.g., marker, of a marker gene can provide a prognosis when the informative results of the two characteristics are consistent with each other, i.e., the biologies of the results are not contradictory. Examples of consistent results from measurement of multiple characteristics of a marker gene can be identification of a nonsense mutation, point mutation, insertion or deletion in a DNA or RNA and a low amount or altered molecular weight of encoded protein, or a mutation in a region which encodes a binding pocket or active site of a protein and altered activity of the encoded protein. A different example can occur when a protein is in a pathway with a feedback loop controlling its synthesis based on its activity level. In this example, a low amount or activity of protein can be associated with a high amount of its mutated mRNA as a tissue, due to the marker gene mutation, thus is starved for the protein activity and repeatedly signals the production of the protein.

By way of non-limiting illustration, in the present case, an example of an informative result upon measuring a characteristic, e.g, a sequence, of a KRAS marker, e.g., DNA, mRNA, or protein, would be a result identifying the mutational status of a KRAS sequence, e.g., SEQ ID NO:1, 2 or 3. In the present case, identifying a mutation in the KRAS sequence in a sample comprising tumor cells would be informative of an unfavorable outcome, while identifying wild type sequence would be informative of a favorable outcome of treatment of the tumor with a proteasome inhibitor. In one embodiment, identifying an A146T mutation in KRAS would be informative of a favorable outcome. In another example, measuring a characteristic, e.g, activity of a KRAS marker, e.g, protein, would provide an informative result of a favorable outcome if there is a high GTPase activity or a low signaling activity.

A "normal" characteristic, e.g., size, sequence, composition, activity or amount of a marker may refer to the characteristic, e.g., size, sequence, composition, activity or amount in a "reference sample." A reference sample can be a matched normal, e.g., germline, sample from the same patient from whom the tumor, e.g., with a somatic mutation, is derived. A reference sample can be a sample from a healthy subject not having the marker-associated disease or a reference characteristic e.g., the average characteristic, e.g., size, sequence, composition, activity or amount of the wild type marker in several healthy subjects. A reference sample characteristic, e.g., size, sequence, composition, activity or amount may be comprised of a characteristic, e.g., size, sequence, composition, activity or amount of one or more markers from a reference database. Alternatively, a "normal" characteristic, e.g., size, sequence, composition, activity or level of expression of a marker is the characteristic, e.g., size, sequence, composition, activity or amount of the marker, e.g., marker gene in non-tumor cells in a similar environment or response situation from the same patient from whom the tumor is derived. The normal amount of DNA copy number is 2 or diploid, with the exception of X-linked genes in males, where the normal DNA copy number is 1.

"Over-expression" and "under-expression" of a marker gene, refer to expression of the marker gene of a patient at a greater or lesser level (e.g. more than three-halves-fold, at least two-fold, at least three-fold, greater or lesser level etc.), respectively, than normal level of expression of the marker gene, e.g., as measured by mRNA or protein, in a test sample that is greater than the standard error of the assay employed to assess expression. A "significant" expression level may refer to a level which either meets or is above or below a pre-determined score for a marker gene set as determined by methods provided herein.

As used herein, "gene deletion" refers to an amount of DNA copy number less than 2 and "amplification" refers to an amount of DNA copy number greater than 2. A "diploid" amount refers to a copy number equal to 2. The term "diploid or amplification" can be interpreted as "not deletion" of a gene copy. In a marker whose alternative informative amount is gene deletion, amplification generally would not be seen. Conversely, the term "diploid or deletion" can be interpreted as "not amplification" of copy number. In a marker whose alternative informative amount is amplification, gene deletion generally would not be seen. For the sake of clarity, sequence deletion can occur within a gene as a result of marker gene mutation and can result in absence of transcribed protein or a shortened mRNA or protein. Such a deletion may not affect copy number.

As used herein, a "favorable" outcome or prognosis refers to long time-to-progression (TTP, or progression-free survival), long term survival, and/or good response. Conversely, an "unfavorable" outcome or prognosis refers to short term survival, short time-to-progression (TTP, or progression-free survival) and/or poor response.

The terms "long term survival" and "short term survival" refer to the length of time after receiving a first dose of treatment that a cancer patient is predicted to live. A "long term survivor" refers to a patient expected have a slower rate of progression or later death from the tumor than those patients identified as short term survivors. "Enhanced survival" or "a slower rate of death" are estimated life span determinations based upon characteristic, e.g., size, sequence, composition, activity or amount of one or more of markers described herein, e.g., as compared to a reference standard such that 70%, 80%, 90% or more of the population will be alive a sufficient time period after receiving a first dose of treatment. A "faster rate of death" or "shorter survival time" refer to estimated life span determinations based upon characteristic, e.g., size, sequence, composition, activity or amount of one or more of markers described herein, e.g., as compared to a reference standard such that 50%, 40%, 30%, 20%, 10% or less of the population will not live a sufficient time period after receiving a first dose of treatment. In some embodiments, the sufficient time period is at least 6, 12, 18, 24 or 30 months measured from the first day of receiving a cancer therapy.

A cancer is "responsive" to a therapeutic agent or there is a "good response" to a treatment if its rate of growth is inhibited as a result of contact with the therapeutic agent, compared to its growth in the absence of contact with the therapeutic agent. Growth of a cancer can be measured in a variety of ways, for instance, the characteristic, e.g., size of a tumor or the expression of tumor markers appropriate for that tumor type may be measured. International Working Groups convene periodically to set, update and publish response criteria for various types of cancers. Such published reports can be followed to support the identification of markers of the subject tumors and their response to proteasome inhibitors. For example, for solid tumors, the Response Evaluation Criteria in Solid Tumors (RECIST) guidelines (Eisenhauer et al. (2009) *E. J. Canc.* 45:228-247) can be used to support the identification of markers associated with solid tumors and response of solid tumors to a proteasome inhibitor. The response definitions used to support the identification of markers associated with myeloma and its response to an proteasome inhibitor, e.g., peptidyl boronic acid therapy, the Southwestern Oncology Group (SWOG) criteria as described in Blade et al. (1998) *Br J Haematol.* 102:1115-23 can be used. These criteria define the type of response measured in myeloma and also the characterization of time to disease progression which is another important measure of a tumor's sensitivity to a therapeutic agent. Other examples are criteria for Acute Myelogenous Leukemia (AML, Cheson et al. (2003) *J. Clin. Oncol.* 21:4642-4649), lymphomas, e.g., non-Hodgkin's and Hodgkin's lymphoma (Cheson et al. (2007) *J. Clin. Oncol.* 25:579-596). Criteria take into account analysis methods such as Positron Emission Tomography (PET), e.g., for identifying sites with measurable altered metabolic activity (e.g., at tumor sites) or to trace specific markers into tumors in vivo, immunohistochemistry, e.g., to identify tumor cells by detecting binding of antibodies to specific tumor markers, and flow cytometry, e.g., to characterize cell types by differential markers and fluorescent stains, in addition to traditional methods such as histology to identify cell composition (e.g., blast counts in a blood smear or a bone marrow biopsy, presence and number of mitotic figures) or tissue structure (e.g., disordered tissue architecture or cell infiltration of basement membrane). The quality of being responsive to a proteasome inhibitor, e.g., a peptidyl boronic acid therapy can be a variable one, with different cancers exhibiting different levels of "responsiveness" to a given therapeutic agent, under different conditions. Still further, measures of responsiveness can be assessed using additional criteria beyond growth size of a tumor, including patient quality of life, degree of metastases, etc. In addition, clinical prognostic markers and variables can be assessed (e.g., M protein in myeloma, PSA levels in prostate cancer) in applicable situations.

A cancer is "non-responsive" or has a "poor response" to a therapeutic agent or there is a poor response to a treatment if its rate of growth is not inhibited, or inhibited to a very low degree, as a result of contact with the therapeutic agent when compared to its growth in the absence of contact with the therapeutic agent. As stated above, growth of a cancer can be measured in a variety of ways, for instance, the size of a tumor or the expression of tumor markers appropriate for that tumor type may be measured. For example, the response definitions used to support the identification of markers associated with non-response of tumors to therapeutic agents, guidelines such as those described above can be used. The quality of being non-responsive to a therapeutic agent can be a highly variable one, with different cancers exhibiting different levels of "non-responsiveness" to a given therapeutic agent, under different conditions. Still further, measures of non-responsiveness can be assessed using additional criteria beyond growth size of a tumor, including patient quality of life, degree of metastases, etc. In addition, clinical prognostic markers and variables can be assessed (e.g., M protein in myeloma, PSA levels in prostate cancer) in applicable situations.

As used herein, "long time-to-progression, "long TTP" and "short time-to-progression," "short TTP" refer to the amount of time until when the stable disease brought by treatment converts into an active or progressive disease. On occasion, a treatment results in stable disease (SD) which is neither a good nor a poor response, or MR, the disease merely does not get worse, e.g., does not become a progressive disease, for a period of time. This period of time can be at least 4-8 weeks, at least 3-6 months or more than 6 months.

"Treatment" shall mean the use of a therapy to prevent or inhibit further tumor growth, as well as to cause shrinkage of a tumor, and to provide longer survival times. Treatment is also intended to include prevention of metastasis of tumor. A tumor is "inhibited" or "treated" if at least one symptom (as determined by responsiveness/non-responsiveness, time to progression, or indicators known in the art and described herein) of the cancer or tumor is alleviated, terminated, slowed, minimized, or prevented. Any amelioration of any symptom, physical or otherwise, of a tumor pursuant to treatment using a therapeutic regimen (e.g., proteasome inhibitor, e.g., a peptidyl boronic acid regimen) as further described herein, is within the scope of the invention.

As used herein, the term "agent" is defined broadly as anything that cancer cells, including tumor cells, may be exposed to in a therapeutic protocol. In the context of the present invention, such agents include, but are not limited to, proteasome inhibitor, e.g., a peptidyl boronic acid agents, as well as chemotherapeutic agents as known in the art and described in further detail herein.

The term "probe" refers to any molecule, e.g., an isolated molecule, which is capable of selectively binding to a specifically intended target molecule, for example a marker of the invention. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic monomers.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In some embodiments, the first region comprises a first portion and the second region comprises a second portion, whereby, when the first and second portions are arranged in an antiparallel fashion, at least about 50%, at least about 75%, at least about 90%, or at least about 95% or all of the nucleotide residues of the first portion are capable of base pairing with nucleotide residues in the second portion.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue (i.e., by percent identity). By way of example, a region having the nucleotide sequence 5'-ATTGCC-3' and a region having the nucleotide sequence 5'-TATGGC-3' share homology with 50% identity. In one embodiment, the first region comprises a first portion and the second region comprises a second portion, whereby, at least about 50%, at least about 75%, at least about 90%, or at least about 95% of the nucleotide residue positions of each of the portions are occupied by the same nucleotide residue. In some embodiments of 100% identity, all nucleotide residue positions of each of the portions are occupied by the same nucleotide residue.

Unless otherwise specified herewithin, the terms "antibody" and "antibodies" broadly encompass naturally-occurring forms of antibodies, e.g., polyclonal antibodies (e.g., IgG, IgA, IgM, IgE) and monoclonal and recombinant antibodies such as single-chain antibodies, two-chain and multi-chain proteins, chimeric, CDR-grafted, human and humanized antibodies and multi-specific antibodies, as well as fragments and derivatives of all of the foregoing, which fragments (e.g., dAbs, scFv, Fab, F(ab)'$_2$, Fab') and derivatives have at least an antigenic binding site. Antibody derivatives may comprise a protein or chemical moiety conjugated to an antibody. The term "antibody" also includes synthetic and genetically engineered variants.

A "kit" is any article of manufacture (e.g., a package or container) comprising at least one reagent, e.g. a probe, for specifically detecting a marker or marker set of the invention. The article of manufacture may be promoted, distributed, sold or offered for sale as a unit for performing, e.g., in vitro, the methods of the present invention, e.g., on a sample having been obtained from a patient. The reagents included in such a kit can comprise at least one nucleic acid probe and, optionally, one or more primers and/or antibodies for use in analyzing one or more markers described herein, e.g., detecting marker characteristics, e.g., size, sequence composition or amount, e.g., expression. In addition, a kit of the present invention can contain instructions which describe a suitable detection assay. Such a kit can be conveniently used, e.g., in a clinical or a contract testing setting, to generate information, e.g., on expression levels, characteristic, e.g., size, sequence, activity or composition of one or more marker, to be recorded, stored, transmitted or received to allow for diagnosis, evaluation or treatment of patients exhibiting symptoms of cancer, in particular patients exhibiting the possible presence of a cancer capable of treatment with proteasome inhibition therapy, including, e.g., non-hematological cancers e.g., non-small cell lung cancer, colon cancer, pancreatic cancer, breast cancer, ovarian cancer, melanoma, head and neck carcinoma, prostate cancer or renal cell carcinoma.

The present methods and compositions are designed for use in diagnostics and therapeutics for a patient suffering from cancer. A cancer or tumor is treated or diagnosed according to the present methods. "Cancer" or "tumor" is intended to include any neoplastic growth in a patient, including an initial tumor and any metastases. The cancer can be of the hematological or solid tumor type. Hematological tumors include tumors of hematological origin, including, e.g., myelomas (e.g., multiple myeloma), leukemias (e.g., Waldenstrom's syndrome, chronic lymphocytic leukemia, acute myelogenous leukemia, chronic myelogenous leukemia, other leukemias), lymphomas (e.g., B-cell lymphomas, non-Hodgkin's lymphoma) and myelodysplastic syndrome. Solid tumors can originate in organs, and include cancers such as in skin, lung, brain, breast, prostate, ovary, colon, kidney, pancreas, liver, esophagus, stomach, intestine, bladder, uterus, cervix, testis, adrenal gland, etc. The cancer can comprise a cell in which a marker gene has a mutation. As used herein, cancer cells, including tumor cells, refer to cells that divide at an abnormal (increased) rate or whose control of growth or survival is different than for cells in the same tissue where the cancer cell arises or lives. Cancer cells include, but are not limited to, cells in carcinomas, such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), and lymphomas (e.g., follicular lymphoma, mantle cell lymphoma, diffuse large Bcell lymphoma, malignant lymphoma, plasmocytoma, reticulum cell sarcoma, or Hodgkins disease); and tumors of the nervous system including glioma, meningoma, medulloblastoma, schwannoma or epidymoma.

As used herein, the term "noninvasive" refers to a procedure which inflicts minimal harm to a subject. In the case of clinical applications, a noninvasive sampling procedure can be performed quickly, e.g., in a walk-in setting, typically without anaesthesia and/or without surgical implements or suturing. Examples of noninvasive samples include blood, serum, saliva, urine, buccal swabs, throat cultures, stool samples and cervical smears. Noninvasive diagnostic analyses include x-rays, magnetic resonance imaging, positron emission tomography, etc.

Described herein is the assessment of outcome for treatment of a tumor through measurement of the amount of pharmacogenomic markers, e.g, the mutation status of a genotype marker gene, e.g., RAS. Methods of the invention can be characterized as comprising detecting, in a sample of cells or nucleic acid from the patient, the presence or absence of wild type or mutant KRAS gene. The mutations can be: (i) a difference in the identity of at least one nucleotide or (ii) a difference in the number of nucleotides, which difference can be a single nucleotide or several nucleotides. The invention also provides methods for detecting differences in KRAS genes such as chromosomal rearrangements, e.g., chromosomal dislocation. Also described are assessing the outcome by noninvasive, convenient or low-cost means, for example, from blood samples. Typical methods to determine extent of cancer or outcome of a solid, e.g., non-hematological tumor, e.g non-small cell lung cancer, colon cancer, pancreatic cancer, breast cancer, ovarian cancer, melanoma, head and neck carcinoma, prostate cancer or renal cell carcinoma can employ biopsy to collect tissue for genotype or phenotype, e.g., histological analysis. The invention provides methods for determining, assessing, advising or providing an appropriate therapy regimen for treating a tumor or managing disease in a patient. Monitoring a treatment using the kits and methods disclosed herein can identify the potential for unfavorable outcome and allow their prevention, and thus a savings in morbidity, mortality and treatment costs through adjustment in the therapeutic regimen, cessation of therapy or use of alternative therapy.

The term "sample" is intended to include a sample, e.g, tissue, cells, biological fluids and isolates thereof, isolated from a subject, as well as tissues, cells and fluids present within a subject and can be obtained from a patient or a normal subject. In hematological tumors of the bone marrow, e.g., myeloma tumors, primary analysis of the tumor can be performed on bone marrow samples, e.g., samples which comprise myeloma tumor cells. However, some tumor cells, (e.g., clonotypic tumor cells, circulating endothelial cells), are a percentage of the cell population in whole blood. These cells also can be mobilized into the blood during treatment of the patient with granulocyte-colony stimulating factor (G-CSF) in preparation for a bone marrow transplant, a standard treatment for hematological tumors, e.g., leukemias, lymphomas and myelomas. Examples of circulating tumor cells in multiple myeloma have been studied e.g., by Pilarski et al. (2000) *Blood* 95:1056-65 and Rigolin et al. (2006) *Blood* 107:2531-5. Thus, noninvasive samples, e.g., for in vitro measurement of markers to determine outcome of treatment, can include peripheral blood samples. Accordingly, cells within peripheral blood can be tested for marker amount. For patients with hematological tumors, a control, reference sample for normal characteristic, e.g., size, sequence, composition, activity or amount can be obtained from skin or a buccal swab of the patient. For solid tumors, a typical sample comprising tumor cells is a biopsy of the primary tumor or neighboring lymph nodes. Solid tumor samples obtained by less invasive means e.g., shed or scraped from the tumor site include a cervical smear (e.g., from a cervical cancer patient), tumor exudate, e.g., lymph fluid, cystic fluid, nipple aspirate (e.g., from a breast cancer patient), ascites fluid, pleural fluid, sputum (e.g., from lung cancer patient), gynecological fluids (e.g., from an ovarian cancer patient), urine, stool (e.g., for colon cancer). For solid tumors, a control, reference sample for normal characteristic, e.g., size, sequence, composition, activity or amount can be obtained from blood of the patient.

In some embodiments, tumor cells are selected from the group consisting of lung cancer cells and colon cancer cells. In some embodiments, a sample comprising solid tumor cells comprises lung cancer cells. In some embodiments, a sample comprising solid tumor cells comprises non-small cell lung cancer cells. In some embodiments, a sample comprising solid tumor cells comprises colon cancer cells.

Blood collection containers can comprise an anti-coagulant, e.g., heparin or ethylene-diaminetetraacetic acid (EDTA), sodium citrate or citrate solutions with additives to preserve blood integrity, such as dextrose or albumin or buffers, e.g., phosphate. If the amount of marker is being measured by measuring the level of its DNA in the sample, a DNA stabilizer, e.g., an agent that inhibits DNAse, can be added to the sample. If the amount of marker is being measured by measuring the level of its RNA in the sample, an RNA stabilizer, e.g., an agent that inhibits RNAse, can be added to the sample. If the amount of marker is being measured by measuring the level of its protein in the sample, a protein stabilizer, e.g., an agent that inhibits proteases, can be added to the sample. An example of a blood collection container is PAXGENE® tubes (PREANALYTIX, Valencia, Calif.), useful for RNA stabilization upon blood collection. Peripheral blood samples or tumor exudates can be modified, e.g., fractionated, sorted or concentrated (e.g., to result in samples enriched with tumor or depleted of tumor (e.g., for a reference sample)). Examples of modified samples include clonotypic myeloma cells, which can be collected by e.g., negative selection, e.g., separation of white blood cells from red blood cells (e.g., differential centrifugation through a dense sugar or polymer solution (e.g., FICOLL® solution (Amersham Biosciences division of GE healthcare, Piscataway, N.J.) or HISTOPAQUE®-1077 solution, Sigma-Aldrich Biotechnology LP and Sigma-Aldrich Co., St. Louis, Mo.)) and/or positive selection by binding B cells to a selection agent (e.g., a reagent which binds to a tumor cell or myeloid progenitor marker, such as CD34, CD38, CD138, or CD133, for direct isolation (e.g., the application of a magnetic field to solutions of cells comprising magnetic beads (e.g., from Miltenyi Biotec, Auburn, Calif.) which bind to the B cell markers) or fluorescent-activated cell sorting). Non-myeloma samples, e.g., tumor exudates from solid tumors, can be treated by similar methods as myeloma samples to enrich for tumor cells, e.g., using tumor cell selection markers known in the art.

Alternatively, a tumor cell line, e.g., HCT-116, A549, NCI-H1975, NCI-H1650, HCC-827, SW48, Calu-1, OCI-Ly3, OCI-Ly10 cell (Alizadeh et al. (2000) *Nature* 403:503-511), a RPMI 6666 cell, a SUP-B15 cell, a KG-1 cell, a CCRF-SB cell, an 8ES cell, a Kasumi-1 cell, a Kasumi-3 cell, a BDCM cell, an HL-60 cell, a Mo-B cell, a JM1 cell, a GA-10 cell or a B-cell lymphoma (e.g., BC-3) or a cell line or a collection of tumor cell lines (see e.g., McDermott et al. (2007) *PNAS* 104:19936-19941 or ONCOPANEL™ anticancer tumor cell profiling screen (Ricerca Biosciences, Bothell, Wash.)) can be assayed. A skilled artisan readily can select and obtain the appropriate cells (e.g., from American Type Culture Collection (ATCC®), Manassas, Va.) that are used in the present method. If the compositions or methods are being used to predict outcome of treatment in a patient or monitor the effectiveness of a therapeutic protocol, then a tissue or blood sample having been obtained from the patient being treated is a useful source of cells or marker gene or gene products for an assay.

The sample, e.g., tumor, e.g., biopsy or bone marrow, blood or modified blood, (e.g., comprising tumor cells), tumor exudate and/or the reference, e.g., matched control (e.g., germline), sample can be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample.

In some embodiments, a mutation in a marker can be identified by sequencing a nucleic acid, e.g., a DNA, RNA, cDNA or a protein correlated with the marker gene, e.g., a genotype marker gene, e.g., KRAS. There are several sequencing methods known in the art to sequence nucleic acids. A nucleic acid primer can be designed to bind to a region comprising a potential mutation site or can be designed to complement the mutated sequence rather than the wild type sequence. Primer pairs can be designed to bracket a region comprising a potential mutation in a marker gene. A primer or primer pair can be used for sequencing one or both strands of DNA corresponding to the marker gene. A primer can be used in conjunction with a probe, e.g., a nucleic acid probe, e.g., a hybridization probe, to amplify a region of interest prior to sequencing to boost sequence amounts for detection of a mutation in a marker gene. Examples of regions which can be sequenced include an entire gene, transcripts of the gene and a fragment of the gene or the transcript, e.g., one or more of exons or untranslated regions or a portion of a marker comprising a mutation site. Examples of mutations to target for primer selection and sequence or composition analysis can be found in public databases which collect mutation information, such as COSMIC and dbGaP. Some mutations of a marker gene such as KRAS are listed in Example 1 and in Table 5 in the Examples as examples of mutations that can be associated with resistance to proteasome inhibition, e.g., inhibition by a peptidyl boronic acid, e.g., bortezomib or ixazomib citrate.

Sequencing methods are known to one skilled in the art. Examples of methods include the Sanger method, the SEQUENOM™ method and Next Generation Sequencing (NGS) methods. The Sanger method, comprising using electrophoresis, e.g., capillary electrophoresis to separate primer-elongated labeled DNA fragments, can be automated for high-throughput applications. The primer extension sequencing can be performed after PCR amplification of regions of interest. Software can assist with sequence base calling and with mutation identification. SEQUENOM™ MASSARRAY® sequencing analysis (San Diego, Calif.) is a mass-spectrometry method which compares actual mass to expected mass of particular fragments of interest to identify mutations. NGS technology (also called "massively parallel sequencing" and "second generation sequencing") in general provides for much higher throughput than previous methods and uses a variety of approaches (reviewed in Zhang et al. (2011) *J. Genet. Genomics* 38:95-109 and Shendure and Hanlee (2008) *Nature Biotech.* 26:1135-1145). NGS methods can identify low frequency mutations in a marker in a sample. Some NGS methods (see, e.g., GS-FLX Genome Sequencer (Roche Applied Science, Branford, Conn.), Genome analyzer (Illumina, Inc. San Diego, Calif.) SOLID™ analyzer (Applied Biosystems, Carlsbad, Calif.), Polonator G.007 (Dover Systems, Salem, N.H.), HELISCOPE™ (Helicos Biosciences Corp., Cambridge, Mass.)) use cyclic array sequencing, with or without clonal amplification of PCR products spatially separated in a flow cell and various schemes to detect the labeled modified nucleotide that is incorporated by the sequencing enzyme (e.g., polymerase or ligase). In one NGS method, primer pairs can be used in PCR reactions to amplify regions of interest. Amplified regions can be ligated into a concatenated product. Clonal libraries are generated in the flow cell from the PCR or ligated products and further amplified ("bridge" or "cluster" PCR) for single-end sequencing as the polymerase adds a labeled, reversibly terminated base that is imaged in one of four channels, depending on the identity of the labeled base and then removed for the next cycle. Software can aid in the comparison to genomic sequences to identify mutations. Another NGS method is exome sequencing, which focuses on sequencing exons of all genes in the genome. As with other NGS methods, exons can be enriched by capture methods or amplification methods.

Composition of proteins and nucleic acids can be determined by many ways known in the art, such as by treating them in ways that cleave, degrade or digest them and then analyzing the components. Mass spectrometry, electrophoresis and chromatography can separate and define components for comparison. Mutations which cause deletions or insertions can be identified by size or charge differences in these methods. Protein digestion or restriction enzyme nucleic acid digestion can reveal different fragment patterns after some mutations. Antibodies that recognize particular mutant amino acids in their structural contexts can identify and detect these mutations in samples (see below).

In some embodiments, DNA, e.g., genomic DNA corresponding to the wild type or mutated marker can be analyzed both by in situ and by in vitro formats in a biological sample using methods known in the art. DNA can be directly isolated from the sample or isolated after isolating another cellular component, e.g., RNA or protein. Kits are available for DNA isolation, e.g., QIAAMP® DNA Micro Kit (Qiagen, Valencia, Calif.). DNA also can be amplified using such kits.

In another embodiment, mRNA corresponding to the marker can be analyzed both by in situ and by in vitro formats in a biological sample using methods known in the art. An example of a method for measuring expression level is included in the Examples. Many expression detection methods use isolated RNA. For in vitro methods, any RNA isolation technique that does not select against the isolation of mRNA can be utilized for the purification of RNA from tumor cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155). RNA can be isolated using standard procedures (see e.g., Chomczynski and Sacchi (1987) *Anal. Biochem.* 162:156-159), solutions (e.g., trizol, TRI REAGENT® (Molecular Research Center, Inc., Cincinnati, Ohio; see U.S. Pat. No. 5,346,994) or kits (e.g., a QIAGEN Group RNEASY® isolation kit (Valencia, Calif.) or LEUKOLOCK™ Total RNA Isolation System, Ambion division of Applied Biosystems, Austin, Tex.).

Additional steps may be employed to remove DNA from RNA samples. Cell lysis can be accomplished with a non-ionic detergent, followed by microcentrifugation to remove the nuclei and hence the bulk of the cellular DNA. DNA subsequently can be isolated from the nuclei for DNA analysis. In one embodiment, RNA is extracted from cells of the various types of interest using guanidinium thiocyanate lysis followed by CsCl centrifugation to separate the RNA from DNA (Chirgwin et al. (1979) *Biochemistry* 18:5294-99). Poly(A)+RNA is selected by selection with oligo-dT cellulose (see Sambrook et al. (1989) *Molecular Cloning—A Laboratory Manual* (2nd ed.), Cold Spring Harbor Laboratory, Cold Spring Harbor, N.Y.). Alternatively, separation of RNA from DNA can be accomplished by organic extraction, for example, with hot phenol or phenol/chloroform/isoamyl alcohol. If desired, RNAse inhibitors may be added to the lysis buffer. Likewise, for certain cell types, it may be desirable to add a protein denaturation/digestion step to the protocol. For many applications, it is desirable to enrich mRNA with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or SEPHADEX.R™ medium (see Ausubel et al. (1994) *Current Protocols In Molecular Biology*, vol. 2, Current Protocols Publishing, New York). Once bound, poly(A)+mRNA is eluted from the affinity column using 2 mM EDTA/0.1% SDS.

A characteristic of a marker of the invention in a sample, e.g., after obtaining a sample (e.g., a bone marrow sample, a tumor biopsy or a reference sample) from a test subject, can be assessed by any of a wide variety of well known methods for detecting or measuring the characteristic, e.g., of a marker or plurality of markers, e.g., of a nucleic acid (e.g., RNA, mRNA, genomic DNA, or cDNA) and/or translated protein. Non-limiting examples of such methods include immunological methods for detection of secreted, cell-surface, cytoplasmic, or nuclear proteins, protein purification methods, protein function or activity assays, nucleic acid hybridization methods, optionally including "mismatch cleavage" steps (Myers, et al. (1985) *Science* 230:1242) to digest mismatched, i.e. mutant or variant, regions and separation and identification of the mutant or variant from the resulting digested fragments, nucleic acid reverse transcription methods, and nucleic acid amplification methods and analysis of amplified products. These methods include gene array/chip technology, RT-PCR, TAQMAN® gene expression assays (Applied Biosystems, Foster City, Calif.), e.g., under GLP approved laboratory conditions, in situ hybridization, immunohistochemistry, immunoblotting, FISH (flourescence in situ hybridization), FACS analyses, northern blot, southern blot, INFINIUM® DNA analysis Bead Chips (Illumina, Inc., San Diego, Calif.), quantitative PCR, bacterial artificial chromosome arrays, single nucleotide polymorphism (SNP) arrays (Affymetrix, Santa Clara, Calif.) or cytogenetic analyses.

Examples of techniques for detecting differences of at least one nucleotide between two nucleic acids include, but are not limited to, selective oligonucleotide hybridization, selective amplification, or selective primer extension. For example, oligonucleotide probes can be prepared in which the known polymorphic nucleotide is placed centrally (allele- or mutant-specific probes) and then hybridized to target DNA under conditions which permit hybridization only if a perfect match is found (Saiki et al. (1986) *Nature* 324:163); Saiki et al (1989) *Proc. Natl Acad. Sci USA* 86:6230; and Wallace et al. (1979) *Nucl. Acids Res.* 6:3543). Such allele specific oligonucleotide hybridization techniques can be used for the simultaneous detection of several nucleotide changes in different polymorphic or mutated regions of KRAS. For example, oligonucleotides having nucleotide sequences of specific allelic variants or mutants are attached to a solid support, e.g., a hybridizing membrane and this support, e.g., membrane, is then hybridized with labeled sample nucleic acid. Analysis of the hybridization signal thus can reveal the identity of the nucleotides of the sample nucleic acid.

The detection methods of the invention can thus be used to detect RNA, mRNA, protein, cDNA, or genomic DNA, for example, in a biological sample in vitro as well as in vivo. Furthermore, in vivo techniques for detection of a polypeptide or nucleic acid corresponding to a marker of the invention include introducing into a subject a labeled probe to detect the biomarker, e.g., a nucleic acid complementary to the transcript of a biomarker or a labeled antibody, Fc receptor or antigen directed against the polypeptide, e.g., wild type or mutant marker. For example, the antibody can be labeled with a radioactive isotope whose presence and location in a subject can be detected by standard imaging techniques. These assays can be conducted in a variety of ways. A skilled artisan can select from these or other appropriate and available methods based on the nature of the marker(s), tissue sample and mutation in question. Some methods are described in more detail in later sections. Different methods or combinations of methods could be appropriate in different cases or, for instance in different types of tumors or patient populations.

In vitro techniques for detection of a polypeptide corresponding to a marker of the invention include enzyme linked immunosorbent assays (ELISAs), Western blots, protein array, immunoprecipitations, immunohistochemistry and immunofluorescence. In such examples, expression of a marker is assessed using an antibody (e.g., an unlabeled, a radio-labeled, chromophore-labeled, fluorophore-labeled, or enzyme-labeled antibody), an antibody derivative (e.g., an antibody conjugated with a substrate or with the protein or ligand of a protein-ligand pair (e.g., biotin-streptavidin)), or an antibody fragment (e.g., a single-chain antibody, an isolated antibody hypervariable domain, etc.) which binds specifically with a marker protein or fragment thereof, e.g., a protein or fragment comprising a region which can be mutated or a portion comprising a mutated sequence, such as a mutation site, or a mutated residue in its structural context, including a marker protein which has undergone all or a portion of its normal post-translational modification. An antibody can detect a protein with an amino acid sequence selected from the group consisting of SEQ ID NO:3, 6 and 9. Alternatively, an antibody can detect a mutated protein with a variant amino acid sequence selected from the group consisting of a mutant of SEQ ID NO:3 and 6. Residues listed as mutated in public databases such as COSMIC of dbGaP can be prepared in immunogenic compositions for generation of antibodies that will specifically recognize and bind to the mutant residues. Another method can employ pairs of antibodies, wherein one of the pair would bind a marker protein upstream, i.e. N-terminal to the region of expected mutation, e.g., nonsense mutation, point mutation, insertion or deletion and the other of the pair would bind the protein downstream. Wild type protein would bind both antibodies of the pair, but a protein with a nonsense mutation, point mutation, insertion or deletion mutation would bind only the N-terminal antibody of the pair. An assay such as a sandwich ELISA assay could detect a loss of quantity of the wild type protein in the tumor sample, e.g., in comparison to the reference sample, or a standard ELISA would comparison of the levels of binding of the antibodies to infer that a mutation is present in a tumor sample.

Indirect methods for determining the amount or functionality of a protein marker also include measurement of the activity of the protein. For example, a sample, or a protein isolated from the sample or expressed from nucleic acid isolated, cloned or amplified from the sample can be assessed for marker protein activity. For a RAS oncogene, an activating mutation can be measured as reduced GTPase activity or altered binding to RasGAP or a cell membrane.

In some embodiments, the method includes measuring the amount of GLUT4. In some embodiments, an assay to measure GLUT4 expression uses an antibody which binds to SEQ ID NO:9. In some embodiments, quantification of GLUT4 expression measures, in a sample comprising tumor cells, the amount of binding an antibody which binds to SEQ ID NO:9. In some embodiments, the amount of GLUT4 is quantified by immunohistochemistry of a tumor biopsy. In some embodiments, the amount of GLUT4 is quantified by immunohistochemistry of a tumor exudate. In some embodiments, the amount of GLUT4 is determined by a score of antibody binding or staining intensity. In some embodiments, the amount of GLUT4 is determined by comparison of the antibody binding or staining in a tumor cell with a non-tumor cell in the sample comprising tumor cells.

In one embodiment, expression of a marker is assessed by preparing mRNA/cDNA (i.e., a transcribed polynucleotide) from cells in a patient sample, and by hybridizing the mRNA/cDNA with a reference polynucleotide which is a complement of a marker nucleic acid, or a fragment thereof. cDNA can, optionally, be amplified using any of a variety of polymerase chain reaction methods prior to hybridization with the reference polynucleotide. Expression of one or more markers likewise can be detected using quantitative PCR to assess the level of expression of the marker(s). An example of the use of measuring mRNA levels is that an inactivating mutation in a marker gene can result in an altered level of mRNA in a cell. The level can be upregulated due to feedback signaling protein production in view of nonfunctional or absent protein or downregulated due to instability of an altered mRNA sequence. Alternatively, any of the many known methods of detecting mutations or variants (e.g. single nucleotide polymorphisms, deletions, etc., discussed above) of a marker of the invention may be used to detect occurrence of a mutation in a marker gene in a patient.

An example of direct measurement is quantification of transcripts. As used herein, the level or amount of expression refers to the absolute amount of expression of an mRNA encoded by the marker or the absolute amount of expression of the protein encoded by the marker. As an alternative to making determinations based on the absolute expression amount of selected markers, determinations may be based on normalized expression amounts. Expression amount can be normalized by correcting the absolute expression level of a marker upon comparing its expression to the expression of a control marker that is not a marker, e.g., in a housekeeping role that is constitutively expressed. Suitable markers for normalization also include housekeeping genes, such as the actin gene or beta-2 microglobulin. Reference markers for data normalization purposes include markers which are ubiquitously expressed and/or whose expression is not regulated by oncogenes. Constitutively expressed genes are known in the art and can be identified and selected according to the relevant tissue and/or situation of the patient and the analysis methods. Such normalization allows one to compare the expression level in one sample, to another sample, e.g., between samples from different times or different subjects. Further, the expression level can be provided as a relative expression level. The baseline of a genomic DNA sample, e.g., diploid copy number, can be determined by measuring amounts in cells from subjects without a tumor or in non-tumor cells from the patient. To determine a relative amount of a marker or marker set, the amount of the marker or marker set is determined for at least 1, or 2, 3, 4, 5, or more samples, e.g., 7, 10, 15, 20 or 50 or more samples in order to establish a baseline, prior to the determination of the expression level for the sample in question. To establish a baseline measurement, the mean amount or level of each of the markers or marker sets assayed in the larger number of samples is determined and this is used as a baseline expression level for the biomarkers or biomarker sets in question. The amount of the marker or marker set determined for the test sample (e.g., absolute level of expression) is then divided by the baseline value obtained for that marker or marker set. This provides a relative amount and aids in identifying abnormal levels of marker protein activity.

Probes based on the sequence of a nucleic acid molecule of the invention can be used to detect transcripts or genomic sequences corresponding to one or more markers of the invention. The probe can comprise a label group attached thereto, e.g., a radioisotope, a fluorescent compound, an enzyme, or an enzyme co-factor. Such probes can be used as part of a diagnostic test kit for identifying cells or tissues which express the protein, such as by measuring levels of a nucleic acid molecule encoding the protein in a sample of cells from a subject, e.g., detecting mRNA levels or determining whether a gene encoding the protein has been mutated or deleted.

In addition to the nucleotide sequences described in the database records described herein, it will be appreciated by those skilled in the art that DNA sequence polymorphisms that lead to changes in the amino acid sequence can exist within a population (e.g., the human population). Such genetic polymorphisms can exist among individuals within a population due to naturally occurring allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

Primers or nucleic acid probes comprise a nucleotide sequence complementary to a specific a marker or a mutated region thereof and are of sufficient length to selectively hybridize with a marker gene or nucleic acid associated with a marker gene, e.g., they can bind to the nucleic acid with base sequence specificity and remain bound, e.g., after washing. Primers and probes can be used to aid in the isolation and sequencing of marker nucleic acids. In one embodiment, the primer or nucleic acid probe, e.g., a substantially purified oligonucleotide, an isolated nucleic acid, comprises a region having a nucleotide sequence which hybridizes, e.g., under stringent conditions to about 6, 8, 10, 12, or 15, 20, 25, 30, 40, 50, 60, 75, 100, 200, 350, 500 or more consecutive nucleotides of a marker gene or a region comprising a mutation in a marker gene or transcript therefrom or a complement thereof. In another embodiment, the primer or nucleic acid probe is capable of hybridizing to a marker nucleic acid comprising a nucleotide sequence of any sequence set forth in any of SEQ ID NOs:1, 2, 4, 5, 7, 8 or a sequence on chromosome 1p, e.g., from base pair 115247085 to 115259515 and chromosome 12p, e.g., from base pair 25358180 to 25403854, or a complement of any of the foregoing. For example, a primer or nucleic acid probe comprising a nucleotide sequence of at least about 15 consecutive nucleotides, at least about 20 consecutive nucleotides, at least about 25 consecutive nucleotides, at least about 35 consecutive nucleotides, at least about 50 consecutive nucleotides, or having from about 15 to about 20 consecutive nucleotides set forth in any of SEQ ID NOs: 1, 2, 4, 5, 7, 8, or a sequence on chromosome 1p from base pair 115247085 to 115259515 or chromosome 12p, from base pair 25358180 to 25403854, or a complement of any of the foregoing are provided by the invention. Primers or nucleic acid probes having a sequence of more than about 25, 40 or 50 nucleotides are also within the scope of the invention. In another embodiment, a primer or nucleic acid probe can have a sequence at least 70%, at least 75%, 80% or 85%, or at least, 90%, 95% or 97% identical to the nucleotide sequence of any sequence set forth in any of SEQ ID NOs: 1, 2, 4, 5, 7, 8, or a sequence on chromosome 1p from base pair 115247085 to 115259515, chromosome 12p from base pair 25358180 to 25403854, or a complement of any of the foregoing. Nucleic acid analogs can be used as binding sites for hybridization. An example of a suitable nucleic acid analogue is peptide nucleic acid (see, e.g., Egholm et al., *Nature* 363:566 568 (1993); U.S. Pat. No. 5,539,083).

In some embodiments, a nucleic acid probe can be designed to bind to the wild type sequence, so the presence of a mutation in that region can cause a decrease, e.g., measurable decrease, in binding or hybridization by that probe. In another embodiment, a nucleic acid probe can be designed to bind to a mutant sequence, so the presence of a mutation in that region can cause an increase in binding or hybridization by that probe. In other embodiments, a probe and primer set or a primer pair can be designed to bracket a region in a marker that can have a mutation so amplification based on that set or pair can result in nucleic acids which can be sequenced to identify the mutation.

Primers or nucleic acid probes can be selected using an algorithm that takes into account binding energies, base composition, sequence complexity, cross-hybridization binding energies, and secondary structure (see Friend et al., International Patent Publication WO 01/05935, published Jan. 25, 2001; Hughes et al., *Nat. Biotech.* 19:342-7 (2001). Useful primers or nucleic acid probes of the invention bind sequences which are unique for each transcript, e.g., target mutated regions and can be used in PCR for amplifying, detecting and sequencing only that particular nucleic acid, e.g., transcript or mutated transcript. Examples of some mutations of a marker gene, e.g., KRAS are found in Example 1 and in Table 5 in the Examples. Other mutations are described in reference articles cited herein and in public databases described herein. One of skill in the art can design primers and nucleic acid probes for the markers disclosed herein or related markers with similar characteristics, e.g., markers on the chromosome loci, or mutations in different regions of the same marker gene described herein, using the skill in the art, e.g., adjusting the potential for primer or nucleic acid probe binding to standard sequences, mutants or allelic variants by manipulating degeneracy or GC content in the primer or nucleic acid probe. Computer programs that are well known in the art are useful in the design of primers with the required specificity and optimal amplification properties, such as Oligo version 5.0 (National Biosciences, Plymouth, Minn.). While perfectly complementary nucleic acid probes and primers can be used for detecting the markers described herein and mutants, polymorphisms or alleles thereof, departures from complete complementarity are contemplated where such departures do not prevent the molecule from specifically hybridizing to the target region. For example, an oligonucleotide primer may have a non-complementary fragment at its 5' end, with the remainder of the primer being complementary to the target region. Alternatively, non-complementary nucleotides may be interspersed into the nucleic acid probe or primer as long as the resulting probe or primer is still capable of specifically hybridizing to the target region.

An indication of treatment outcome can be assessed by studying the amount of 1 marker, 2 markers, 3 markers or 4 markers, or more, e.g., 5, 6, 7, 8, 9, 10, 15, 20, or 25 markers, portions comprising mutation sites or mutated portions thereof e.g., marker genes which participate in or interact with the RAS pathway e.g., genes which control the cell cycle, e.g., which can be inactivated by somatic mutation in cancer, or which participate in glucose transport. Markers can be studied in combination with another measure of treatment outcome, e.g., biochemical markers (e.g., M protein in myeloma, kidney health marker such as proteinuria, serum levels of C-reactive protein or cytokeratin 19, cytokeratin fragment 21-1 (CYFRA21-1) for NSCLC) or serum levels of carbohydrate antigen 19-9 (CA 19-9) or metabolic profiling for pancreatic cancer) or histology markers (e.g., blast count, number of mitotic figures per unit area, depth measurement of invasion of melanoma tumors or head and neck, e.g., esophageal tumors).

Statistical methods can assist in the determination of treatment outcome upon measurement of the amount of markers, e.g., measurement of DNA, RNA or protein. The amount of one marker can be measured at multiple time-points, e.g., before treatment, during treatment, after treatment with an agent, e.g., a proteasome inhibitor. To determine the progression of change in expression of a marker from a baseline, e.g., over time, the expression results can be analyzed by a repeated measures linear regression model (Littell, Miliken, Stroup, Wolfinger, Schabenberger (2006) *SAS for Mixed Models*, $2^{nd}$ edition. SAS Institute, Inc., Cary, N.C.)):

$$Y_{ijk}-Y_{ij0}=Y_{ij0}+\text{treatment}_i+\text{day}_k+(\text{treatment}*\text{day})_{ik}+\epsilon_{ijk} \quad \text{Equation 1}$$

where $Y_{ijk}$ is the $\log_2$ transformed expression (normalized to the housekeeping genes) on the $k^{th}$ day of the $j^{th}$ animal in the $i^{th}$ treatment, $Y_{ij0}$ is the defined baseline $\log_2$ transformed expression (normalized to the housekeeping genes) of the $j^{th}$ animal in the $i^{th}$ treatment, $\text{day}_k$ is treated as a categorical variable, and $\epsilon_{ijk}$ is the residual error term. A covariance matrix (e.g., first-order autoregressive, compound symmetry, spatial power law) can be specified to model the repeated measurements on each animal over time. Furthermore, each treatment time point can be compared back to the same time point in the vehicle group to test whether the treatment value was significantly different from vehicle.

A number of other methods can be used to analyze the data. For instance, the relative expression values could be analyzed instead of the cycle number. These values could be examined as either a fold change or as an absolute difference from baseline. Additionally, a repeated-measures analysis of variance (ANOVA) could be used if the variances are equal across all groups and time points. The observed change from baseline at the last (or other) time point could be analyzed using a paired t-test, a Fisher exact test (p-value=$\Sigma P(X=x)$ from x=1 to the number of situations, e.g., wild type or mutations, tested that show sensitivity, e.g., favorable outcome, or nonresponse to proteasome inhibition) for testing significance of data of small sample sizes, or a Wilcoxon signed rank test if the data is not normally distributed, to compare whether a tumor patient was significantly different from a normal subject.

A difference in amount from one timepoint to the next or from the tumor sample to the normal sample can indicate prognosis of treatment outcome. A baseline level can be determined by measuring expression at 1, 2, 3, 4, or more times prior to treatment, e.g., at time zero, one day, three days, one week and/or two weeks or more before treatment. Alternatively, a baseline level can be determined from a number of subjects, e.g., normal subjects or patients with the same health status or disorder, who do not undergo or have not yet undergone the treatment, as discussed above. Alternatively, one can use expression values deposited with the Gene Expression Omnibus (GEO) program at the National Center for Biotechnology Information (NCBI, Bethesda, Md.). For example, datasets of myeloma mRNA expression amounts sampled prior to proteasome inhibition therapy include GEO Accession number GSE9782, also analyzed in Mulligan, et al. (2006) *Blood* 109:3177-88 and GSE6477, also analyzed by Chng et al. (2007) *Cancer Res.* 67:292-9. To test the effect of the treatment on the tumor, the expression of the marker can be measured at any time or multiple times after some treatment, e.g., after 1 day, 2 days, 3 days, 5 days, 1 week, 2 weeks, 3 weeks, one 3 week treatment cycle, 4 weeks, one 4 week treatment cycle, 1 month, one 5 week treatment cycle, 2 months, 3 months, 5 cycles and/or 6 or more months of treatment. For example, the amount of a marker can be measured once after some treatment, or at multiple intervals, e.g., 1-week, 2-week, 4-week, one 3-week, 4-week or 5-week cycle, two cycles, 2-month, 3-month, five cycles or longer intervals during treatment. A treatment cycle for bortezomib can be found in the publications of treatment with the agents, or in the product inserts. A treatment cycle for ixazomib citrate (MLN9708) can be found at the clinical trials website maintained by the U.S. National Institutes of Health, Bethesda, Md. Conversely, to determine onset of progressive disease after stopping the administration of a therapeutic regimen, the amount of the marker can be measured at any time or multiple times after, e.g., 1 day, 2 days, 3 days, 5 days, 1 week, 2 weeks, 3 weeks, 4 weeks, 1 month, 2 months, 3 months and/or 6 or more months after the last treatment. The measurement of a marker after treatment can be compared to the same marker measurement at the end of treatment. One of skill in the art would determine the timepoint or timepoints to assess the amount of the marker depending on various factors, e.g., the pharmacokinetics of the treatment, the treatment duration, pharmacodynamics of the treatment, age of the patient, the nature of the disorder or mechanism of action of the treatment. A trend in the negative direction or a decrease in the amount relative to baseline or a pre-determined standard of expression of a marker of sensitivity to proteasome inhibition therapy indicates a decrease in response of the tumor to the therapy, e.g., increase in resistance. A trend toward a favorable outcome relative to the baseline or a pre-determined standard of expression of a marker of treatment outcome indicates usefulness of the therapeutic regimen or continued benefit of the therapy.

Any marker, e.g., marker gene or combination of marker, e.g., marker genes of the invention, or mutations thereof as well as any known markers in combination with the markers, e.g., marker genes of the invention, may be used in the compositions, kits, and methods of the present invention. In general, markers are selected for as great as possible difference between the characteristic, e.g., size, sequence, composition, activity or amount of the marker in samples comprising tumor cells and the characteristic, e.g., size, sequence, composition, activity or amount of the same marker in control cells. Although this difference can be as small as the limit of detection of the method for assessing the amount of the marker, in another embodiment, the difference can be at least greater than the standard error of the assessment method. In the case of RNA or protein amount, a difference can be at least 1.5-, 2-, 3-, 4-, 5-, 6-, 7-, 8-, 9-, 10-, 15-, 20-, 25-, 100-, 500-, 1000-fold or greater. "Low" RNA or protein amount can be that expression relative to the overall mean across tumor samples (e.g., solid tumor) is low. In the case of amount of DNA, e.g., copy number, the amount is 0, 1, 2, 3, 4, 5, 6, or more copies. A deletion causes the copy number to be 0 or 1; an amplification causes the copy number to be greater than 2. The difference can be qualified by a confidence level, e.g., $p<0.05$, $p<0.02$, $p<0.01$ or lower p-value.

Measurement of more than one marker, e.g., a set of 2, 3, 4, 5, 6, 7, 8, 9, 10, 12, 15, 20, or 25 or more markers, e.g., a set of markers comprising a KRAS marker, can provide an expression profile or a trend indicative of treatment outcome. In some embodiments, the marker set comprises no more than 2, 3, 4, 5, 6, 7, 8, 9, 10, 12, 15, 20, or 25 markers.

In some embodiments, the marker set includes a plurality of chromosome loci, a plurality of marker genes, or a plurality of markers of one or more marker genes (e.g., nucleic acid and protein, genomic DNA and mRNA, or various combinations of markers described herein). Analysis of treatment outcome through assessing the amount of markers in a set can be accompanied by a statistical method, e.g., a weighted voting analysis which accounts for variables which can affect the contribution of the amount of a marker in the set to the class or trend of treatment outcome, e.g., the signal-to-noise ratio of the measurement or hybridization efficiency for each marker. A marker set, e.g., a set of 2, 3, 4, 5, 6, 7, 8, 9, 10, 12, 15, 20, or 25 or more markers, can comprise a primer, probe or primers to analyze at least one marker DNA or RNA described herein, e.g., a marker on chromosome 1p from base pair 115247085 to 115259515, chromosome 12p from base pair 25358180 to 25403854, NRAS, KRAS, GLUT4, or a complement of any of the foregoing. A marker set, e.g., a set of 2, 3, 4, 5, 6, 7, 8, 9, 10, 12, 15, 20, or 25 or more markers, can comprise a primer, probe or primers to detect at least one or at least two or more markers, or at least 2, 3, 4, 5, 6, 7, 8, 9, 10, 12, 15, 20, or 25 or more mutations on the markers e.g., of NRAS and/or KRAS and/or GLUT4. In another embodiment, a marker set can comprise wild type KRAS nucleic acid or probes or primers comprising wild type versions of mutated regions, or the complement thereof or capable of aiding in the identification of the sequence of mutated regions of KRAS, e.g., codon 12, codon 13 or codon 61 of SEQ ID NO:2. In some embodiments, a marker set can comprise a probe or primer capable of aiding in the identification of the sequence of mutated codon 146 of KRAS. Selected marker sets can be assembled from the markers provided herein or selected from among markers using methods provided herein and analogous methods known in the art. A way to qualify a new marker for use in an assay of the invention is to correlate DNA copy number in a sample comprising tumor cells with differences in expression (e.g., fold-change from baseline) of a marker, e.g., a marker gene. A useful way to judge the relationship is to calculate the coefficient of determination $r2$, after solving for r, the Pearson product moment correlation coefficient and/or preparing a least squares plot, using standard statistical methods. A correlation can analyze DNA copy number versus the level of expression of marker, e.g., a marker gene. A gene product can be selected as a marker if the result of the correlation ($r2$, e.g., the linear slope of the data in this analysis), is at least 0.1-0.2, at least 0.3-0.5, or at least 0.6-0.8 or more. Markers can vary with a positive correlation to response, TTP or survival (i.e., change expression levels in the same manner as copy number, e.g., decrease when copy number is decreased). Markers which vary with a negative correlation to copy number (i.e., change expression levels in the opposite manner as copy number levels, e.g., increase when copy number is decreased) provide inconsistent determination of outcome.

Another way to qualify a new marker for use in the assay would be to assay the expression of large numbers of markers in a number of subjects before and after treatment with a test agent. The expression results allow identification of the markers which show large changes in a given direction after treatment relative to the pre-treatment samples. One can build a repeated-measures linear regression model to identify the genes that show statistically significant changes or differences. To then rank these significant genes, one can calculate the area under the change from e.g., baseline vs time curve. This can result in a list of genes that would show the largest statistically significant changes.

Then several markers can be combined together in a set by using such methods as principle component analysis, clustering methods (e.g., k-means, hierarchical), multivariate analysis of variance (MANOVA), or linear regression techniques. To use such a gene (or group of genes) as a marker, genes which show 2-, 2.5-, 3-, 3.5-, 4-, 4.5-, 5-, 7-,10-fold, or more differences of expression from baseline would be included in the marker set. An expression profile, e.g., a composite of the expression level differences from baseline or reference of the aggregate marker set would indicate at trend, e.g., if a majority of markers show a particular result, e.g., a significant difference from baseline or reference, e.g., 60%, 70%, 80%, 90%, 95% or more markers; or more markers, e.g., 10% more, 20% more, 30% more, 40% more, show a significant result in one direction than the other direction.

In embodiments when the compositions, kits, and methods of the invention are used for characterizing treatment outcome in a patient, the marker or set of markers of the invention is selected such that a significant result is obtained in at least about 20%, at least about 40%, 60%, or 80%, or in substantially all patients treated with the test agent. The marker or set of markers of the invention can be selected such that a positive predictive value (PPV) of greater than about 10% is obtained for the general population and additional confidence in a marker can be inferred when the PPV is coupled with an assay specificity greater than 80%.

Therapeutic Agents

The markers and marker sets of the present invention can be used to assess the likelihood of favorable outcome (e.g., sensitivity to a therapeutic agent) in patients, e.g., cancer patients, e.g., patients having a solid tumor cancer (e.g., lung cancer, such as non-small cell lung cancer (NSCLC), or adenocarcinoma of the lung, colon cancer, pancreatic cancer or prostate cancer), based on values or changes in at least one characteristic, e.g., composition or amount of a marker or markers of the invention. Using this prediction, cancer therapies can be evaluated to design a therapy regimen best suitable for a patient either predicted to have a favorable outcome or an unfavorable outcome.

In particular, the methods can be used to predict patient sensitivity to proteasome inhibitors as described in earlier sections. The agents tested in the present methods can be a single agent or a combination of agents. The methods of the invention include combination of proteasome inhibition therapy with other or additional agents, a "combination agent", e.g., selected from the group consisting of chemotherapeutic agents. For example, the present methods can be used to determine whether a single chemotherapeutic agent, such as a proteasome inhibitor, such as a peptidyl boronic acid (e.g., MLN9708) or a peptidyl epoxy ketone can be used to treat a cancer or whether a one or more agents should be used in combination with the proteasome inhibitor (e.g., MLN9708). Useful combination agents can include agents that have different mechanisms of action, e.g., the use of an anti-mitotic agent or an alkylating agent in combination with a proteasome inhibitor. Proteasome inhibitors are described in an earlier section.

The methods of the invention include combination of proteasome inhibition therapy with glucocorticoid inhibition therapy. In certain applications of the invention, the combination agent used in combination with a proteasome inhibitor (e.g., MLN9708) is a glucocorticoid agent (e.g., dexamethasone, hydrocortisone, predisolone, prednisone, or triamcinolone). Other therapeutic agents for use in combination with proteasome inhibition therapy include chemotherapeutic agents. A "chemotherapeutic agent" is intended to include chemical reagents which inhibit the growth of proliferating cells or tissues wherein the growth of such cells or tissues is undesirable. Chemotherapeutic agents such as anti-metabolic agents, e.g., Ara AC, 5-FU and methotrexate, antimitotic agents, e.g., taxanes, such as paclitaxel and docetaxel, vinblastine and vincristine, alkylating agents, e.g., melphanlan, Carmustine (BCNU) and nitrogen mustard, Topoisomerase II inhibitors, e.g., VW-26, topotecan and Bleomycin, strand-breaking agents, e.g., doxorubicin and Mitoxantrone (DHAD), Topoisomerase I inhibitors, e.g., topotecan and irinotecan, tyrosine kinase inhibitors, e.g., sorafenib or erlotinib, angiogenesis inhibitors/immunomodulatory agents, e.g., thalidomide, lenalidomide and pomalidomide, cross-linking agents, e.g., cisplatin, oxaliplatin and carboplatin (CBDCA), radiation and ultraviolet light and are well known in the art (see e.g., Gilman A. G., et al., *The Pharmacological Basis of Therapeutics*, 8th Ed., Sec 12:1202-1263 (1990)), and are typically used to treat neoplastic diseases. Examples of chemotherapeutic agents generally employed in chemotherapy treatments are listed below in Table 2.

TABLE 2

Chemotherapeutic Agents

| CLASS | TYPE OF AGENT | NONPROPRIETARY NAMES (OTHER NAMES) |
|---|---|---|
| Alkylating | Nitrogen Mustards | Mechlorethamine ($HN_2$) |
| | | Cyclophosphamide |
| | | Ifosfamide |
| | | Melphalan (L-sarcolysin) |
| | | Chlorambucil |
| | Ethylenimines And Methylmelamines | Hexamethylmelamine Thiotepa |
| | Alkyl Sulfonates | Busulfan |
| Alkylating | Nitrosoureas | Carmustine (BCNU) |
| | | Lomustine (CCNU) |
| | | Semustine (methyl-CCNU) |
| | | Streptozocin (streptozotocin) |
| Alkylating | Triazenes | Decarbazine (DTIC; dimethyltriazenoimidazolecarboxamide) |
| | Alkylator | cis-diamminedichloroplatinum II (CDDP) |
| Antimetabolites | Folic Acid Analogs | Methotrexate (amethopterin) |
| | | leucovorin |
| | | pemetrexed |
| | Pyrimidine Analogs | Fluorouracil ('5-fluorouracil; 5-FU) |
| | | Floxuridine (fluorode-oxyuridine; FUdR) |
| | | Cytarabine (cytosine arabinoside) |
| | | gemcitabine |
| | Purine Analogs and Related Inhibitors | Mercaptopuine (6-mercaptopurine; 6-MP) |
| | | Thioguanine (6-thioguanine; TG) |
| | | Pentostatin (2'-deoxycoformycin) |
| Natural Products | Microtubule-acting agents | Vinblastin (VLB) |
| | | Vincristine |
| | | vinorelbine |
| | | TAXOL (paclitaxel) |
| | | Taxotere (docetaxel) |
| | Topoisomerase Inhibitors | Etoposide |
| | | Teniposide |
| | | Camptothecin |
| | | Topotecan |
| | | 9-amino-campotothecin CPT-11 |
| | Antibiotics | Dactinomycin (actinomycin D) |
| | | Adriamycin |
| | | Daunorubicin (daunomycin; rubindomycin) |
| | | Doxorubicin |
| | | Bleomycin |
| | | Plicamycin (mithramycin) |
| | | Mitomycin (mitomycin C) |

TABLE 2-continued

Chemotherapeutic Agents

| CLASS | TYPE OF AGENT | NONPROPRIETARY NAMES (OTHER NAMES) |
|---|---|---|
| Natural Products | Enzymes | L-Asparaginase |
| | Biological Response Modifiers | Interfon alfa |
| | | Interleukin 2 |
| | Platinum Coordination Complexes | cis-diamminedichloroplatinum II (CDDP) |
| | | Carboplatin |
| | Anthracendione | Mitoxantrone |
| | Substituted Urea | Hydroxyurea |
| Miscellaneous Agents | Methyl Hydraxzine Derivative | Procarbazine (N-methylhydrazine,(MIH) |
| | Adrenocortical Suppressant | Mitotane (o,p'-DDD) |
| | | Aminoglutethimide |
| Hormones and Antagonists | Progestins | Hydroxyprogesterone caproate |
| | | Medroxyprogesterone acetate |
| | | Megestrol acetate |
| | Estrogens | Diethylstilbestrol |
| | | Ethinyl estradiol |
| | Antiestrogen | Tamoxifen |
| | Androgens | Testosterone propionate |
| | | Fluoxymesterone |
| | Antiandrogen | Flutamide |
| | Gonadotropin-releasing Hormone analog | Leuprolide |

The agents tested in the present methods can be a single agent or a combination of agents. For example, the present methods can be used to determine whether a single chemotherapeutic agent, such as a proteasome inhibitor, can be used to treat a cancer or whether a combination of two or more agents can be used in combination with a proteasome inhibitor (e.g., bortezomib or ixazomib citrate). Useful combination agents can include agents that have different mechanisms of action, e.g., the use of an anti-mitotic agent in combination with an alkylating agent and a proteasome inhibitor. In one example, a proteasome inhibitor is administered in combination with adriamycin. In another embodiment, a proteasome inhibitor is administered with taxotere.

In some embodiments, a proteasome inhibitor is administered in combination with at least one combination agent. In some embodiments, the combination agent is selected from the group consisting of irinotecan, CPT-11, cisplatin, carboplatin, docetaxel, gemcitabine, etoposide, pemetrexed and vinorelbine. In some embodiments, the combination agent is selected from the group consisting of 5-fluorouracil or a variant thereof, irinotecan, oxaliplatin and leucovorin.

The agents disclosed herein may be administered by any route, including intradermally, subcutaneously, orally, intraarterially or intravenously. In one embodiment, administration will be by the intravenous route. Parenteral administration can be provided in a bolus or by infusion.

The concentration of a disclosed compound in a pharmaceutically acceptable mixture will vary depending on several factors, including the dosage of the compound to be administered, the pharmacokinetic characteristics of the compound(s) employed, and the route of administration. The agent may be administered in a single dose or in repeat doses. Treatments may be administered daily or more frequently depending upon a number of factors, including the overall health of a patient, and the formulation and route of administration of the selected compound(s).

Detection Methods

A general principle of prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay. One example of such some embodiments includes use of an array or chip which contains a predictive marker or marker set anchored for expression analysis of the sample.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite. One skilled in the art will know many other suitable carriers for binding antibody or antigen, and will be able to adapt such support for use with the present invention. For example, protein isolated from cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In some embodiments, the probe, when it is the unanchored assay component, can be labeled for the purpose of detection and readout of the assay, either directly or indirectly, with detectable labels discussed herein and which are well-known to one skilled in the art. The term "labeled", with regard to the probe (e.g., nucleic acid or antibody), is intended to encompass direct labeling of the probe by coupling (i.e., physically linking) a detectable substance to the probe, as well as indirect labeling of the probe by reactivity with another reagent that is directly labeled. An example of indirect labeling includes detection of a primary antibody using a fluorescently labeled secondary antibody. It is also possible to directly detect marker/probe complex formation without further manipulation or labeling of either component (marker or probe), for example by utilizing the technique of fluorescence energy transfer (FET, see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C. (1991) Anal. Chem. 63:2338-2345 and Szabo et al. (1995) Curr. Opin. Struct. Biol. 5:699-705). As used herein, "BIA" or "surface plasmon resonance" is a technology for studying biospecific interactions in real time, without labeling any of the interactants (e.g., BIACORE™). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P. (1993) Trends Biochem Sci. 18:284-7). Standard chromatographic techniques also can be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H. (1998) J. Mol. Recognit. 11:141-8; Hage, D. S., and Tweed, S. A. (1997) J. Chromatogr. B. Biomed. Sci. Appl. 699:499-525). Gel electrophoresis may also be employed to separate complexed assay components from unbound components (see, e.g., Ausubel et al., ed., Current Protocols in Molecular Biology, John Wiley & Sons, New York, 1987-1999). In this technique, protein or nucleic acid complexes are separated based on size or charge, for example. In some embodiments, non-denaturing gel matrix materials and conditions in the absence of reducing agent are used in order to maintain the binding interaction during the electrophoretic process. Appropriate conditions to the particular assay and components thereof will be well known to one skilled in the art.

The isolated mRNA can be used in hybridization or amplification assays that include, but are not limited to, Southern or Northern analyses, polymerase chain reaction and TAQMAN® gene expression assays (Applied Biosystems, Foster City, Calif.) and probe arrays. One diagnostic method for the detection of mRNA levels involves contacting the isolated mRNA with a nucleic acid molecule (probe) that can hybridize to the mRNA encoded by the gene being detected. Nucleic acids comprising mutations of marker genes can be used as probes or primers. The nucleic acid probes or primers of the invention can be single stranded DNA (e.g., an oligonucleotide), double stranded DNA (e.g., double stranded oligonucleotide) or RNA. Primers of the invention refer to nucleic acids which hybridize to a nucleic acid sequence which is adjacent to the region of interest and is extended or which covers the region of interest. A nucleic acid probe can be, for example, a full-length cDNA, or a portion thereof, such as an oligonucleotide of at least 7, 15, 20, 25, 30, 50, 75, 100, 125, 150, 175, 200, 250 or 500 or more consecutive nucleotides of the marker and sufficient to specifically hybridize under stringent conditions to a mRNA or genomic DNA encoding a marker of the present invention. The exact length of the nucleic acid probe will depend on many factors that are routinely considered and practiced by the skilled artisan. Nucleic acid probes of the invention may be prepared by chemical synthesis using any suitable methodology known in the art, may be produced by recombinant technology, or may be derived from a biological sample, for example, by restriction digestion. Other suitable probes for use in the diagnostic assays of the invention are described herein. The probe can comprise a label group attached thereto, e.g., a radioisotope, a fluorescent compound, an enzyme, an enzyme co-factor, a hapten, a sequence tag, a protein or an antibody. The nucleic acids can be modified at the base moiety, at the sugar moiety, or at the phosphate backbone. An example of a nucleic acid label is incorporated using SUPER™ Modified Base Technology (Nanogen, Bothell, Wash., see U.S. Pat. No. 7,045,610). The level of expression can be measured as general nucleic acid levels, e.g., after measuring the amplified DNA levels (e.g. using a DNA intercalating dye, e.g., the SYBR green dye (Qiagen Inc., Valencia, Calif.) or as specific nucleic acids, e.g., using a probe based design, with the probes labeled. TAQMAN® assay formats can use the probe-based design to increase specificity and signal-to-noise ratio.

Such primers or probes can be used as part of a diagnostic test kit for identifying cells or tissues which express the protein, such as by measuring amounts of a nucleic acid molecule transcribed in a sample of cells from a subject, e.g., detecting transcript, mRNA levels or determining whether a gene encoding the protein has been mutated or deleted. Hybridization of an RNA or a cDNA with the nucleic acid probe can indicate that the marker in question is being expressed. The invention further encompasses detecting nucleic acid molecules that differ, due to degeneracy of the genetic code, from the nucleotide sequence of nucleic acids encoding a marker protein (e.g., protein having the sequence of the SEQ ID NO:3, 6 or 9) and thus encode the same protein. It will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. Such natural allelic variations can typically result in 1-5% variance in the nucleotide sequence of a given gene. Alternative alleles can be identified by sequencing the gene of interest in a number of different individuals, e.g., normal samples from individuals. This can be readily carried out by using hybridization probes to identify the same genetic locus in a variety of individuals. Detecting any and all such nucleotide variations and resulting amino acid polymorphisms or variations that are the result of natural allelic variation and that do not alter the functional activity are intended to be within the scope of the invention. In addition, it will be appreciated that DNA polymorphisms that affect RNA expression levels can also exist that may affect the overall expression level of that gene (e.g., by affecting regulation or degradation).

As used herein, the term "hybridizes" is intended to describe conditions for hybridization and washing under which nucleotide sequences that are significantly identical or homologous to each other remain hybridized to each other. In some embodiments, the conditions are such that sequences at least about 70%, at least about 80%, at least about 85%, 90% or 95% identical to each other remain hybridized to each other for subsequent amplification and/or detection. Stringent conditions vary according to the length of the involved nucleotide sequence but are known to those skilled in the art and can be found or determined based on teachings in *Current Protocols in Molecular Biology*, Ausubel et al., eds., John Wiley & Sons, Inc. (1995), sections 2, 4 and 6. Additional stringent conditions and formulas for determining such conditions can be found in *Molecular Cloning: A Laboratory Manual*, Sambrook et al., Cold Spring Harbor Press, Cold Spring Harbor, N.Y. (1989), chapters 7, 9 and 11. A non-limiting example of stringent hybridization conditions for hybrids that are at least 10 basepairs in length includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A non-limiting example of highly stringent hybridization conditions for such hybrids includes hybridization in 1×SSC, at about 65-70° C. (or hybridization in 1×SSC plus 50% formamide at about 42-50° C.) followed by one or more washes in 0.3×SSC, at about 65-70° C. A non-limiting example of reduced stringency hybridization conditions for such hybrids includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. Another example of stringent hybridization conditions are hybridization in 6× sodium chloride/sodium citrate (SSC) at about 45° C., followed by one or more washes in 0.2×SSC, 0.1% SDS at 50-65° C. A further example of stringent hybridization buffer is hybridization in 1 M NaCl, 50 mM 2-(N-morpholino)ethanesulfonic acid (MES) buffer (pH 6.5), 0.5% sodium sarcosine and 30% formamide. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.)=2(# of A+T bases)+4(# of G+C bases). For hybrids between 18 and 49 base pairs in length, $T_m$(° C.)=81.5+16.6($\log_{10}$[Na$^+$]) 0.41(% G+C)−(600/N), where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, polyvinylpyrrolidone (PVP) and the like. When using nylon membranes, in particular, an additional non-limiting example of stringent hybridization conditions is hybridization in 0.25-0.5M NaH$_2$PO$_4$, 7% SDS at about 65° C., followed by one or more washes at 0.02M NaH$_2$PO$_4$, 1% SDS at 65° C., see e.g., Church and Gilbert (1984) *Proc. Natl. Acad. Sci. USA* 81:1991-1995, (or alternatively 0.2×SSC, 1% SDS). A primer or nucleic acid probe can be used alone in a detection method, or a primer can be used together with at least one other primer or nucleic acid probe in a detection method. Primers can also be used to amplify at least a portion of a nucleic acid. In some embodiments, a portion of a nucleic acid marker comprising a mutation site is amplified. Nucleic acid probes of the invention refer to nucleic acids which hybridize to the region of interest and which are not further extended. For example, a nucleic acid probe is a nucleic acid which specifically hybridizes to a mutant region of a biomarker, and which by hybridization or absence of hybridization to the DNA of a patient or the type of hybrid formed can be indicative of the presence or identity of the mutation of the biomarker or the amount of marker activity.

In one format, the RNA is immobilized on a solid surface and contacted with a probe, for example by running the isolated RNA on an agarose gel and transferring the RNA from the gel to a membrane, such as nitrocellulose. In an alternative format, the nucleic acid probe(s) are immobilized on a solid surface and the RNA is contacted with the probe(s), for example, in an AFFYMETRIX® gene chip array or a SNP chip (Santa Clara, Calif.) or customized array using a marker set comprising at least one marker indicative of treatment outcome. A skilled artisan can readily adapt known RNA and DNA detection methods for use in detecting the amount of the markers of the present invention. For example, the high density microarray or branched DNA assay can benefit from a higher concentration of tumor cell in the sample, such as a sample which had been modified to isolate tumor cells as described in earlier sections. In a related embodiment, a mixture of transcribed polynucleotides obtained from the sample is contacted with a substrate having fixed thereto a polynucleotide complementary to or homologous with at least a portion (e.g., at least 7, 10, 15, 20, 25, 30, 40, 50, 100, 500, or more consecutive nucleotide residues) of a marker nucleic acid. If polynucleotides complementary to or homologous with the marker are differentially detectable on the substrate (e.g., detectable using different chromophores or fluorophores, or fixed to different selected positions), then the levels of expression of a plurality of markers can be assessed simultaneously using a single substrate (e.g., a "gene chip" microarray of polynucleotides fixed at selected positions). In some embodiments when a method of assessing marker expression is used which involves hybridization of one nucleic acid with another, the hybridization can be performed under stringent hybridization conditions.

An alternative method for determining the amount of RNA corresponding to a marker of the present invention in a sample involves the process of nucleic acid amplification, e.g., by RT-PCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to about 30 nucleotides in length and flank a region from about 50 to about 200 nucleotides in length. Under appropriate conditions and with appropriate reagents, such primers permit the amplification of a nucleic acid molecule comprising the nucleotide sequence flanked by the primers.

For in situ methods, RNA does not need to be isolated from the cells prior to detection. In such methods, a cell or tissue sample is prepared/processed using known histological methods. The sample is then immobilized on a support, typically a glass slide, and then contacted with a probe that can hybridize to RNA that encodes the marker.

In another embodiment of the present invention, a polypeptide corresponding to a marker is detected. In some embodiments, an agent for detecting a polypeptide of the invention is an antibody capable of binding to a polypeptide corresponding to a marker of the invention. In related embodiments, the antibody has a detectable label. Antibodies can be polyclonal, or monoclonal. An intact antibody, or a fragment thereof (e.g., Fab or F(ab')$_2$) can be used.

A variety of formats can be employed to determine whether a sample contains a protein that binds to a given antibody. Examples of such formats include, but are not limited to, immunohistochemistry (IHC), enzyme immunoassay (EIA), radioimmunoassay (RIA), Western blot analysis and enzyme linked immunoabsorbant assay (ELISA). A skilled artisan can readily adapt known protein/antibody detection methods for use in determining whether tumor cells express a marker of the present invention. A skilled artisan also can readily adapt such methods for quantifying the amount of the protein in tumor cells or determining whether tumor cells express more, a normal amount, or less of a protein than non-tumor cells in the sample. In some embodiments, GLUT4 expression is measured in an immunohistochemistry assay.

Another method for determining the level of a polypeptide corresponding to a marker is mass spectrometry. For example, intact proteins or peptides, e.g., tryptic peptides can be analyzed from a sample, e.g., a blood sample, a lymph sample or other sample, containing one or more polypeptide markers. The method can further include treating the sample to lower the amounts of abundant proteins, e.g., serum albumin, to increase the sensitivity of the method. For example, liquid chromatography can be used to fractionate the sample so portions of the sample can be analyzed separately by mass spectrometry. The steps can be performed in separate systems or in a combined liquid chromatography/mass spectrometry system (LC/MS, see for example, Liao, et al. (2004) *Arthritis Rheum.* 50:3792-3803). The mass spectrometry system also can be in tandem (MS/MS) mode. The charge state distribution of the protein or peptide mixture can be acquired over one or multiple scans and analyzed by statistical methods, e.g. using the retention time and mass-to-charge ratio (m/z) in the LC/MS system, to identify proteins expressed at statistically significant levels differentially in samples from patients responsive or non-responsive to proteasome inhibition therapy. Examples of mass spectrometers which can be used are an ion trap system (ThermoFinnigan, San Jose, Calif.) or a quadrupole time-of-flight mass spectrometer (Applied Biosystems, Foster City, Calif.). The method can further include the step of peptide mass fingerprinting, e.g. in a matrix-assisted laser desorption ionization with time-of-flight (MALDI-TOF) mass spectrometry method. The method can further include the step of sequencing one or more of the tryptic peptides. Results of this method can be used to identify proteins from primary sequence databases, e.g., maintained by the National Center for Biotechnology Information, Bethesda, Md., or the Swiss Institute for Bioinformatics, Geneva, Switzerland, and based on mass spectrometry tryptic peptide m/z base peaks.

Electronic Apparatus Readable Arrays

Electronic apparatus, including readable arrays comprising at least one predictive marker of the present invention is also contemplated for use in conjunction with the methods of the invention. As used herein, "electronic apparatus readable media" refers to any suitable medium for storing, holding or containing data or information that can be read and accessed directly by an electronic apparatus. As used herein, the term "electronic apparatus" is intended to include any suitable computing or processing apparatus or other device configured or adapted for storing data or information. Examples of electronic apparatus suitable for use with the present invention and monitoring of the recorded information include stand-alone computing apparatus; networks, including a local area network (LAN), a wide area network (WAN) Internet, Intranet, and Extranet; electronic appliances such as personal digital assistants (PDAs), cellular phone, pager and the like; and local and distributed processing systems. As used herein, "recorded" refers to a process for storing or encoding information on the electronic apparatus readable medium. Those skilled in the art can readily adopt any of the presently known methods for recording information on known media to generate manufactures comprising the markers of the present invention.

For example, microarray systems are well known and used in the art for assessment of samples, whether by assessment gene expression (e.g., DNA detection, RNA detection, protein detection), or metabolite production, for example. Microarrays for use according to the invention include one or more probes of predictive marker(s) of the invention characteristic of response and/or non-response to a therapeutic regimen as described herein. In one embodiment, the microarray comprises one or more probes corresponding to one or more of markers selected from the group consisting of markers whose mutation status indicates response, markers whose mutation status indicates long time-to-progression, and markers whose mutation status indicates long term survivors among patients. A number of different microarray configurations and methods for their production are known to those of skill in the art and are disclosed, for example, in U.S. Pat. Nos. 5,242,974; 5,384,261; 5,405,783; 5,412,087; 5,424,186; 5,429,807; 5,436,327; 5,445,934; 5,556,752; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,624,711; 5,700,637; 5,744,305; 5,770,456; 5,770,722; 5,837,832; 5,856,101; 5,874,219; 5,885,837; 5,919,523; 5981185; 6,022,963; 6,077,674; 6,156,501; 6261776; 6346413; 6440677; 6451536; 6576424; 6610482; 5,143,854; 5,288,644; 5,324,633; 5,432,049; 5,470,710; 5,492,806; 5,503,980; 5,510,270; 5,525,464; 5,547,839; 5,580,732; 5,661,028; 5,848,659; and 5,874,219; Shena, et al. (1998), *Tibtech* 16:301; Duggan et al. (1999) *Nat. Genet.* 21:10; Bowtell et al. (1999) *Nat. Genet.* 21:25; Lipshutz et al. (1999) *Nature Genet.* 21:20-24, 1999; Blanchard, et al. (1996) *Biosensors and Bioelectronics,* 11:687-90; Maskos, et al., (1993) *Nucleic Acids Res.* 21:4663-69; Hughes, et al. (2001) *Nat. Biotechol.* 19:342, 2001; each of which are herein incorporated by reference. A tissue microarray can be used for protein identification (see Hans et al. (2004) *Blood* 103:275-282). A phage-epitope microarray can be used to identify one or more proteins in a sample based on whether the protein or proteins induce auto-antibodies in the patient (Bradford et al. (2006) *Urol. Oncol.* 24:237-242).

A microarray thus comprises one or more probes corresponding to one or more markers identified herein, e.g., those indicative of treatment outcome, e.g., to identify wild type marker genes, normal allelic variants and mutations of marker genes. The microarray can comprise probes corresponding to, for example, at least 2, at least 3, at least 4, at least 5, at least 10, at least 15, at least 20, at least 25, at least 30, at least 35, at least 40, at least 45, at least 50, at least 75, or at least 100, biomarkers and/or mutations thereof indicative of treatment outcome. The microarray can comprise probes corresponding to one or more biomarkers as set forth herein. Still further, the microarray may comprise complete marker sets as set forth herein and which may be selected and compiled according to the methods set forth herein. The microarray can be used to assay expression of one or more predictive markers or predictive marker sets in the array. In one example, the array can be used to assay more than one predictive marker or marker set expression in a sample to ascertain an expression profile of markers in the array. In this manner, up to about 44,000 markers can be simultaneously assayed for expression. This allows an expression profile to be developed showing a battery of markers specifically expressed in one or more samples. Still further, this allows an expression profile to be developed to assess treatment outcome.

The array is also useful for ascertaining differential expression patterns of one or more markers in normal and abnormal (e.g., sample, e.g., tumor) cells. This provides a battery of markers that could serve as a tool for ease of identification of treatment outcome of patients. Further, the array is useful for ascertaining expression of reference markers for reference expression levels. In another example, the array can be used to monitor the time course of expression of one or more markers in the array.

In addition to such qualitative determination, the invention allows the quantification of marker expression. Thus, predictive markers can be grouped on the basis of marker sets or outcome indications by the amount of the marker in the sample. This is useful, for example, in ascertaining the outcome of the sample by virtue of scoring the amounts according to the methods provided herein.

The array is also useful for ascertaining the effect of the expression of a marker on the expression of other predictive markers in the same cell or in different cells. This provides, for example, a selection of alternate molecular targets for therapeutic intervention if patient is predicted to have an unfavorable outcome.

Reagents and Kits

The invention also encompasses kits for detecting the presence of a polypeptide or nucleic acid corresponding to a marker of the invention in a sample (e.g. a bone marrow sample, tumor biopsy or a reference sample). Such kits can be used to assess treatment outcome, e.g., determine if a subject can have a favorable outcome, e.g., after proteasome inhibitor treatment. For example, the kit can comprise a labeled compound or agent capable of detecting a genomic DNA segment, a polypeptide or a transcribed RNA corresponding to a marker of the invention or a mutation of a marker gene in a biological sample and means for determining the amount of the genomic DNA segment, the polypeptide or RNA in the sample. Suitable reagents for binding with a marker protein include antibodies, antibody derivatives, antibody fragments, and the like. Suitable reagents for binding with a marker nucleic acid (e.g., a genomic DNA, an mRNA, a spliced mRNA, a cDNA, or the like) include complementary nucleic acids. The kit can also contain a control or reference sample or a series of control or reference samples which can be assayed and compared to the test sample. For example, the kit may have a positive control sample, e.g., including one or more markers or mutations described herein, or reference markers, e.g. housekeeping markers to standardize the assay among samples or timepoints or reference genomes, e.g., form subjects without tumor e.g., to establish diploid copy number baseline or reference expression level of a marker. By way of example, the kit may comprise fluids (e.g., buffer) suitable for annealing complementary nucleic acids or for binding an antibody with a protein with which it specifically binds and one or more sample compartments. The kit of the invention may optionally comprise additional components useful for performing the methods of the invention, e.g., a sample collection vessel, e.g., a tube, and optionally, means for optimizing the amount of marker detected, for example if there may be time or adverse storage and handling conditions between the time of sampling and the time of analysis. For example, the kit can contain means for increasing the number of tumor cells in the sample, as described above, a buffering agent, a preservative, a stabilizing agent or additional reagents for preparation of cellular material or probes for use in the methods provided; and detectable label, alone or conjugated to or incorporated within the provided probe(s). In one exemplary embodiment, a kit comprising a sample collection vessel can comprise e.g., a tube comprising anti-coagulant and/or stabilizer, e.g., an RNA stabilizer, as described above, or known to those skilled in the art. The kit can further comprise components necessary for detecting the detectable label (e.g., an enzyme or a substrate). For marker sets, the kit can comprise a marker set array or chip for use in detecting the biomarkers. Kits also can include instructions for interpreting the results obtained using the kit. The kit can contain reagents for detecting one or more biomarkers, e.g., 2, 3, 4, 5, or more biomarkers described herein.

In one embodiment, the kit comprises a probe to detect at least one biomarker, e.g., a marker indicative of treatment outcome (e.g., upon proteasome inhibitor treatment). In an exemplary embodiment, the kit comprises a nucleic acid probe to detect a marker gene selected from the group consisting of SEQ ID NO: 1, 2, 4, 5, 7, 8 or a sequence on chromosome 1p from base pair 115247085 to 115259515, chromosome 12p from base pair 25358180 to 25403854, or a complement of any of the foregoing or SEQ ID NO: 3, 6 and/or 9. In some embodiments, the kit comprises a probe to detect a marker selected from the group consisting of NRAS and KRAS. In some embodiments, a kit comprises probes to detect a marker set comprising two or more markers from the group consisting of NRAS and KRAS. In another embodiment, a kit comprises a probe to detect KRAS in non-hematological, e.g., solid tumor cancer samples. In related embodiments, the kit comprises a nucleic acid probe comprising or derived from (e.g., a fragment, mutant or variant (e.g., homologous or complementary) thereof) a nucleic acid sequence selected from the group consisting of SEQ ID NOs: 1, 2, 4 and 5. A kit can comprise reagents for identifying the presence of a mutation in codon 12, codon 13 and/or codon 61 of SEQ ID NO:2 or the analogous sequence in SEQ ID NO:1. In some embodiments, a kit comprises probes to detect a phenotypic marker gene, such as a glucose transporter, e.g., GLUT4. In some embodiments a kit comprises reagents, e.g., probes, e.g., a nucleic acid probe or a protein probe, to detect at least two markers, such as at least one marker corresponding to a genotypic marker gene, such as a RAS marker gene, e.g., KRAS and at least one marker corresponding to a phenotypic marker gene, such as a glucose transporter, e.g., GLUT4. In one embodiment, a kit comprising at least two reagents for assessing whether a tumor sample from a patient is associated with a favorable outcome upon treatment with a proteasome inhibitor comprises at least one reagent to detect wild type or mutant KRAS and at least one reagent which allow measurement of the amount, e.g., normal, low or high expression, of GLUT4. In the foregoing embodiments, the at least two reagents are nucleic acid reagents. Alternatively, at least one of the at least two reagents, e.g., a reagent to detect KRAS mutation, is a nucleic acid reagent and at least one of the at least two reagents, e.g., a reagent to measure expression of GLUT4, is a protein reagent, e.g., an antibody which binds to GLUT4, e.g., SEQ ID NO:9. For kits comprising nucleic acid probes, e.g., oligonucleotide-based kits, the kit can comprise, for example: one or more nucleic acid reagents such as an oligonucleotide (labeled or non-labeled) which hybridizes to a nucleic acid sequence corresponding to a marker of the invention, optionally fixed to a substrate; and can optionally further comprise labeled oligonucleotides not bound with a substrate, a primer, a pair of PCR primers, e.g., useful for amplifying a nucleic acid molecule corresponding to a marker of the invention, molecular beacon probes, a marker set comprising oligonucleotides which hybridize to at least two nucleic acid sequences corresponding to markers of the invention, and the like. The kit can contain an RNA-stabilizing agent.

Alternatively, a kit can comprise reagents for determining whether the glycine at residue 12, the glycine at residue 13 and/or the glutamine at residue 61 of SEQ ID NO:3 is present or is a different amino acid. For kits comprising protein probes, e.g., antibody-based kits, the kit can comprise, for example: (1) a first antibody (e.g., attached to a solid support) which binds to a polypeptide corresponding to a marker of the invention; and, optionally, (2) a second, different antibody which binds to either the polypeptide or the first antibody and is conjugated to a detectable label. The kit can contain a protein stabilizing agent. The kit can contain reagents to reduce the amount of non-specific binding of non-biomarker material from the sample to the probe. Examples of reagents include nonioinic detergents, non-specific protein containing solutions, such as those containing albumin or casein, or other substances known to those skilled in the art.

The invention also provides a kit containing an antibody of the invention conjugated to a detectable substance, and instructions for use. Still another aspect of the invention is a diagnostic composition comprising a probe of the invention and a pharmaceutically acceptable carrier. In one embodiment, the diagnostic composition contains an antibody of the invention, a detectable moiety, and a pharmaceutically acceptable carrier.

Antibodies

An isolated polypeptide corresponding to a predictive marker of the invention, or a fragment or mutant thereof, can be used as an immunogen to generate antibodies using standard techniques for polyclonal and monoclonal antibody preparation. For example, an immunogen typically is used to prepare antibodies by immunizing a suitable (i.e., immunocompetent) subject such as a rabbit, goat, mouse, or other mammal or vertebrate. In still a further aspect, the invention provides monoclonal antibodies or antigen binding fragments thereof, which antibodies or fragments specifically bind to a polypeptide comprising an amino acid sequence selected from the group consisting of the amino acid sequences of the present invention, an amino acid sequence encoded by the cDNA of the present invention, a fragment of at least 8, 10, 12, 15, 20 or 25 amino acid residues of an amino acid sequence of the present invention, an amino acid sequence which is at least 95%, 96%, 97%, 98% or 99% identical to an amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6×SSC at 45° C. and washing in 0.2×SSC, 0.1% SDS at 65° C. A KRAS fragment for use as an immunogen can comprise amino acid 12, amino acid 13 or amino acid 61 of SEQ ID NO:3. The monoclonal antibodies can be human, humanized, chimeric and/or non-human antibodies. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

Methods for making human antibodies are known in the art. One method for making human antibodies employs the use of transgenic animals, such as a transgenic mouse. These transgenic animals contain a substantial portion of the human antibody producing genome inserted into their own genome and the animal's own endogenous antibody production is rendered deficient in the production of antibodies. Methods for making such transgenic animals are known in the art. Such transgenic animals can be made using XENO-MOUSE™ technology or by using a "minilocus" approach. Methods for making XENOMICE™ are described in U.S. Pat. Nos. 6,162,963, 6,150,584, 6,114,598 and 6,075,181, which are incorporated herein by reference. Methods for making transgenic animals using the "minilocus" approach are described in U.S. Pat. Nos. 5,545,807, 5,545,806 and 5,625,825; also see International Publication No. WO93/12227, which are each incorporated herein by reference.

Antibodies include immunoglobulin molecules and immunologically active portions of immunoglobulin molecules, i.e., molecules that contain an antigen binding site which specifically binds an antigen, such as a polypeptide of the invention, e.g., an epitope of a polypeptide of the invention. A molecule which specifically binds to a given polypeptide of the invention is a molecule which binds the polypeptide, but does not substantially bind other molecules in a sample, e.g., a biological sample, which naturally contains the polypeptide. For example, antigen-binding fragments, as well as full-length monomeric, dimeric or trimeric polypeptides derived from the above-described antibodies are themselves useful. Useful antibody homologs of this type include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., Nature 341:544-546 (1989)), which consists of a VH domain; (vii) a single domain functional heavy chain antibody, which consists of a VHH domain (known as a nanobody) see e.g., Cortez-Retamozo, et al., Cancer Res. 64: 2853-2857 (2004), and references cited therein; and (vii) an isolated complementarity determining region (CDR), e.g., one or more isolated CDRs together with sufficient framework to provide an antigen binding fragment. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. Science 242:423-426 (1988); and Huston et al. Proc. Natl. Acad. Sci. USA 85:5879-5883 (1988). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Antibody fragments, such as Fv, F(ab')$_2$ and Fab may be prepared by cleavage of the intact protein, e.g. by protease or chemical cleavage. The invention provides polyclonal and monoclonal antibodies. Synthetic and genetically engineered variants (See U.S. Pat. No. 6,331,415) of any of the foregoing are also contemplated by the present invention. Polyclonal and monoclonal antibodies can be produced by a variety of techniques, including conventional murine monoclonal antibody methodology e.g., the standard somatic cell hybridization technique of Kohler and Milstein, Nature 256: 495 (1975) the human B cell hybridoma technique (see Kozbor et al., 1983, Immunol. Today 4:72), the EBV-hybridoma technique (see Cole et al., pp. 77-96 In Monoclonal Antibodies and Cancer Therapy, Alan R. Liss, Inc., 1985) or trioma techniques. See generally, Harlow, E. and Lane, D. (1988) Antibodies: A Laboratory Manual, Cold Spring Harbor Laboratory Press, Cold Spring Harbor, N.Y.; and Current Protocols in Immunology, Coligan et al. ed., John Wiley & Sons, New York, 1994. For diagnostic applications, the antibodies can be monoclonal antibodies, e.g., generated in mouse, rat, or rabbit. Additionally, for use in in viva applications the antibodies of the present invention can be human or humanized antibodies. Hybridoma cells producing a monoclonal antibody of the invention are detected by screening the hybridoma culture supernatants for antibodies that bind the polypeptide of interest, e.g., using a standard ELISA assay.

If desired, the antibody molecules can be harvested or isolated from the subject (e.g., from the blood or serum of the subject) and further purified by well-known techniques, such as protein A chromatography to obtain the IgG fraction. Alternatively, antibodies specific for a protein or polypeptide of the invention can be selected or (e.g., partially purified) or purified by, e.g., affinity chromatography to obtain substantially purified and purified antibody. By a substantially purified antibody composition is meant, in this context, that the antibody sample contains at most only 30% (by dry weight) of contaminating antibodies directed against epitopes other than those of the desired protein or polypeptide of the invention, and at most 20%, at most 10%, or at most 5% (by dry weight) of the sample is contaminating antibodies. A purified antibody composition means that at least 99% of the antibodies in the composition are directed against the desired protein or polypeptide of the invention.

An antibody directed against a polypeptide corresponding to a marker of the invention (e.g., a monoclonal antibody) can be used to detect the marker (e.g., in a cellular sample) in order to evaluate the level and pattern of expression of the marker. The antibodies can also be used diagnostically to monitor protein levels in tissues or body fluids (e.g. in a blood sample) as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Accordingly, in one aspect, the invention provides substantially purified antibodies or fragments thereof, and non-human antibodies or fragments thereof, which antibodies or fragments specifically bind to a polypeptide comprising an amino acid sequence encoded by a marker identified herein. The substantially purified antibodies of the invention, or fragments thereof, can be human, non-human, chimeric and/or humanized antibodies.

In another aspect, the invention provides non-human antibodies or fragments thereof, which antibodies or fragments specifically bind to a polypeptide comprising an amino acid sequence which is encoded by a nucleic acid molecule of a predictive marker of the invention. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies.

The substantially purified antibodies or fragments thereof may specifically bind to a signal peptide, a secreted sequence, an extracellular domain, a transmembrane or a cytoplasmic domain or cytoplasmic loop of a polypeptide of the invention. The substantially purified antibodies or fragments thereof, the non-human antibodies or fragments thereof, and/or the monoclonal antibodies or fragments thereof, of the invention specifically bind to a secreted sequence or an extracellular domain of the amino acid sequences of the present invention.

Sensitivity Assays

A sample of cancerous cells is obtained from a patient. An expression level is measured in the sample for a marker corresponding to at least one of the markers described herein. A marker set can be utilized comprising markers identified described herein, and put together in a marker set using the methods described herein. Such analysis is used to obtain an expression profile of the tumor in the patient. Evaluation of the expression profile is then used to determine whether the patient is expected to have a favorable outcome and would benefit from treatment, e.g., proteasome inhibition therapy (e.g., treatment with a proteasome inhibitor (e.g., bortezomib or ixazomib citrate) alone, or in combination with additional agents)), or an alternative agent expected to have a similar effect on survival. Evaluation of the expression profile can also be used to determine whether a patient is expected to have an unfavorable outcome and would benefit from a cancer therapy other than proteasome inhibition therapy or would benefit from an altered proteasome inhibition therapy regimen. Evaluation can include use of one marker set prepared using any of the methods provided or other similar scoring methods known in the art (e.g., weighted voting, combination of threshold features (CTF), Cox proportional hazards analysis, principal components scoring, linear predictive score, K-nearest neighbor, etc), e.g., using expression values deposited with the Gene Expression Omnibus (GEO) program at the National Center for Biotechnology Information (NCBI, Bethesda, Md.). Still further, evaluation can comprise use of more than one prepared marker set. A proteasome inhibition therapy will be identified as appropriate to treat the cancer when the outcome of the evaluation demonstrates a favorable outcome or a more aggressive therapy regimen will be identified for a patient with an expected unfavorable outcome.

In one aspect, the invention features a method of evaluating a patient, e.g., a patient with cancer, e.g., a solid tumor e.g. a non-hematological cancer (e.g non-small cell lung cancer, colon cancer, pancreatic cancer, breast cancer, ovarian cancer, melanoma, head and neck carcinoma, prostate cancer or renal cell carcinoma) for treatment outcome. The method includes providing an evaluation of the expression of the markers in a marker set of markers in the patient, wherein the marker set has the following properties: it includes a plurality of genes, each of which is differentially expressed as between patients with identified outcome and non-afflicted subjects and it contains a sufficient number of differentially expressed markers such that differential amount (e.g., as compared to a level in a non-afflicted reference sample) of each of the markers in the marker set in a subject is predictive of treatment outcome with no more than about 15%, about 10%, about 5%, about 2.5%, or about 1% false positives (wherein false positive means predicting that a patient as responsive or non-responsive when the subject is not); and providing a comparison of the amount of each of the markers in the set from the patient with a reference value, thereby evaluating the patient.

Examining the amount of one or more of the identified markers or marker sets in a tumor sample taken from a patient during the course of proteasome inhibition therapy, it is also possible to determine whether the therapeutic agent is continuing to work or whether the cancer has become non-responsive (refractory) to the treatment protocol. For example, a patient receiving a treatment of bortezomib or ixazomib citrate would have tumor cells removed and monitored for the expression of a marker or marker set. If the profile of the amount of one or more markers identified herein more typifies favorable outcome in the presence of the agent, e.g., the proteasome inhibitor, the treatment would continue. However, if the profile of the amount of one or more markers identified herein more typifies unfavorable outcome in the presence of the agent, then the cancer may have become resistant to therapy, e.g., proteasome inhibition therapy, and another treatment protocol should be initiated to treat the patient. For example, the cancer may comprise a mutation in a marker gene associated with resistance to proteasome inhibition.

Importantly, these determinations can be made on a patient-by-patient basis or on an agent-by-agent (or combinations of agents). Thus, one can determine whether or not a particular proteasome inhibition therapy is likely to benefit a particular patient or group/class of patients, or whether a particular treatment should be continued.

Use of Information

In one method, information, e.g., about the mutational status of a patient's tumor, e.g., the patient's marker(s) characteristic, e.g., size, sequence, composition, activity or amount (e.g., the result of evaluating a marker or marker set described herein), or about whether a patient is expected to have a favorable outcome, is provided (e.g., communicated, e.g., electronically communicated) to a third party, e.g., a hospital, clinic, a government entity, reimbursing party or insurance company (e.g., a life insurance company). For example, choice of medical procedure, payment for a medical procedure, payment by a reimbursing party, or cost for a service or insurance can be function of the information. E.g., the third party receives the information, makes a determination based at least in part on the information, and optionally communicates the information or makes a choice of procedure, payment, level of payment, coverage, etc. based on the information. In the method, informative characteristic of a marker or a marker set selected from or derived from Table 1 and/or described herein is determined.

In one embodiment, a premium for insurance (e.g., life or medical) is evaluated as a function of information about one or more marker mutational status or expression levels, e.g., a marker or marker set, e.g., a level of expression associated with treatment outcome (e.g., the informative amount). For example, premiums can be increased (e.g., by a certain percentage) if the marker genes of a patient or a patient's marker set described herein have different characteristic, e.g., size, sequence, composition, activity or amount between an insured candidate (or a candidate seeking insurance coverage) and a reference value (e.g., a non-afflicted person) or a reference sample, e.g., matched control. Premiums can also be scaled depending on the result of evaluating a marker or marker set described herein. For example, premiums can be assessed to distribute risk, e.g., as a function of marker, e.g., the result of evaluating a marker or marker set described herein. In another example, premiums are assessed as a function of actuarial data that is obtained from patients that have known treatment outcomes.

Information about marker characteristic, e.g., size, sequence, composition, activity or amount, e.g., the result of evaluating a marker or marker set described herein (e.g., the informative characteristic), can be used, e.g., in an underwriting process for life insurance. The information can be incorporated into a profile about a subject. Other information in the profile can include, for example, date of birth, gender, marital status, banking information, credit information, children, and so forth. An insurance policy can be recommended as a function of the information on marker characteristic, e.g., size, sequence, composition, activity or amount, e.g., the result of evaluating a marker or marker set described herein, along with one or more other items of information in the profile. An insurance premium or risk assessment can also be evaluated as function of the marker or marker set information. In one implementation, points are assigned on the basis of expected treatment outcome.

In one embodiment, information about marker characteristic, e.g., size, sequence, composition, activity or amount, e.g., the result of evaluating a marker or marker set described herein, is analyzed by a function that determines whether to authorize the transfer of funds to pay for a service or treatment provided to a subject (or make another decision referred to herein). For example, the results of analyzing a characteristic, e.g., size, sequence, composition, activity or amount of a marker or marker set described herein may indicate that a subject is expected to have a favorable outcome, suggesting that a treatment course is needed, thereby triggering an result that indicates or causes authorization to pay for a service or treatment provided to a subject. In one example, informative characteristic, e.g., size, sequence, composition, activity or amount of a marker or a marker set selected from or derived from Table 1 and/or described herein is determined and payment is authorized if the informative amount identifies a favorable outcome. For example, an entity, e.g., a hospital, care giver, government entity, or an insurance company or other entity which pays for, or reimburses medical expenses, can use the result of a method described herein to determine whether a party, e.g., a party other than the subject patient, will pay for services (e.g., a particular therapy) or treatment provided to the patient. For example, a first entity, e.g., an insurance company, can use the outcome of a method described herein to determine whether to provide financial payment to, or on behalf of, a patient, e.g., whether to reimburse a third party, e.g., a vendor of goods or services, a hospital, physician, or other care-giver, for a service or treatment provided to a patient. For example, a first entity, e.g., an insurance company, can use the outcome of a method described herein to determine whether to continue, discontinue, enroll an individual in an insurance plan or program, e.g., a health insurance or life insurance plan or program.

In one aspect, the disclosure features a method of providing data. The method includes providing data described herein, e.g., generated by a method described herein, to provide a record, e.g., a record described herein, for determining if a payment will be provided. In some embodiments, the data is provided by computer, compact disc, telephone, facsimile, email, or letter. In some embodiments, the data is provided by a first party to a second party. In some embodiments, the first party is selected from the subject, a healthcare provider, a treating physician, a health maintenance organization (HMO), a hospital, a governmental entity, or an entity which sells or supplies the drug. In some embodiments, the second party is a third party payor, an insurance company, employer, employer sponsored health plan, HMO, or governmental entity. In some embodiments, the first party is selected from the subject, a healthcare provider, a treating physician, an HMO, a hospital, an insurance company, or an entity which sells or supplies the drug and the second party is a governmental entity. In some embodiments, the first party is selected from the subject, a healthcare provider, a treating physician, an HMO, a hospital, an insurance company, or an entity which sells or supplies the drug and the second party is an insurance company.

In another aspect, the disclosure features a record (e.g., computer readable record) which includes a list and value of characteristic, e.g., size, sequence, composition, activity or amount for the marker or marker set for a patient. In some embodiments, the record includes more than one value for each marker.

Screening Assays

The invention provides methods (also referred to herein as "screening assays") for identifying proteasome inhibitors, i.e., candidate or test compounds or agents (e.g., proteins, peptides, peptidomimetics, peptoids, small molecules or other drugs) which have a inhibitory effect on, for example, KRAS mutant expression or RAS pathway activity, or have a stimulatory or inhibitory effect on, for example, the expression or activity of a KRAS substrate or proteins in the RAS pathway, or on the expression or activity of a glucose transporter, e.g., GLUT4. Compounds thus identified can be used to modulate the activity of target gene products (e.g., KRAS mutant genes) in a therapeutic protocol, to elaborate the biological function of the target gene product, or to identify compounds that disrupt KRAS mutant interactions. Compounds, e.g., proteasome inhibitors, can be identified that cause the death, apoptosis or senescence of cells, e.g., cells from a solid tumor, e.g., non-hematological tumor, e.g., non-small cell lung cancer, colon cancer, pancreatic cancer, breast cancer, ovarian cancer, melanoma, head and neck carcinoma, prostate cancer or renal cell carcinoma, or a cell line, e.g., cells grown from an explant of a tumor from a nonresponsive patient, which have a mutant KRAS gene, or an active RAS pathway and/or increased glucose transport.

In other embodiments, the assay can identify compounds which modulate one or more activity of a KRAS mutant, e.g., the ability to bind a nucleotide, e.g., GTP or GDP; the ability to hydrolyze a nucleotide; the ability to bind RAS-GAP, the ability to bind a phospholipid bilayer, e.g, a cell membrane; the ability to control the cell cycle, the ability of the cell to regulate protein homeostasis; and/or the ability to support tumor cell survival. In some embodiments, there can be a comparison of the activity of the KRAS mutant in the presence of the test agent with the activity in the presence of a proteasome inhibitor, e.g., a peptidyl boronic acid, e.g., bortezomib or ixazomib citrate, to which the KRAS mutant or the cell comprising the KRAS mutant has resistance.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145). Additional compounds can be synthesized from the guidance provided in the publications disclosing proteasome inhibitors described in an earlier section.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner USP '409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

In one embodiment, an assay is a cell-based assay in which a cell which expresses a KRAS mutant protein or biologically active portion thereof is contacted with a test compound, and the ability of the test compound to modulate KRAS mutant activity or the viability of the cell is determined. In one embodiment, an in vitro cell-based assay is conducted on cells grown under nutrient-poor, e.g., low serum or low glucose, conditions. Determining the ability of the test compound to modulate KRAS mutant activity can be accomplished by monitoring, for example, the ability to bind a nucleotide, e.g., GTP or GDP; the ability to hydrolyze a nucleotide; the ability to bind RASGAP, the ability to bind a phospholipid bilayer, e.g, a cell membrane, the ability to control the cell cycle, the ability of the cell to regulate protein homeostasis, and/or the ability to support tumor cell survival. The effect of the test compound can be compared to a control cell not exposed to the test compound. In some embodiments, there can be a comparison of the activity of the KRAS mutant in the presence of the test agent with the activity in the presence of a proteasome inhibitor, e.g., a peptidyl boronic acid, e.g., bortezomib or ixazomib citrate, to which the KRAS mutant or the cell comprising the KRAS mutant has resistance. The cell, for example, can be of mammalian origin, e.g., human. In other embodiments, the assay can determine the ability of the test compound to modulate a variant of an enzyme structurally or mechanistically similar to KRAS in a drug resistant cell line in vitro or in vivo, e.g, in a xenograft tumor model. The compound is identified as modulator of drug resistance or a proteasome inhibitor agent when the cell viability or cell growth is decreased.

The present invention will now be illustrated by the following Examples, which are not intended to be limiting in any way.

EXAMPLES

Example 1

Xenografts

Xenografts with names beginning with PHTX were derived at Millennium Pharmaceuticals, Inc. as follows: patient-derived tumors were obtained through the Cooperative Human Tissue Network and the National Disease Research Interchange. Within 24 hours of surgery, tumors were implanted into 4 SCID-NOD mice. The tumors were serially passaged 2-3 times in SCID-NOD mice to confirm growth, and material was banked in liquid nitrogen in order to re-derive tumors for future use. Tumors were further passaged into larger numbers of NCr-Nude and/or CB17 SCID mice for studies of MLN2238 as listed in Table 3. The patient-derived tumors were characterized histologically by H&E staining, and DNA from frozen sections of the passaged tumors was prepared for mutation analysis by Sequenom.

TABLE 3

Source information of primary human tumors

| Primary Tumor ID | Tissue Type | Diagnosis | Donor Sex | Donor Age | Donor Race | implantation Date |
|---|---|---|---|---|---|---|
| PHTX-09C | Colon | Adenocarcinoma | Female | 80 | White | Jun. 27, 2006 |
| PHTX-11C | Colon | Adenocarcinoma | Male | 49 | White | Jul. 13, 2006 |
| PHTX-17C | Colon | Adenocarcinoma | Male | 71 | Unknown | Jul. 27, 2006 |
| PHTX-21C | Colon | Adenocarcinoma | Female | 91 | Caucasian | Aug. 9, 2006 |
| PHTX-24C | Colon | Adenocarcinoma | Female | 89 | White | Aug. 22, 2009 |
| PHTX-132Lu | Lung | Adenocarcinoma | Female | 56 | Caucasian | May 29, 2009 |
| PHTX-192Lu | Lung | Adenocarcinoma | Female | 67 | Unknown | Dec. 4, 2009 |

Xenografts with names beginning with LXF are from Oncotest GmbH, Freiburg, Germany. Studies with these tumors were performed at Oncotest GmbH, with MLN2238 provided by Millennium Pharmaceuticals, Inc. SW48 and SW48-K-Ras G13D cell lines were obtained from Horizon Discovery Ltd., Cambridge UK, and experiments with MLN2238 were performed at Millennium Pharmaceuticals, Inc. All other xenografts in these studies were derived from cell lines purchased from ATCC.

Analysis of Genomic Alterations

Genomic DNA was isolated from xenograft tumors and cell lines using Qiagen recommended protocols. Mutation status was determined by testing a panel of cancer genes and known tumor suppressors using the Sequenom (San Diego, Calif.) mass spectrometry genotype analysis system.

The panel of mutations evaluated consisted of the ONCOCARTA™ version 1.0 (the LXF cell models) and custom assays designed in collaboration with Sequenom and Millennium to expand the list of mutations surveyed (versions 2 and 3) to 514 known mutations in 41 oncogenes and tumor suppressor genes. Table 4 lists genes with mutations included in the panel and the number in parentheses ( ) indicates the approximate number of mutations targeted in assays of the genes. The cell lines described herein were tested for KRAS mutations resulting in the following amino acid changes: G12 to A, C, D, F, R, S or V; G13 to D, V, C, S, A or R; L19 to F; Q22 to K; T58 to I; A59 to T or V; G60 to D; Q61 to E, H, K, L, P or R; and A146 to T.

TABLE 4

Genes with mutant regions included in ONCOCARTA ™ panel.

| | | | | |
|---|---|---|---|---|
| ABL1 (16) | EGFR (74) | GNAQ (1) | MLH1 (1) | RB1 (11) |
| AKT1 (9) | ERBB (2) | HRAS (6) | MYC (6) | RET (20) |
| AKT2 (2) | ERBB2 (7) | JAK2 (1) | NRAS (10) | SOS1 (3) |
| APC (12) | FBX4 (6) | JAK3 (3) | PDGFRA (27) | SRC (1) |
| BRAF (44) | FBXW7 (4) | KIT (69) | PIK3CA (39) | STK11 (11) |
| CDK (2) | FGFR1 (2) | KRAS (16) | PTEN (12) | |
| CDKN2A (7) | FGFR2 (2) | MAP2K1 (5) | PTPN11 (1) | TP53 (15) |
| CSF1R (4) | FGFR3 (6) | MAP2K2 (5) | | VHL (7) |
| CTNNB1 (27) | FLT3 (7) | MET (11) | | |

The custom assays were designed using TYPEPLEX® chemistry with single-base extension which determines the expected mass weight of the extend products to ensure separation between all potential peaks found within a multiplexed reaction. 15 nl of amplified and extended product is spotted on a 384 SpectroCHIP II using a Nanodispenser. A 3-point calibrant is added to every chip to ensure proper performance of the Sequenom Maldi-tof compact mass spectrometer. The SpectroCHIP II is placed in the Sequenom MALDI-TOF compact mass spectrometer. The mass spectrometer is set to fire a maximum of 9 acquisitions for each spot on the 384 well spectroCHIP. TypePLEX Gold kit SpectroCHIP II is used following manufacturers recommended protocols.

Analysis is performed using Sequenom analysis software, MassARRAY® Typer Analyzer v4 with a default mutation call filter of 10%. Default threshold for positive mutant call is a minimal 10% mutant allele frequency, though signal as low as 3% may be detected. In house evaluation of sensitivity suggests an 8% threshold may be employed with low false positive rates.

Xenograft Tumor Growth in Immunocompromised Mice

The investigational drug MLN9708 (Kupperman et al. (2010) Cancer Res. 70:1970-1980) is an oral proteasome inhibitor currently being evaluated in Phase III trials of multiple myeloma and light chain amyloidosis and in Phase 1 and 2 trials in hematological and solid tumor malignancies. Upon exposure to aqueous solutions or plasma, MLN9708 immediately hydrolyzes to MLN2238, the biologically active form. In many studies, MLN2238 is used as a surrogate for MLN9708. In vitro, MLN2238 is potent across a broad range of solid tumor cell types evaluated with standard cell viability and colony formation assays (Kupperman et al. supra). However, not all cell lines which respond to MLN2238 in vitro are responsive to MLN2238 when grown in vivo as xenografts in immunocompromised mice. In order to understand the contributing factors that determine in vivo sensitivity to MLN2238, a panel of 6 colon and 14 non-small cell lung (NSCLC) xenograft tumors were evaluated for mutations in cancer-related genes and for tumor pharmacokinetics and pharmacodynamic markers.

Cell-line derived xenografts: freshly dissociated tumor cells grown using standard cell culture procedures were aseptically injected into the subcutaneous space in the dorsal flank of immunocompromised mice. The number of injected cells and the strain of mice are listed in Table 5.

Primary human tumor derived xenografts: tumors are grown by serial passage in immunocompromised mice, and no cell culture procedures were used. Freshly excised tumor fragments from xenograft-bearing mice were implanted via trochar into the subcutaneous space in the dorsal flank of recipient immunocompromised mice of the strain shown in Table 5.

Tumor measurement: After inoculation, tumors were measured twice weekly using a vernier caliper. Tumor volumes were calculated using a standard formula (0.5× [length×width$^2$]). When the tumors reached a volume of approximately 150-250 mm$^3$, mice were randomized into treatment groups.

Treatment period: Drug-treated group received MLN2238 by intravenous administration twice weekly for 3 weeks, at or below the maximum tolerated dose identified in tolerability studies conducted in the same strain of tumor bearing mice (strain and dose listed in table). The control group received vehicle (5% hydroxyprolyl beta-cyclodextrin) by the same route and schedule. Tumor size and body weight were measured twice a week. T/C value (average volume of treatment group/average volume of control group) was calculated on the days listed in the Table 6.

TABLE 5

Xenograft model details

| Xenograft model | Type tumor | Ras status | Dose (mg/kg) | # of cells inoculated/ mouse | Matrigel | Inoculation route | mouse strain |
| --- | --- | --- | --- | --- | --- | --- | --- |
| NCI-H1650 | Lung | WT | 11 | 2 × 10$^6$ | yes (1:1) | Flank (SC) | Balb/c nu/nu |
| HCC827 | Lung | WT | 13 | 6 × 10$^6$ | yes (1:1) | Flank (SC) | NCr-Nude |
| NCI-H1975 | Lung | WT | 13 | 1 × 10$^6$ | yes (1:1) | Flank (SC) | NCr-Nude |
| PHTX132Lu | Lung | WT | 14 | NA | NA | Trocar | CB-17 SCID |
| LXFE409 | Lung | WT | 13 | NA | NA | Trocar | NMRI nu/nu |
| LXFA677 | Lung | WT | 13 | NA | NA | Trocar | NMRI nu/nu |
| LXFL1121 | Lung | WT | 13 | NA | NA | Trocar | NMRI nu/nu |
| A549 | Lung | Kras G12S | 11 | 5 × 10$^6$ | yes (1:1) | Flank (SC) | Balb/c nu/nu |
| Calu6 | Lung | Kras Q61K | 14 | 5 × 10$^6$ | No | Flank (SC) | NCr-Nude |
| NCI-H358 | Lung | Kras G12C | 11 | 5 × 10$^6$ | yes (1:1) | Flank (SC) | Balb/c nu/nu |
| NCI-H460 | Lung | Kras Q61H | 14 | 2.5 × 10$^6$ | No | Flank (SC) | NCr-Nude |
| LXFA1041 | Lung | Kras G12V | 13 | NA | NA | Trocar | NMRI nu/nu |
| LXFL1674 | Lung | Kras G12C | 13 | NA | NA | Trocar | NMRI nu/nu |
| PHTX-192Lu | Lung | Kras G13D | 14 | NA | NA | Trocar | CB-17 SCID |
| PHTX21C | Colon | WT | 11 | NA | NA | Trocar | CB-17 SCID |
| PHTX24C | Colon | Kras A146T* | 14 | NA | NA | Trocar | NCr-Nude |
| HCT116 | Colon | Kras G13D | 14 | 2 × 10$^6$ | No | Flank (SC) | NCr-Nude |
| PHTX11C | Colon | Kras Q61H | 13 | NA | NA | Trocar | CB-17 SCID |
| PHTX17C | Colon | Kras G12V | 14 | NA | NA | Trocar | NCr-Nude |

TABLE 5-continued

Xenograft model details

| Xenograft model | Type tumor | Ras status | Dose (mg/kg) | # of cells inoculated/ mouse | Matrigel | Inoculation route | mouse strain |
|---|---|---|---|---|---|---|---|
| PHTX9C | Colon | Kras G12D | 13 | NA | NA | Trocar | CB-17 SCID |
| SW48 | Colon | WT | 13 | 2 × 10⁶ | yes (1:1) | Flank (SC) | NCr-Nude |
| SW48-Kras G13D | Colon | Kras G13D | 13 | 2 × 10⁶ | yes (1:1) | Flank (SC) | NCr-Nude |
| SW48-Kras G12V | Colon | Kras G12V | 13 | 2 × 10⁶ | yes (1:1) | Flank (SC) | NCr-Nude |
| LXFL1072 | Lung | Kras G12C | 8 | NA | NA | Trocar | NMRI nu/nu |
| LXFA1335 | Lung | Kras G12C | 8 | NA | NA | Trocar | NMRI nu/nu |
| LXFA1647 | Lung | WT | 8 | NA | NA | Trocar | NMRI nu/nu |
| LXFE397 | Lung | WT | 8 | NA | NA | Trocar | NMRI nu/nu |
| LXFE937 | Lung | WT | 8 | NA | NA | Trocar | NMRI nu/nu |
| LXFE409 | Lung | WT | 8 | NA | NA | Trocar | NMRI nu/nu |

*a rare mutation

Table 6 summarizes the tumor growth results after treatment with MLN2238. Table 6 section A lists the results with higher dose MLN2238 (11-14 mg/kg) and section B lists the results with lower dose MLN2238 (8 mg/kg). FIG. 1 is a chart which organizes the T/C values on the day of analysis (listed in Table 6, section A) by the status of the KRAS gene (wild type or mutant). There is a significant association of KRAS status with sensitivity or response to treatment with the proteasome inhibitor. In this example, colorectal and non-small cell lung xenograft tumors with no mutations in KRAS (wild type) are more sensitive to MLN2238 than those with KRAS mutations. The average Tumor to Control ratio (T/C) of KRAS wild type xenografts was 0.4 and the average T/C of KRAS mutant xenografts was 0.82.

TABLE 6

Xenograft tumor growth results after treatment with MLN2238

| Xenograft model | Day of analysis | Av. Volume of control tumors (mm³ ± SEM) | Av. Volume of treated tumors (mm³ ± SEM) | T/C (av. Volume of treated/av. Volume control) |
|---|---|---|---|---|
| A. Higher dose MLN2238 | | | | |
| LXFE409 | 20 | 671.6 ± 86.5 | 46.4 ± 10 | 0.07 |
| HCC827 | 22 | 1706.3 ± 95 | 448.5 ± 45.8 | 0.26 |
| PHTX132Lu | 21 | 1906.7 ± 114.5 | 462.8 ± 45.2 | 0.24 |
| PHTX132Lu | 21 | 1767.4 ± 155 | 605.9 ± 66.6 | 0.34 |
| LXFA677 | 21 | 1338.4 ± 186.4 | 586.2 ± 82.1 | 0.42 |
| PHTX24C | 21 | 897.5 ± 123.8 | 382.1 ± 63.5 | 0.43 |
| PHTX24C | 22 | 589.8 ± 125.9 | 255.3 ± 36.3 | 0.43 |
| PHTX21C | 21 | 598.5 ± 56.5 | 287.7 ± 46.8 | 0.48 |
| NCI-H1650 | 21 | 1218.4 ± 91.6 | 630.1 ± 50.4 | 0.52 |
| NCI-H1650 | 21 | 1017.1 ± 66.3 | 581.2 ± 55.1 | 0.57 |
| PHTX9C | 21 | 1517.3 ± 159.3 | 950.3 ± 88.4 | 0.63 |
| PHTX9C | 18 | 1258.8 ± 241.1 | 809.9 ± 95.8 | 0.64 |
| NCI-H1975 | 19 | 2544.6 ± 244.6 | 1230.4 ± 227.7 | 0.48 |
| LXFL1121 | 22 | 1375.1 ± 154.1 | 940.8 ± 127.2 | 0.68 |
| Calu-6 | 18 | 1,156.5 ± 163.5 | 799.6 ± 182.7 | 0.69 |
| Calu6 | 20 | 1796.9 ± 238.5 | 1758.3 ± 203.4 | 0.98 |
| LXFL1674 | 20 | 2023.8 ± 183.4 | 1408.0 ± 124.2 | 0.69 |
| LXFA1041 | 21 | 810.0 ± 108.6 | 609.3 ± 150.7 | 0.75 |
| PHTX11C | 22 | 685 ± 111 | 526.7 ± 44.5 | 0.77 |
| PHTX-192Lu | 21 | 1335.4 ± 139.7 | 1062.5 ± 101.9 | 0.8 |
| A549 | 21 | 1093.4 ± 139.9 | 1021.3 ± 97.7 | 0.9 |
| NCI-H358 | 24 | 591.2 ± 71.6 | 546.6 ± 89.8 | 0.92 |
| HCT116 | 22 | 1541.4 ± 212.3 | 1455.2 ± 192.1 | 0.94 |
| NCI-H460 | 16 | 1162.2 ± 196.5 | 1301.3 ± 120.6 | 1.1 |
| PHTX17C | 21 | 747.6 ± 66.1 | 848.5 ± 132.1 | 1.1 |
| SW48 | 21 | 2131 ± 151.4 | 856 ± 69.8 | 0.4 |
| SW48 | 20 | 2429.1 ± 263.1 | 1083.4 ± 51.7 | 0.45 |
| SW48-Kras G13D | 19 | 2141.3 ± 126.2 | 2205.1 ± 121.5 | 1.03 |
| SW48-Kras G13D | 20 | 2074.7 ± 243.3 | 2232.3 ± 274 | 1.08 |
| SW48-Kras G12V | 22 | 1547.3 ± 144 | 1525.9 ± 130.8 | 0.99 |

TABLE 6-continued

Xenograft tumor growth results after treatment with MLN2238

| Xenograft model | Day of analysis | Av. Volume of control tumors (mm³ ± SEM) | Av. Volume of treated tumors (mm³ ± SEM) | T/C (av. Volume of treated/av. Volume control) |
|---|---|---|---|---|
| B. Lower Dose MLN2238 | | | | |
| LXFE409 | 21 | 644.86 ± 90 | 186.21 ± 22.7 | 0.28 |
| LXFE397 | 21 | 1758.55 ± 170.6 | 1017.41 ± 211.7 | 0.57 |
| LXFE937 | 26 | 623.48 ± 93.7 | 370.96 ± 38.4 | 0.59 |
| LXFA1647 | 25 | 481.31 ± 53.9 | 384.3 ± 74.4 | 0.79 |
| LXFA1335 | 21 | 499.07 ± 60.3 | 419.42 ± 45.7 | 0.84 |
| LXFL1072 | 20 | 614.49 ± 67.1 | 675.83 ± 84.5 | 1.09 |

Figure 2A:
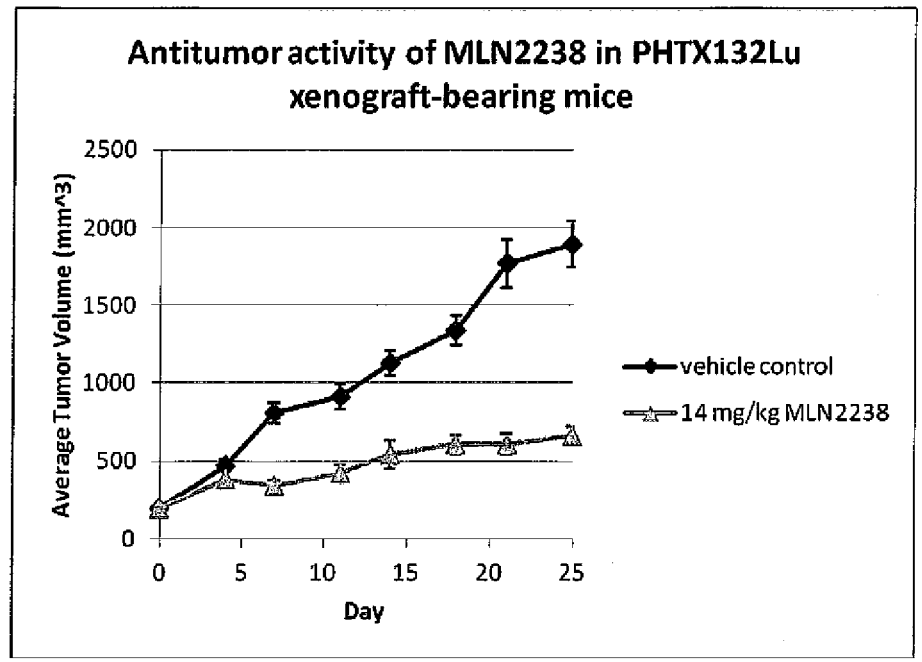
Figure 2B:
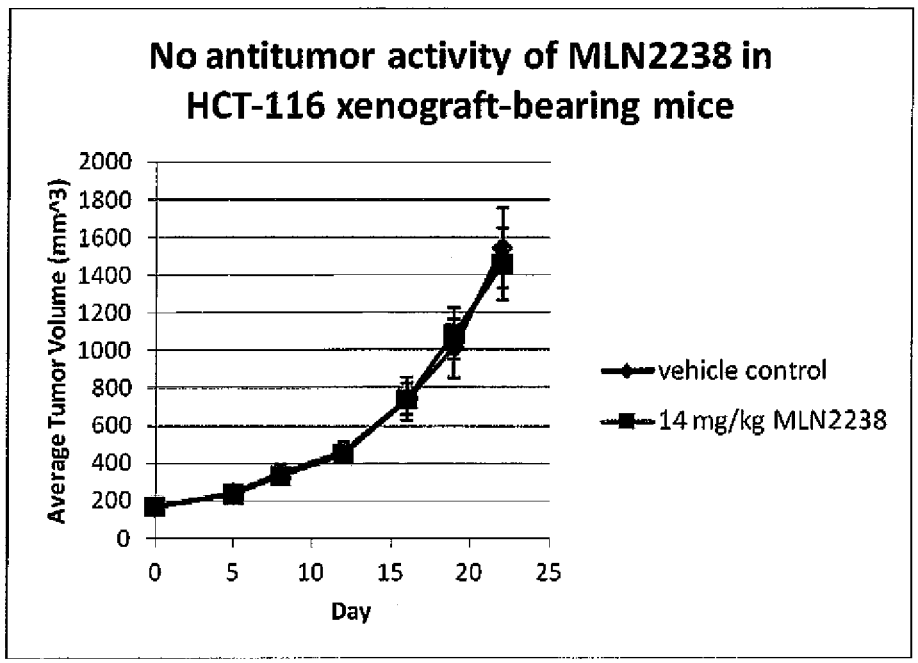

FIGS. 2A and 2B illustrate the antitumor activity of MLN2238 in representative tumor xenografts. FIG. 2A illustrates the response to MLN2238 in a xenograft with wild type KRAS. FIG. 2B illustrates the response to MLN2238 in a xenograft with mutant KRAS. It was determined that resistance of KRAS mutant tumors to MLN2238 was not due to a lack of drug exposure (as measured in a liquid chromatography-tandem mass spectrometry (LC/MS/MS)-based method) or lack of tumor proteasome inhibition (as measured by inhibition of the β5 subunit of the 20S proteasome) in tumor samples.

Figure 3A:
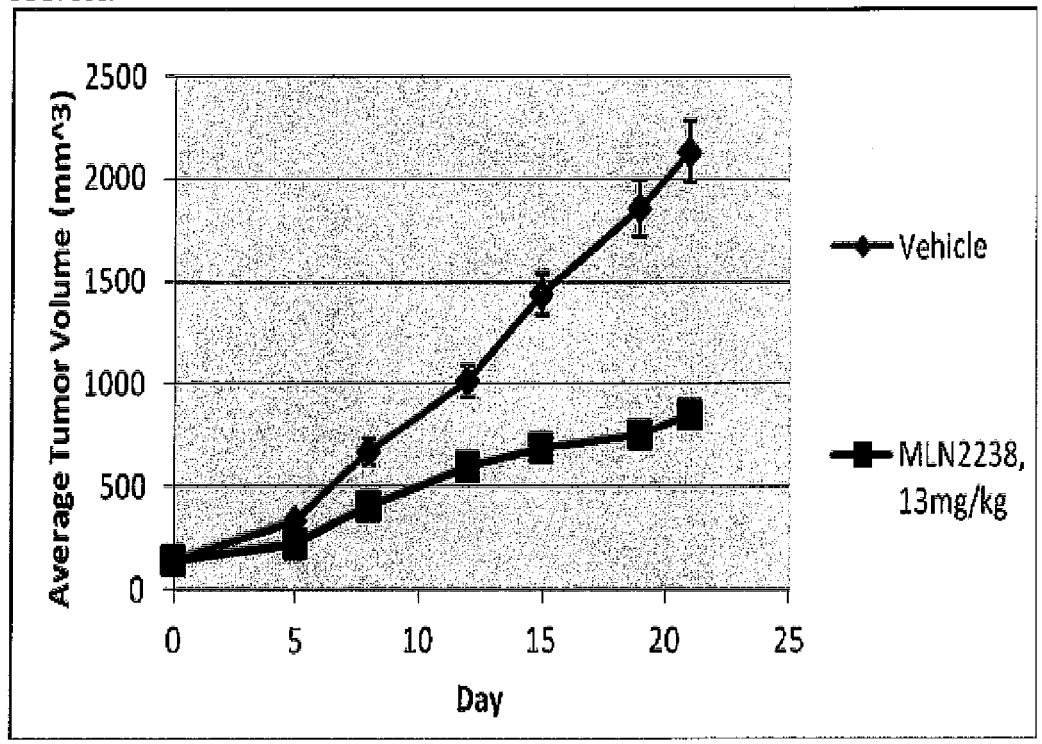
Figure 3B:
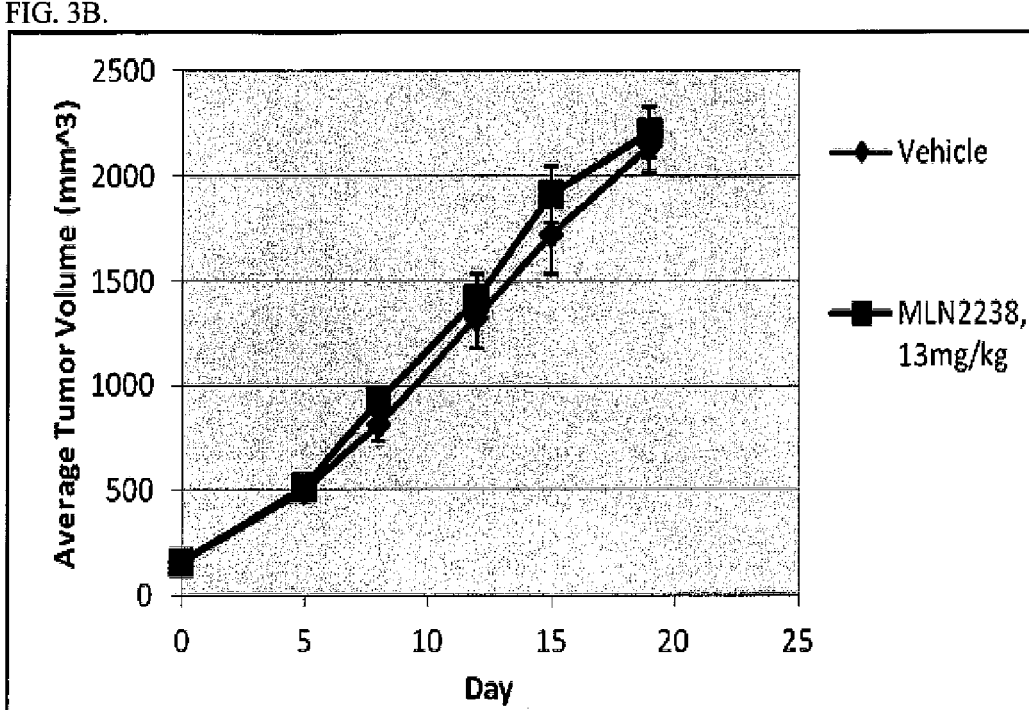
Figure 3C:
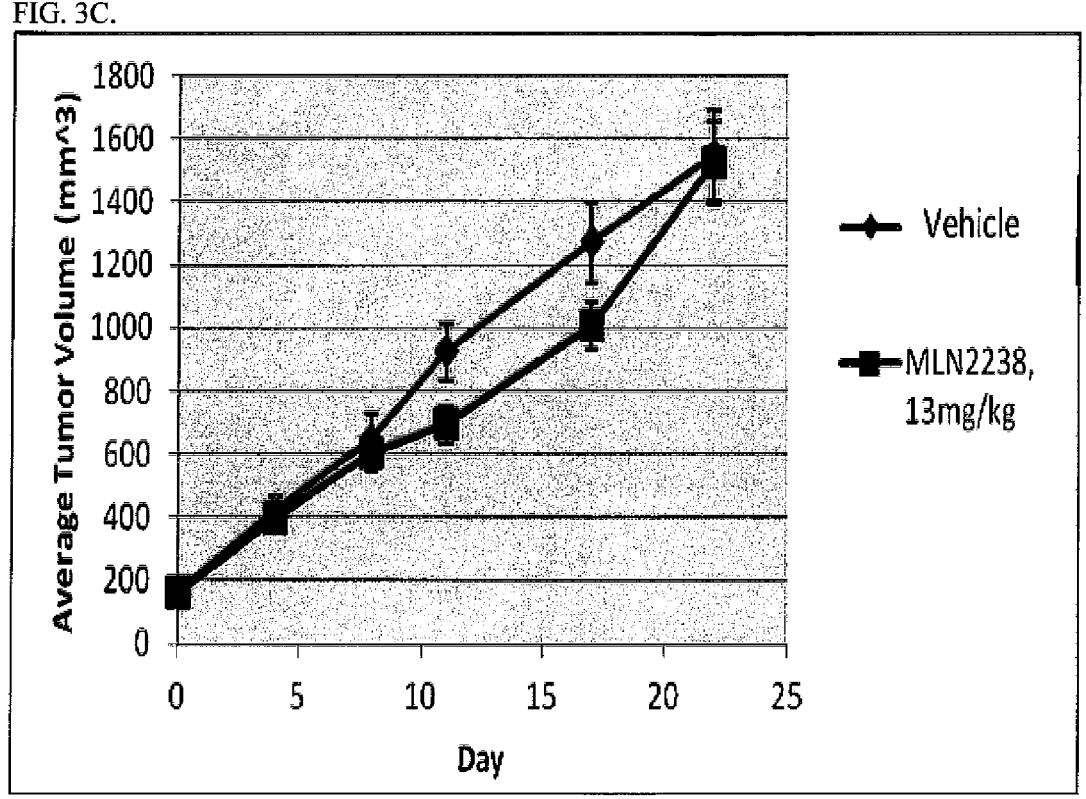

The impacts of KRas mutation on MLN2238 response in vivo were further assessed using KRas-SW48 isogenic colon cell lines (Horizon Discovery Ltd), in which KRas-G13D and KRas-G12V mutations were introduced into SW48 cells (KRas WT) by rAAV gene editing technology to generate stable cell lines. Although in vitro sensitivity (as measured by CELLTITER-GLO® Luminescent Cell Viability Assay (Promega) at 72 hrs of treatment) to MLN2238 was similar among the three cell lines (EC50 of 33 nM, wt, 19.5 nM, G13D and 20 nM, G12V), in vivo studies showed a difference in sensitivity. FIGS. 3A-3C illustrate the time course of tumor growth in a xenograft model which has a wild type KRAS (FIG. 3A) or in a matched xenograft model in which KRAS was mutated at open reading frame codon 13 or 12 (FIGS. 3B and 3C, respectively) to substitute another amino acid for glycine at each position. The results of this matched model show that the wild type line is sensitive and the mutant lines are resistant to MLN2238 in the xenograft study. This suggests that activated KRAS can confer some level of resistance to the proteasome inhibitor.

Example 2

Glucose Transporter

In general, tumor cells exhibit higher levels of glucose metabolism than normal cells (reviewed Adekola et al. (2012) 24:650-654). KRAS mutant colorectal cancer cells showed higher glucose uptake and glycolysis and better growth and survival under nutrient stress than wild type cells (Yun et al. 2009 Science 325:1555). Those studies identified GLUT1, glucose transporter 1, as upregulated in KRAS mutant colorectal cancer cells.

Most of the tumor cell lines are sensitive to MLN2238 in vitro under standard culture conditions using high glucose, making it difficult to distinguish in vitro between cell lines which are sensitive versus resistant. However, under in vivo conditions, less glucose is available. Glucose transporter expression was analyzed by western blot of tumor cell lines listed in Table 5 not treated with MLN2238, but grown as xenografts in mice or grown in culture. Proteins were prepared from xenograft tumor samples or cell samples in MPER mammalian protein extraction reagent from Thermo Scientific (VA). Equal amounts of proteins were run in 4-12% Bis-Tris gel, transferred onto PVDF membrane and analyzed using reagents by LI-COR (Lincoln, Nebr.). The primary antibody was rabbit polyclonal antibody to mammalian glucose transporter 4 (Abeam, Cambridge, Mass., cat #ab654). Analysis of GLUT4 levels in many cell types (FIG. 4A for cultured cells and FIG. 4B for xenografts (one lane per animal)) shows that GLUT4 levels are higher in KRAS mutant cells and xenografts than in KRAS wild type cells and xenografts. These results suggest that the lower GLUT4 levels in KRAS-wild type tumors may play a role in their sensitivity to MLN2238. Conversely, the higher GLUT4 levels in KRAS mutant tumors may allow them to survive the stress of proteasome inhibition by MLN2238.

Example 3

Additional Sequencing Methods and General Procedures

SANGER Sequencing Methodology.

PCR amplifications are conducted using optimized cycling conditions per gene-exon. Primer extension sequencing is performed using Applied Biosystems BigDye version 3.1. The reactions are then run on Applied Biosystem's 3730xl DNA Analyzer. Sequencing base calls are done using KBTM Basecaller (Applied Biosystems). Somatic Mutation calls are determined by Mutation Surveyor (SoftGenetics) and confirmed manually by aligning sequencing data with the corresponding reference sequence using Seqman (DNASTAR).

Next Generation Sequencing (NGS) Methodology.

Targeted NGS using the Illumina platform (Illumina, Inc. San Diego, Calif.) is used to confirm and identify low frequency mutations in a marker. Primer pairs are designed to amplify coding exons. PCR products are quantified using a PicoGreen assay and combined in equal molar ratios for each sample. The purified products are end-repaired and concatenated by ligation. The concatenated products are used for Hi-Seq 2000 library preparation. The concatenated PCR products are sheared and used to make barcoded Hi-Seq 2000 libraries consisting of 12 bar-coded samples per multiplexed pool. The pooled Hi-Seq 2000 libraries undergo clonal amplification by cluster generation on eight lanes of a Hi-Seq 2000 flow cell and are sequenced using 1×100 single-end sequencing on a Hi-Seq 2000. Matching of primary sequencing reads to the human genome build Hg18, as well as SNP analysis are performed using Illumina's CASAVA software version 1.7.1.

Preparation of Compounds and Pharmaceutical Compositions.

The compound of formula (II), [(1R)-1-({[(2,4-dichlorobenzoyl)amino]acetyl{-amino)-3-methylbutyl]boronic acid, is prepared by methods disclosed in Olhava and Danca, U.S. Pat. No. 7,442,830, herein incorporated by reference in its entirety. The compound of formula (III-A), 2,2'-{2-[(1R)-1-({[(2,5dichlorobenzoyl)amino]acetyl}amino)-3-methylbutyl]-5-oxo-1,3,2-dioxaborolane-4,4-diyl}diacetic acid, is prepared by methods disclosed in Elliott et al., WO 09/154737, herein incorporated by reference in its entirety. An oral capsule formulation of the compound of formula (III-A) is prepared by methods disclosed in Elliott et al., WO 09/154737, herein incorporated by reference in its entirety. An IV formulation of the compound of formula (III-A) is prepared by methods disclosed in Elliott et al., WO 09/154737, herein incorporated by reference in its entirety. A lyophilized formulation of the compound of formula (III-A) suitable for reconstitution into an IV formulation is prepared by methods disclosed in Elliott et al., WO 09/154737, herein incorporated by reference in its entirety.

Quantitative RT-PCR.

cDNA synthesis and quantitative RT-PCR is performed using ABI Gene Expression Assays, reagents, and ABI PRISM® 7900HT Sequence Detection Systems (Applied Biosystems, Foster City, Calif.) using the following cycle conditions: hold at 50° C. for 2 minutes for AmpErase UNG activation, then 95.0° C. for 10 minutes to activate DNA polymerase then run 40 two-part cycles of 95.0° C. for 15 seconds and 60.0° C. for 1 minute. The dCt is calculated by using the average Ct of control genes B2M (Hs99999907_m1) and RPLPO (Hs99999902 m1). Relative mRNA expression quantification is derived using the Comparative Ct Method (Applied Biosystems). mRNA expression fold change values are generated from a normal sample and corresponding tumor sample.

EQUIVALENTS

Although embodiments of the invention have been described using specific terms, such description are for illustrative purposes only, and it is to be understood that changes and variations may be made without departing from the spirit or scope of the invention. Those skilled in the art will recognize, or be able to ascertain using no more than routine experimentation, many equivalents of the specific embodiments of the invention described herein. Such equivalents are intended to be encompassed by the following claims.

What is claimed:

1. A method for treating a patient having a solid tumor comprising wild type KRAS status, comprising the step of administering to the patient a therapeutically effective amount of Ixazomib citrate, MLN2238 or a boronate ester thereof, wherein the solid tumor comprising wild type KRAS status is selected from the group consisting of a lung tumor and a colon tumor.

2. The method of claim 1, further comprising the steps of:
   a) measuring at least one characteristic of at least one marker associated with at least one marker gene in a patient sample comprising tumor cells, wherein the at least one characteristic is selected from the group consisting of size, sequence, composition, activity and amount, and wherein at least one marker gene is v-Ki-ras2 Kirsten rat sarcoma viral oncogene homolog (KRAS);
   b) identifying whether the at least one characteristic measured in step a) is informative for outcome of treatment with the compound; and
   c) administering the Ixazomib citrate, MLN2238 or a boronate ester thereof to the patient with tumor cells that comprise wild type KRAS.

3. The method of claim 2, wherein the at least one marker is selected from the group consisting of nucleic acid and protein corresponding to the at least one marker gene.

4. The method of claim 3, wherein the at least one marker is sequence.

5. The method of claim 3, wherein the at least one marker is nucleic acid.

6. The method of claim 5, wherein the nucleic acid is selected from the group consisting of DNA, mRNA and cDNA or a portion of any of the foregoing, wherein the portion comprises at least one mutation site of the at least one marker gene.

7. The method of claim 6, wherein the nucleic acid comprises a codon of SEQ ID NO:2 selected from the group consisting of codon 12, codon 13 and codon 61, or a variant thereof, or a complement thereof.

8. The method of claim 2, wherein the at least one marker gene is at least two marker genes.

9. The method of claim 1, wherein the amount of GLUT4 in the patient sample is measured.

10. The method of claim 8, wherein the amount of GLUT4 in the patient sample is measured.

11. The method of claim 10, wherein the amount of GLUT4 is normal or low.

12. The method of claim 2, wherein the sample comprises tumor exudate.

13. The method of claim 12, further comprising enriching the sample for tumor cells.

14. The method of claim 9, wherein the amount of GLUT4 is normal or low.

15. The method of claim 1, wherein the wild type KRAS status is identified from a sample that comprises tumor exudate.

16. The method of claim 15, further comprising enriching the sample for tumor cells.

17. The method of claim 1, wherein the Ixazomib citrate, MLN2238 or a boronate ester thereof is the compound of formula (III-A):

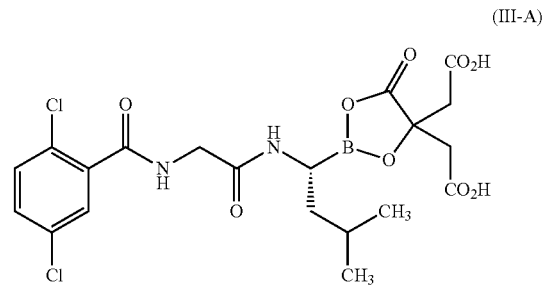 [SMILES: CC(C)C[C@H](NC(=O)CNC(=O)c1cc(Cl)ccc1Cl)B1OC(=O)C(CC(=O)O)(CC(=O)O)O1]

(III-A)

or a pharmaceutically acceptable salt or a pharmaceutical composition thereof.

18. The method of claim 2, wherein the Ixazomib citrate, MLN2238 or a boronate ester thereof is the compound of formula (III-A):

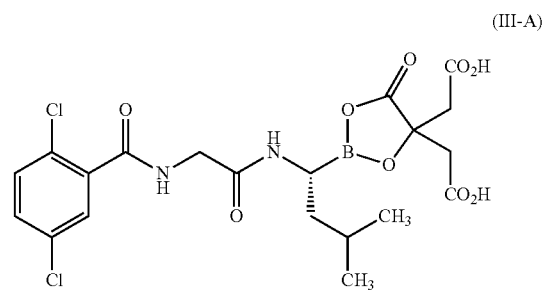 [SMILES: CC(C)C[C@H](NC(=O)CNC(=O)c1cc(Cl)ccc1Cl)B1OC(=O)C(CC(=O)O)(CC(=O)O)O1]

(III-A)

or a pharmaceutically acceptable salt or a pharmaceutical composition thereof.

* * * * *